(12) United States Patent
Yung et al.

(10) Patent No.: US 11,434,470 B2
(45) Date of Patent: *Sep. 6, 2022

(54) BIOCOMPATIBLE SCULPTURED EXTRACELLULAR NANOMATRIX ENABLES SELF ASSEMBLY OF NEURAL STEM CELLS INTO MINIATURE BRAIN ORGANOIDS OF SUBSTANTIA NIGRA

(71) Applicant: Hong Kong Baptist University, Hong Kong (HK)

(72) Inventors: Kin Lam Yung, Hong Kong (HK); Zhifeng Huang, Hong Kong (HK); Shi Qing Zhang, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 934 days.

This patent is subject to a terminal disclaimer.

(21) Appl. No.: 16/209,934

(22) Filed: Dec. 4, 2018

(65) Prior Publication Data

US 2019/0106676 A1 Apr. 11, 2019

Related U.S. Application Data

(63) Continuation-in-part of application No. 15/600,808, filed on May 22, 2017, now Pat. No. 10,619,135.
(Continued)

(51) Int. Cl.
*C12N 5/0793* (2010.01)
*C12N 5/071* (2010.01)
*B82Y 5/00* (2011.01)

(52) U.S. Cl.
CPC ......... *C12N 5/0619* (2013.01); *C12N 5/0697* (2013.01); *B82Y 5/00* (2013.01);
(Continued)

(58) Field of Classification Search
CPC .. C12N 5/0619; C12N 5/0697; C12N 5/0623; C12N 13/00; C12N 2533/00;
(Continued)

(56) References Cited

U.S. PATENT DOCUMENTS

2012/0118371 A1* 5/2012 Yoshida ............ H01L 31/03925
136/256

FOREIGN PATENT DOCUMENTS

WO 2011100638 A1 8/2011

OTHER PUBLICATIONS

European Search Report of corresponding European Patent Application No. 17802132.5 dated Nov. 21, 2019.
(Continued)

*Primary Examiner* — Smita S Patel
(74) *Attorney, Agent, or Firm* — Idea Intellectual Limited; Margaret A. Burke; Sam T. Yip

(57) ABSTRACT

Biocompatible silica inorganic sculptured extracellular nanomatrices (iSECnMs) of silica nanozigzags are deposited by glancing angle deposition (GLAD), to achieve induction of specific differentiation without growth factors. The nanostructure includes a plurality of nanozigzags. The nanozigzags include $SiO_2$ and the nanozigzags having a pitch of 80 nm to 250 nm, and a contact depth of 90 nm to 260 nm. A method of cell therapy including substantia nigra organoids formed on silica iSECnMs is also provided.

4 Claims, 50 Drawing Sheets
(21 of 50 Drawing Sheet(s) Filed in Color)

Related U.S. Application Data

(60) Provisional application No. 62/340,500, filed on May 23, 2016.

(52) U.S. Cl.
CPC ...... *C12N 2533/00* (2013.01); *C12N 2533/10* (2013.01); *C12N 2535/00* (2013.01)

(58) Field of Classification Search
CPC ............ C12N 2533/10; C12N 2535/00; C12N 2506/03; C12N 5/071; C12N 5/0793; B82Y 5/00; C01G 23/043
See application file for complete search history.

(56) References Cited

OTHER PUBLICATIONS

Zhifeng Huang et al., "Wafer-scale, three-dimensional helical porous thin films deposited at a glancing angle", Nanoscale, 2014, vol. 6, No. 16, pp. 9401-9409.

Hyunah Kwon et al., "Three-Dimensional Metal-Oxide Nanohelix Arrays Fabricated by Oblique Angle Deposition: Fabrication, Properties, and Applications", Nanoscale Research Letters, 2015, vol. 10, No. 1, p. 1-12.

Linxin Hu et al., "Fabrication of Optical Tunable Helical Thin Films", Journal of Materials Science & Technology, 2012, vol. 28, No. 2, pp. 97-102.

Shiqing Zhang et al., "Extracellular Nanomatrix-Induced Self-Organization of Neural Stem Cells into Miniature Substantia Nigra-Like Structures with Therapeutic Effects on Parkinsonian Rats", Advanced Science, 2019, pp. 1901822.

Omar F. Zouani et al., Altered nanofeature size dictates stem cell differentiation, Journal of Cell Science, 2012, 125, p. 1217-1224.

S. Kelly et al., Transplanted human fetal neural stem cells survive, migrate, and differentiate in ischemic rat cerebral cortex, PNAS Aug. 10, 2004 101 (32) p. 11839-11844.

\* cited by examiner

V: Vertical

Z: Zigzag

R: Right Helix

L: Left Helix

BIOCOMPATIBLE SCULPTURED EXTRACELLULAR NANOMATRIX ENABLES SELF ASSEMBLY OF NEURAL STEM CELLS INTO MINIATURE BRAIN ORGANOIDS OF SUBSTANTIA NIGRA

CROSS-REFERENCE TO RELATED APPLICATIONS

The present application is a continuation-in-part application of U.S. non-provisional application Ser. No. 15/600,808 filed on May 22, 2017 which claims priority from U.S. Provisional Patent Application Ser. No. 62/340,500 filed on May 23, 2016. The disclosures of all the above referenced patent applications are hereby incorporated by reference in their entirety.

FIELD OF INVENTION

This invention is in the field of biotechnology and medical industries. In particular, this invention relates to substantia nigra organoids in silica inorganic sculptured extracellular nanomatrices (iSECnMs), method of forming the same and use of the substantia nigra organoids in cell therapy.

BACKGROUND OF INVENTION

In recent years stem cell therapies have been developed and progress extremely fast in biomedical sciences. It will be hope for treating neurodegenerative diseases, such as Alzheimer's disease, Parkinson's disease and even stroke. During stem cell therapies, cell culture technology is used. Chemical growth factors (GFs) must be employed in order to induce stem cell proliferation and cell differentiation. Many of these growth factors are the same growth factors that can promote growth of cancer cells and cancer metastasis. Therefore, there are urgent needs to develop methods to induce in vitro stem cell proliferation and differentiation without using chemical growth factors.

Objective of the present invention is to provide methods and physical substrates for proliferation and differentiation of neural stem cells by means of physical structures without the need of using chemical growth factors.

To the best of the inventors' knowledge, the present invention disclosed herein is novel and inventive over the state of art.

Citation or identification of any reference in this section or any other section of this application shall not be construed as an admission that such reference is available as prior art for the present application.

SUMMARY OF INVENTION

The present invention is in the field of biotechnology and medical industries. In particular, this invention relates to methods and substrates for cell differentiation of neural stem cells. In one embodiment of the present invention, there is provided methods and substrates for differentiation of neural stem cells by means of physical structures without the need of using growth factors.

In a first aspect of the present invention, there is provided a nanostructure comprising a plurality of nanohelices or nanozigzags, wherein the plurality of nanohelices or nanozigzags are made of materials comprising $SiO_2$ or $TiO_x$ wherein x is in the range of $0.33 \leq x \leq 2$.

In a second embodiment of the first aspect of the present invention, there is provided a nanostructure comprising a plurality of nanohelices or nanozigzags, wherein said stem cells are neural stem cells.

In a first embodiment of the first aspect of the present invention, there is provided a nanostructure comprising a plurality of nanohelices or nanozigzags, wherein length of each nanohelix is at least 540 nm, each nanohelix comprises at least two pitches and having a helical pitch of at least 240 nm.

In a second embodiment of the first aspect of the present invention, there is provided a nanostructure comprising a plurality of nanohelices or nanozigzags, wherein the length of each nanozigzag is at least 550 nm, each nanozigzag comprises at least three pitches and having a pitch of at least 165 nm.

In a third embodiment of the first aspect of the present invention, there is provided a nanostructure comprising a plurality of nanohelices or nanozigzags, wherein the $SiO_2$ nanohelices have a stiffness of $12.6 \pm 1.8$ µN/nm.

In a fourth embodiment of the first aspect of the present invention, there is provided a nanostructure comprising a plurality of nanohelices or nanozigzags, wherein the $SiO_2$ nanozigzags have a stiffness of $19.7 \pm 2.3$ µN/nm.

In a fifth embodiment of the first aspect of the present invention, there is provided a nanostructure comprising a plurality of nanohelices or nanozigzags, wherein said nanostructure is manufactured using the GLAD technique.

In a sixth embodiment of the first aspect of the present invention, there is provided a nanostructure comprising a plurality of nanohelices or nanozigzags, wherein the $TiO_x$, wherein x is in the range of $0.33 \leq x \leq 2$ and the nanostructure has a shape independent stiffness of no more than 26 µN/nm.

In a seventh embodiment of the first aspect of the present invention, there is provided a nanostructure comprising a plurality of nanohelices or nanozigzags, wherein the nanohelices are left-hand oriented or right-handed oriented.

In a second aspect of the present invention, there is provided a nanostructure for inducing proliferation and differentiation of stem cells in the absence of chemical growth factors, wherein said nanostructure is made out of materials comprising $SiO_2$.

In a first embodiment of the second aspect of the present invention, there is provided a nanostructure for inducing proliferation and differentiation of stem cells in the absence of chemical growth factors, wherein said nanostructure comprises a plurality of nanohelices or nanozigzags.

In a second embodiment of the second aspect of the present invention, there is provided a nanostructure for inducing proliferation and differentiation of stem cells in the absence of chemical growth factors, wherein said stem cells are neural stem cells.

In a third embodiment of the second aspect of the present invention, there is provided a nanostructure for inducing proliferation and differentiation of stem cells in the absence of chemical growth factors, wherein length of each nanohelix is at least 540 nm, each nanohelix comprises at least two pitches and having a pitch of at least 240 nm.

In a fourth embodiment of the second aspect of the present invention, there is provided a nanostructure for inducing proliferation and differentiation of stem cells in the absence of chemical growth factors, wherein length of each nanozigzags is at least 550 nm, each nanozigzag comprises at least three pitches and having a pitch of at least 165 nm.

In a fifth embodiment of the second aspect of the present invention, there is provided a nanostructure for inducing proliferation and differentiation of stem cells in the absence of chemical growth factors, wherein the $SiO_2$ nanohelices have a stiffness of 12.6±1.8 μN/nm.

In a sixth embodiment of the second aspect of the present invention, there is provided a nanostructure for inducing proliferation and differentiation of stem cells in the absence of chemical growth factors, wherein the $SiO_2$ nanozigzags have a stiffness of 19.7±2.3 μN/nm.

In a seventh embodiment of the second aspect of the present invention, there is provided a nanostructure for inducing proliferation and differentiation of stem cells in the absence of chemical growth factors, wherein said nanostructure is manufactured using the GLAD technique.

In a eighth embodiment of the second aspect of the present invention, there is provided a nanostructure for inducing proliferation and differentiation of stem cells in the absence of chemical growth factors, wherein the nanohelices are left-hand or right-hand oriented.

In the third aspect of the present invention, it is provided a nanostructure comprising a plurality of nanozigzags, wherein the nanozigzags comprises $SiO_2$. In the first embodiment of the third aspect of the present invention, the nanozigzags have a pitch of 80 nm to 250 nm. The nanozigzags have a pitch of 80 nm-225 nm. The nanozigzags have a pitch of 80 nm, 170 nm or 225 nm. The nanozigzags have a contact depth of 90 nm to 260 nm. The nanozigzags comprise at least three pitches.

In the second embodiment of the third aspect of the present invention, it is provided a method of promoting differentiation of neural stem cells to neurons comprising providing the nanostructure and culturing the neural stem cells on the nanostructure. In one embodiment, the culturing step is performed in the absence of growth factor. In one embodiment, the neural stem cells differentiate into dopaminergic neurons, GABAergic neurons or glutamatergic neurons.

In the third embodiment of third aspect of the present invention, it is provided a method of forming a substantis nigra organoid comprising providing the nanostructure of and culturing neural stem cells on the nanostructure. In one embodiment, the culturing step is performed in the absence of growth factor. In embodiment, the neural stem cells are cultured for 14 days or more.

In the fourth embodiment of the third aspect of the present invention, it is provided substantis nigra organoid formed by culturing neural stem cells on a nanostructure.

Features, integers, characteristics, compounds, chemical moieties or groups described in conjunction with a particular aspect, embodiment or example of the invention are to be understood to be applicable to any other aspect, embodiment or example described herein unless incompatible therewith.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The patent or application file contains at least one drawing executed in color. Copies of this patent or patent application publication with color drawing(s) will be provided by the Office upon request and payment of the necessary fee.

The above and other objects and features of the present invention will become apparent from the following description of the invention, when taken in conjunction with the accompanying drawings, in which.

DETAILED DESCRIPTION OF INVENTION

Figure 1A:
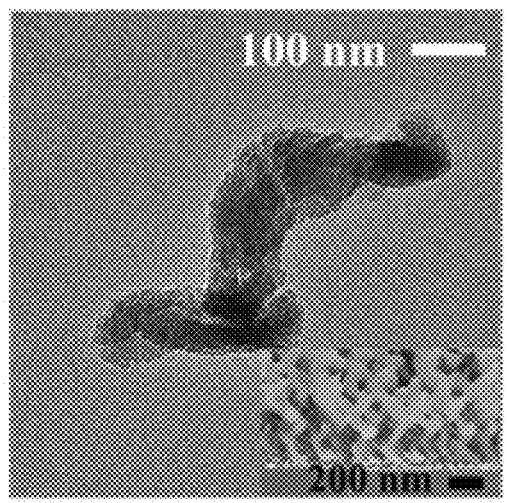
FIG. 1a shows TEM image of $SiO_2$ ECnM by GLAD having two-pitch left-handed nanohelices (NHs). Insets: cross-sectional SEM images of the ECnMs.

The present invention is not to be limited in scope by any of the specific embodiments described herein. The following embodiments are presented for exemplification only.

In recent years, stem cell therapies have been developed and made extremely fast progress in biomedical science. Neural stem cells (NSCs) are self-renewing and multipotent cells utilized for treating various neurodegenerative diseases. Chemical growth factors (GFs) are widely employed to induce stem cell proliferation and differentiation. Nowadays, in a commonly used NSC-culture method, "neurosphere assay", the growth of cells substantially relies on GFs; differentiated cells die in a few days and some undifferentiated cells can proliferate actively in respond to epidermal GFs and basic fibroblastic GFs to form neurospheres. However, GFs are potent to regulate cell-signaling pathways. If large amount of GFs is used to induce in vitro stem cells differentiation, it may cause a risk to develop cancer cells in vitro or tumors in vivo after transplantation. For example, fibroblast GF signaling, crucial for cell proliferation, survival and migration, plays an oncogenic role in many cancers; vascular epidermal GFs (an inducer of angiogenesis) and deregulated insulin GFs are related to the initiation and progression of cancer. Therefore, there is an urgent demand on developing new methods to induce in vitro NSC proliferation and differentiation without chemical GFs or additives.

The NSC-based therapies usually require extracellular matrices (ECMs) to vitro culture or receive additional treatment. ECMs can be made of organic scaffolds, such as poly-L-ornithine (PO), poly-L-Lysine (PLL), Laminin, and Fibronectin (FN). However, some studies suggest that PO and PLL could enhance the likelihood of host inflammatory responses, Laminin has a risk to be a carcinogenic substance, and FN would induce NSCs to lose their potentiality of proliferation after repeatedly passaged. The development of nanotechnology is penetrating biomedical sciences at a surprising speed, to devise a wide range of biocompatible/biodecomposable extracellular nanomatrices (ECnMs) to instruct the fate of stem cells in vitro. For instance, NSCs growing on stiff three-dimensional graphene foams exhibit enhanced differentiation; microarrays with nano-topographies enables the differentiation of primary murine neural progenitor cells, and disorder nanopatterns may favor stem cell lineage commitment compared to the order arrays; NSCs can successfully differentiate to neurons and astrocytes on carbon nanotubes. There are several aspects of the instructions to the fate of stem cells, which can be generally classified as biochemical and physiological cues. The biochemical cues stem from GFs, and the stem cell microenvironment of ECnMs is susceptible to multiple physiological cues, such as material, stiffness, and topography (including crystalline structure, geometric feature of nanostructures, fibrillar focal contact depth, pattern disorder, and pattern spacing). Purely mechanical support is provided to cells and some materials show no effects on cells viability. The topography cues can induce pronounced change in focal adhesion structures and alter the cytoskeleton and gene expression, to essentially influence cell attachment, migration, proliferation, and differentiation. As a result, an increasing attention has been focused on the nanotopography for its resemblance to in vitro environment. However, these studies were carried out with chemical GFs, to prevent solely studying the physiological cues. Novel biomaterials that mimic the physiological microenvironment for culturing and expanding NSCs without GFs or other additional biomaterials have attracted great interests to date. Rigidity and topographical control on ECnMs is a useful tool to understand, at both fundamental and application levels, how to encode instructions in the ECnMs for specialized cellular commitment and functions.

In the present invention, the inventors utilize the sculptured inorganic ECnMs, deposited by glancing angle deposition (GLAD), to induce GF-free NSCs proliferation and differentiation. The ECnMs of the present invention are made of biocompatible/biodegradable materials comprising $SiO_2$ or $TiO_2$, in the helices and zigzags having different topographies. The terms "ECnMs", "nanostructure" and "nano-matrices" are used interchangeably herein, which define the present invention for use in proliferation and differentiation of stem cells. The ECnMs of the present invention is made of inorganic oxides that proliferate the growth of NSCs, faster than induction by chemical GFs. The $SiO_2$ ECnMs of the present invention enables stem cells to differentiate to neuronal commitment. Both zigzag and helical nanostructure of the present invention enables stem cell differentiation. In a preferred embodiment, $SiO_2$ zigzag nanostructure mediates a better differentiation than the helical, which can be ascribed to physiological cues of topography and stiffness. In one embodiment of the present invention there is provided a GF-free method to minimize a risk of generating cancer cells for NSC therapies.

Figure 1B:
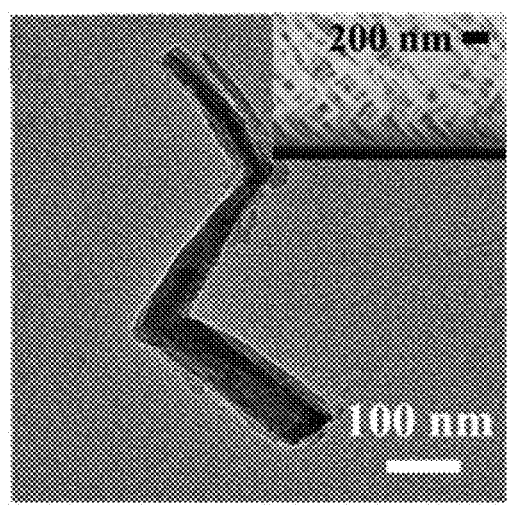
FIG. 1b shows TEM image of $SiO_2$ ECnM by GLAD having three-pitch nanozigzags (NZs). Insets: cross-sectional SEM images of the ECnMs.
Figure 1C:
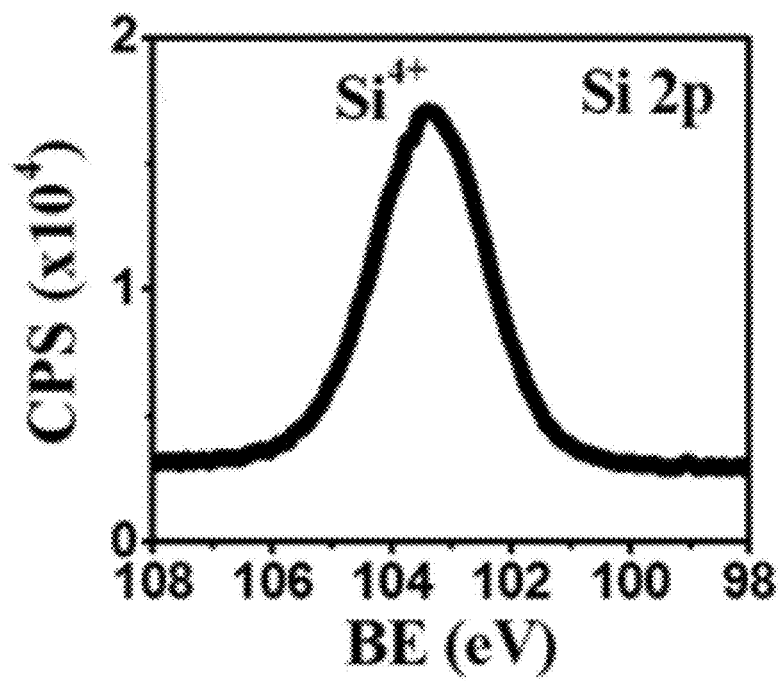
FIG. 1c shows XPS spectrum of NHs: Si2p for $SiO_2$ ECnM by GLAD.
Figure 1D:
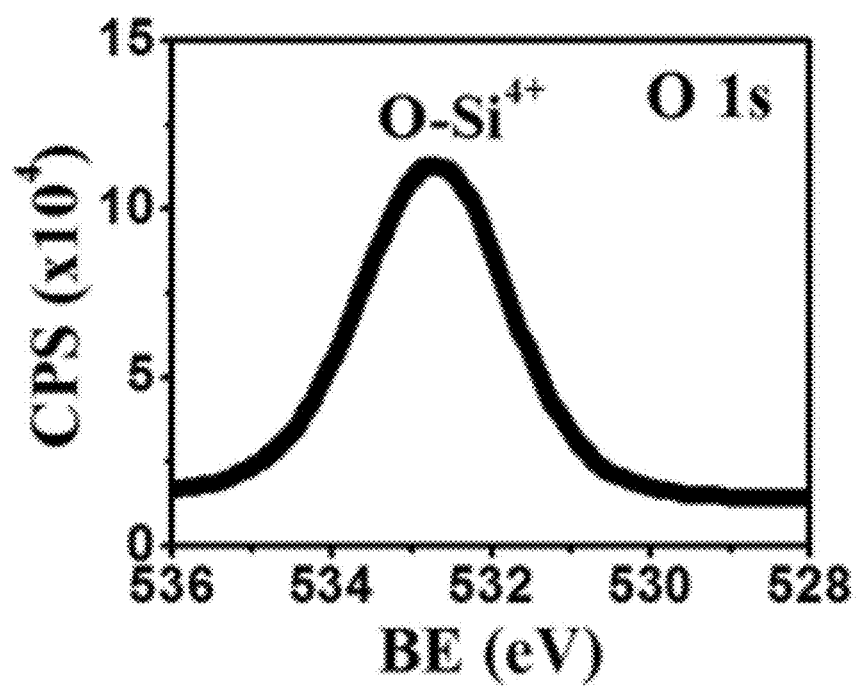
FIG. 1d shows XPS spectrum of NHs: O1s for $SiO_2$ ECnM by GLAD.
Figure 1E:
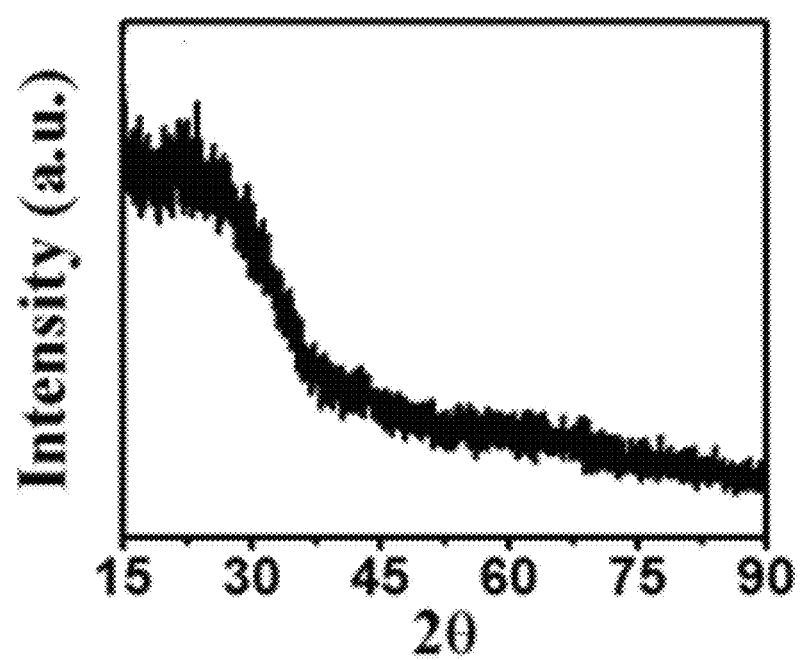
FIG. 1e shows XRD spectrum of $SiO_2$ ECnM NHs deposited on glass by GLAD.
Figure 2A:
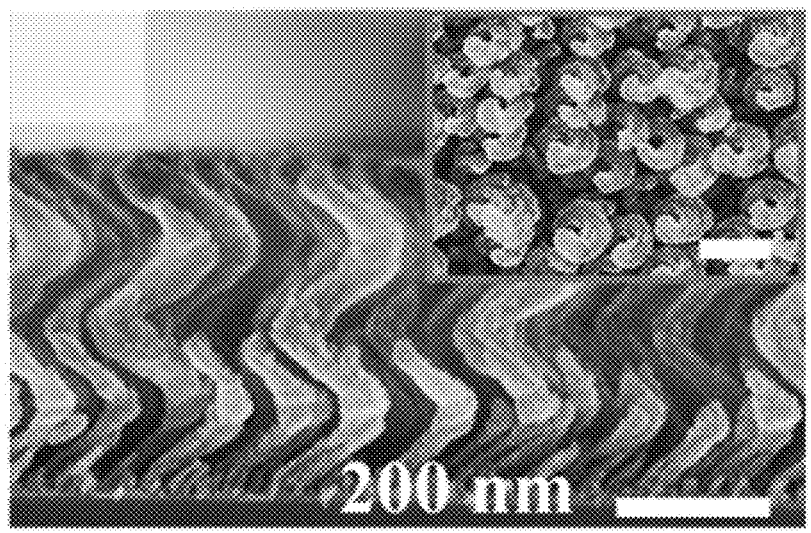
FIG. 2a shows cross sectional SEM images of left-handed NHs of $TiO_x$ ECnMs by GLAD. Insets shows top-down view of left-handed NHs $TiO_x$ ECnMs by GLAD (scale bars: 200 nm).
Figure 2B:
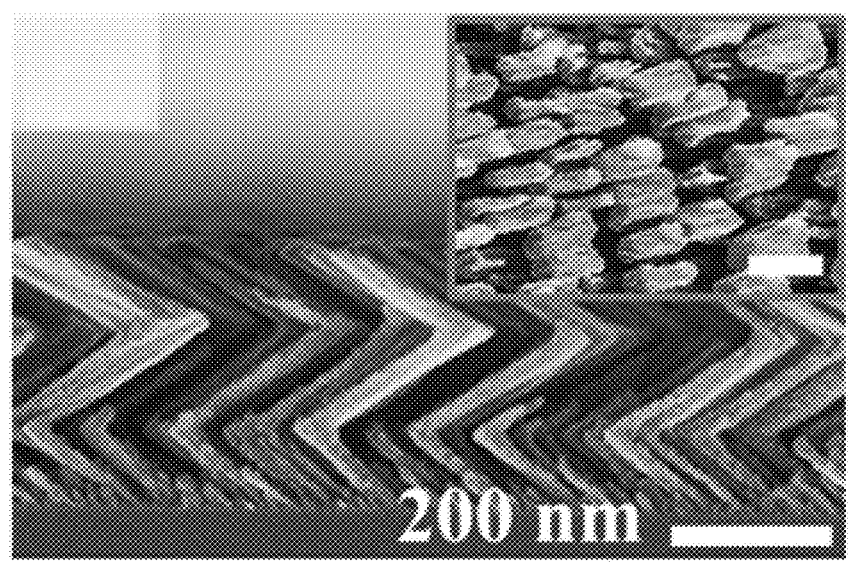
FIG. 2b shows cross sectional SEM images of NZs $TiO_x$ ECnMs by GLAD. Insets shows top-down view of NZs $TiO_x$ ECnMs by GLAD (scale bars: 200 nm).
Figure 2C:
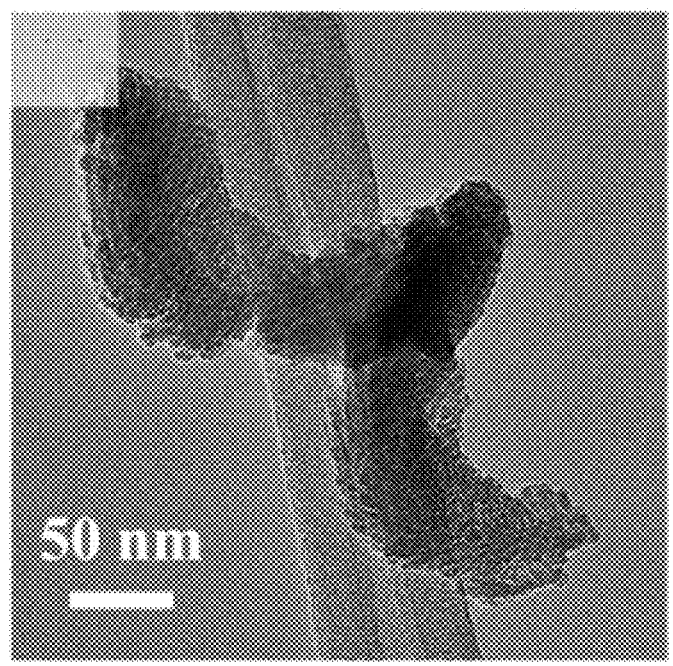
FIG. 2c shows TEM image of individual $TiO_x$ nanostructures of left-handed NHs $TiO_x$ ECnMs by GLAD.
Figure 2D:
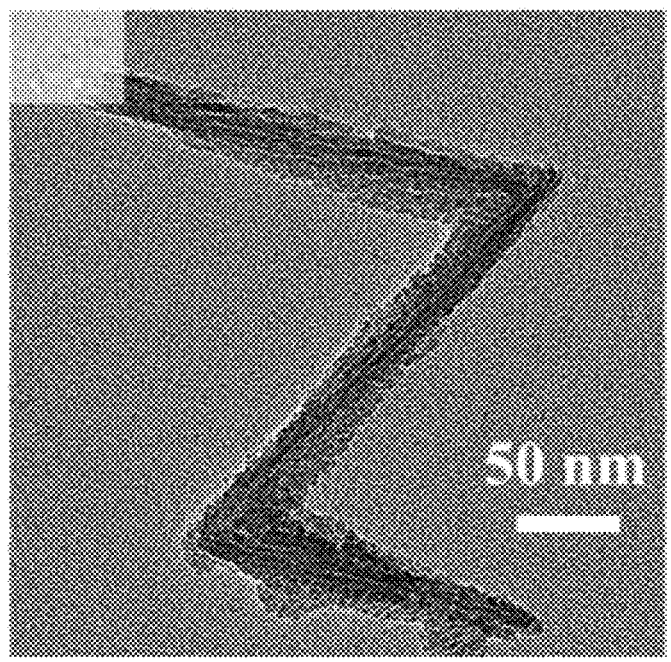
FIG. 2d shows TEM image of individual $TiO_x$ nanostructures of NZs $TiO_x$ ECnMs by GLAD.
Figure 11A:
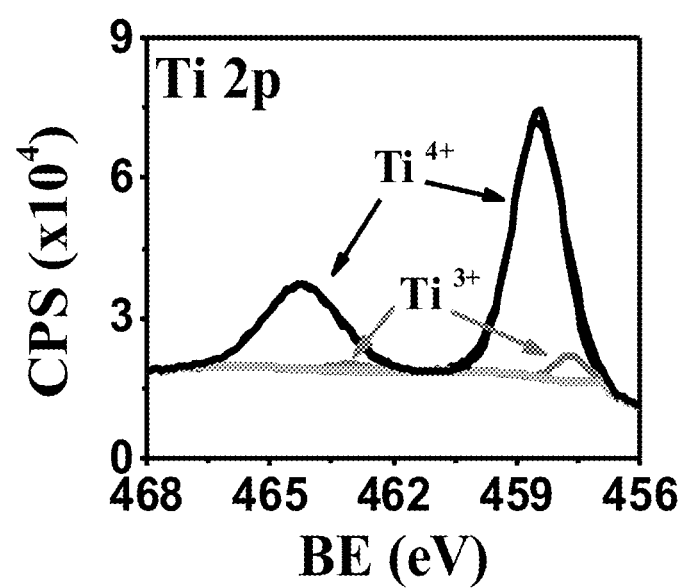
FIG. 11a shows XPS spectra of the $TiO_x$ NH ECnMs deposited on sapphire: Ti2p.
Figure 11B:
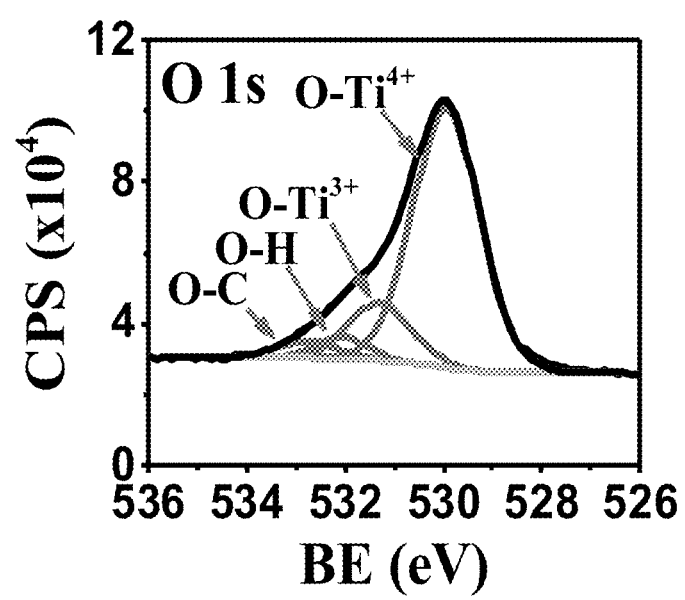
FIG. 11b shows XPS spectra of the $TiO_x$ NH ECnMs deposited on sapphire: O1s.
Figure 11C:
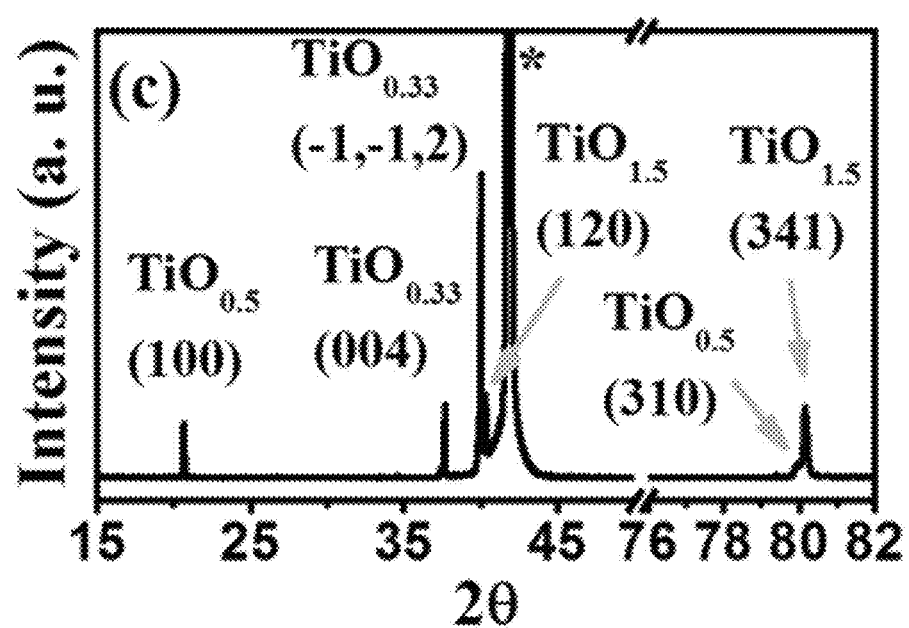
FIG. 11c shows XRD spectra of the $TiO_x$ NH ECnMs deposited on sapphire. The peak marked by asteroid is assigned to the sapphire.

GLAD is operated to deposit a close-packed silicon oxide ECnM sculptured in helix (left-handed nanohelices or NHs FIG. 1a) or zigzag (nanozigzags or NZs, FIG. 1b). The two nanostructures vertically grow along the direction of the substrate's surface normal. $Si^{4+}$ ions are mainly detected by XPS (FIGS. 1c, 1d), illustrating that the present nanostructure surfaces are composed of $SiO_2$. The present nanostructure is amorphous (FIG. 1e). The NZs have XPS and XRD spectra identical to those of the NHs, which aren't shown here. In one embodiment, the nanostructure comprises a plurality of $SiO_2$ nanohelices, length of each nanohelix (H) is at least 540 nm and each nanohelix comprises at least two pitches and having a helical pitch (P) of ~240 nm. "Zigzag" or "nanozigzag" are used interchangeably herein and are referred herein as a line or course having abrupt alternate right and left turns. In another embodiment, the nanostructure comprises a plurality of $SiO_2$ nanozigzags, length of each nanozigzag (H) is at least 550 nm and each nanozigzag comprises at least three pitches and a pitch (P) of ~165 nm (as summarized in Table 1) The helical pitch of a nanohelix or the pitch of a nanozigzag (P) herein is defined as the vertical distance separating two points on a helix or a zigzag in one complete helix turn or zigzag. n is the number of zigzags or complete helix turn in each nanozigzag or nanohelix. Length of each nanohelix/nanozigzag (H) is calculated from the formula: H=nP+d. The NHs have a surface rougher than the NZs (FIG. 1a versus 1b). Wire diameter (d) is herein defined as the diameter of the nanozigzag and nanohelix body. Wire diameter (d) of both nanostructures, especially for NZs, gradually widens along the growth direction, owing to the competition growth induced by the self-shadowing effect of GLAD. To show the dependence of the NSC proliferation and differentiation on different material of ECnMs, titanium oxides TiO$_x$ are deposited in NHs (FIGS. 2a, 2c) and NZs (FIGS. 2b, 2d) using GLAD. XPS spectra shows Ti$^{3+}$ and Ti$^{4+}$ ions are found on the nanostructure surfaces (FIGS. 11a, 11b) for TiO$_x$ NHs ECnM, where 1.5≤x≤2. XRD spectrum shows TiO$_x$, where 0.33≤x≤1.5 are found in the cores of the ECnM (FIG. 11c). No TiO$_2$ are detected on the nanostructure surfaces by XRD. This is likely due to the fact that the surface layers of TiO$_2$ are too thin to detect. It is illustrated that the core of ECnM is composed of TiO$_x$ with smaller x (0.33≤x≤1.5) and the shell or surface of ECnM is composed of TiO$_x$ with larger x (1.5≤x≤2), due to spontaneous oxidation on the surfaces prohibits further oxidation in the cores. The TiO$_x$ ECnMs appear to be shorter in length than the SiO$_2$ ECnMs sculptured in the same shape (Table 1), and have crystalline structures (FIG. 11c). Analogously, the TiO$_x$ NHs and NZs have the widening effect on d (FIGS. 2a, 2b) and rough surfaces (FIGS. 2c, 2d). SiO$_2$ has an electric conductivity lower than TiO$_x$, the SEM images of the SiO$_2$ ECnMs appear to be much more blurry than TiO$_x$ ECnMs (insets of FIGS. 1a, 1b versus FIGS. 2a, 2b). In one embodiment, the nanostructure comprises right-handed NHs made from SiO$_2$ or TiO$_x$. In another embodiment, the nanostructure comprises left-handed NHs (not shown here). In another embodiment, the nanostructure comprises right-handed and left-handed NHs.

TABLE 1

Summary of the left-handed NHs and NZs of the present invention, made of SiO$_2$ or TiO$_x$: height (H), pitch (P), number of pitch (n), and wire diameter (d) in the upper portion of the nanostructure distal to the substrate on which the nanostructure is deposited. For each sample, multiple (not less than 10) measurements are taken to evaluate algebraic average value and standard deviation.

| ECnMs | H (nm) | P (nm) | n | d (nm) |
|---|---|---|---|---|
| SiO$_2$NHs | 538 ± 4 | 241 ± 2 | 2 | 48 ± 2 |
| SiO$_2$NZs | 553 ± 3 | 165 ± 2 | 3 | 46 ± 3 |
| TiO$_x$NHs | 480 ± 3 | 213 ± 4 | 2 | 47 ± 3 |
| TiO$_x$NZs | 365 ± 7 | 138 ± 4 | 3 | 42 ± 6 |

Figure 3A:
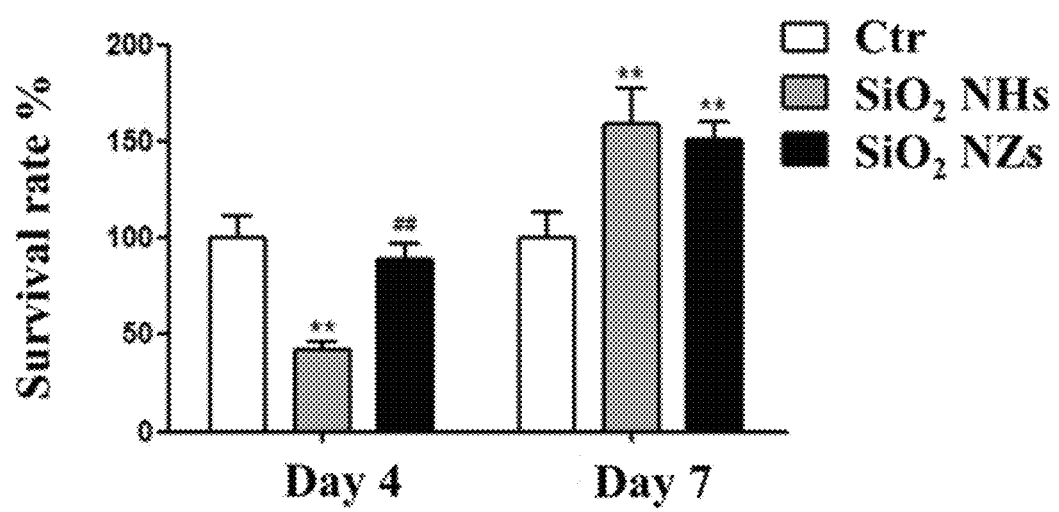
FIG. 3a shows survival rate on day 4 and day 7 of Neural stem cells (NSCs) cultured on $SiO_2$ ECnMs in a shape of the helix (NHs) and zigzag (NZs). **$p<0.01$, compared with the control group (i.e., Ctr), ##$p<0.01$, compared with the NHs group.
Figure 3B:
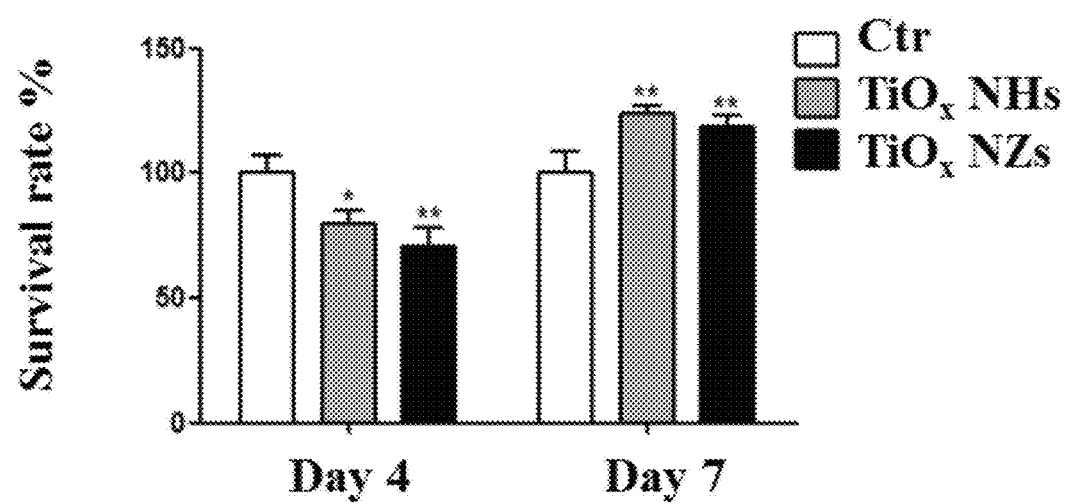
FIG. 3b shows survival rate of day 4 and day 7 of NSCs cultured on the $TiO_x$ ECnMs in a shape of the helix (NHs) and zigzag (NZs). *$p<0.05$, **$p<0.01$, compared with the control group.
Figure 5:
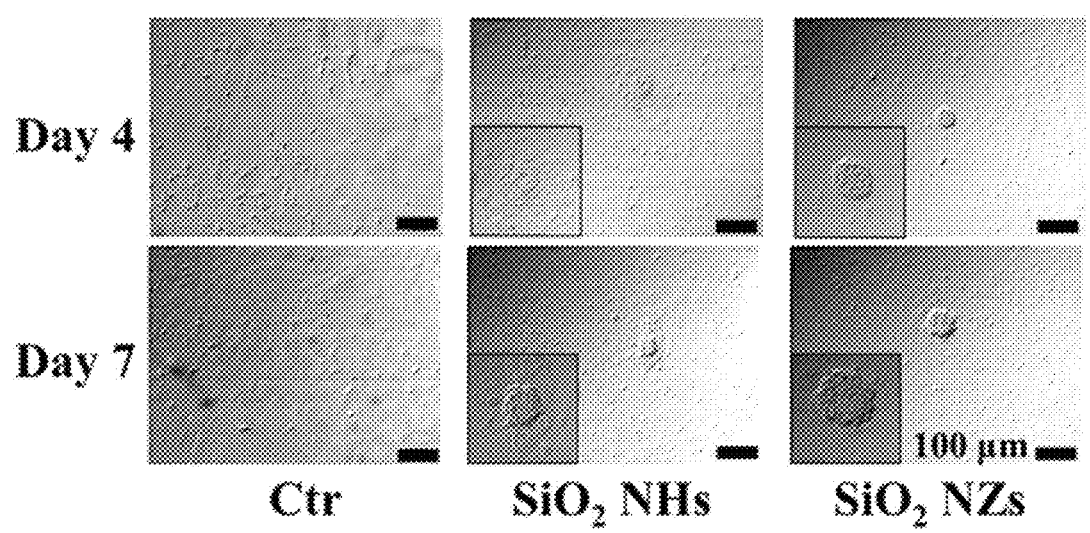
FIG. 5 shows microscopy images of neurosphere growth of NSCs having cultured on the $SiO_2$ ECnMs in a shape of the helix (NHs) or zigzag (NZs) for 4 and 7 days. Scale bar: 100 μm.
Figure 6:
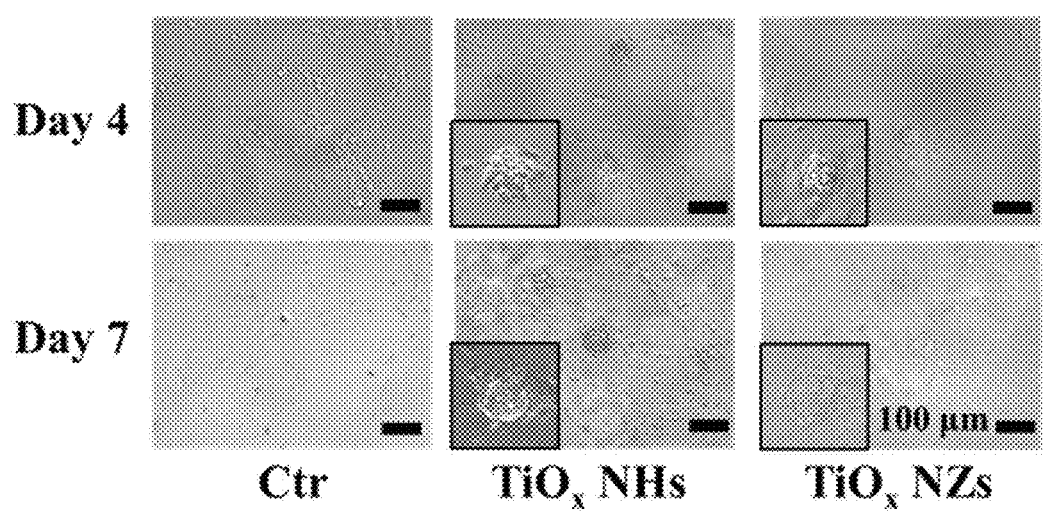
FIG. 6 shows microscopy images of neurosphere growth of NSCs having cultured on the $TiO_x$ ECnMs in a shape of the helix (NHs) or zigzag (NZs) for 4 and 7 days. Scale bar: 100 μm.

To show the proliferation of NSCs on ECnMs, MTT and neurosphere assay are performed after culturing NSCs on ECnMs for 4 and 7 days. Compared with the control group, the survival rate of NSCs on the SiO$_2$ and TiO$_x$ ECnMs decrease in day 4 but significantly increase on day 7 (FIGS. 2a and 3b). The change in survival rate of NSCs on ECnMs is ascribed to ability of ECnMs to promote proliferation of NSCs and to inhibit growth of other non-stem cells. This is further verified by studies below that show stiffness of nanostructure can control the eventual fate of non-stem cells. The degree of NSC proliferation on the helical and the zigzag structures are similar (FIGS. 2a and 3b). NHs and NZs made of SiO$_2$ or TiO$_x$ markedly promote the formation of neurospheres compared to the control group on day 4 and 7 (FIGS. 5 and 6). The neurospheres formed on day 4 have a diameter approximately larger than 50 μm. It is known in the art that neurospheres typically grow to have a diameter of 50 μm on day 5 in the presence of GFs. The inorganic ECnMs of the present invention accelerate proliferation of NSC and stimulate NSC in vitro viability without GFs.

Figure 7A:
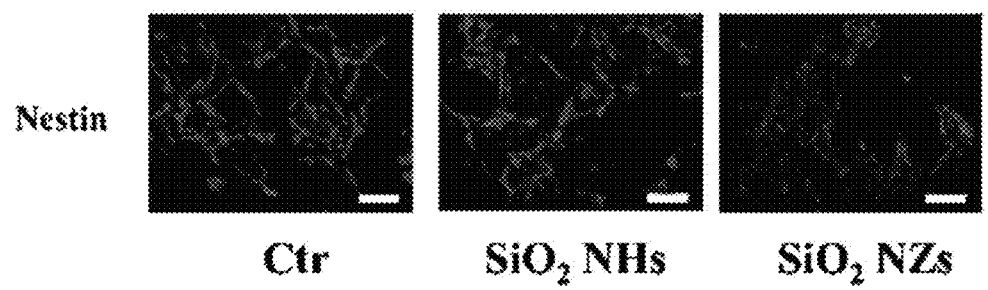
FIG. 7a shows fluorescence images of Nestin in NSC cultured on $SiO_2$ ECnMs in a shape of the helix (NHs) or zigzag (NZs). Scale bar: 50 μm.
Figure 8A:
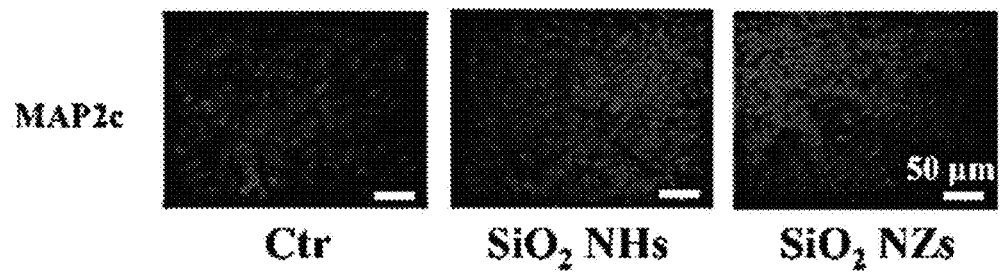
FIG. 8a shows fluorescence images of MAP2c in NSC cultured on the $SiO_2$ ECnMs in a shape of the helix (NHs) or zigzag (NZs). Scale bar: 50 μm.
Figure 9A:
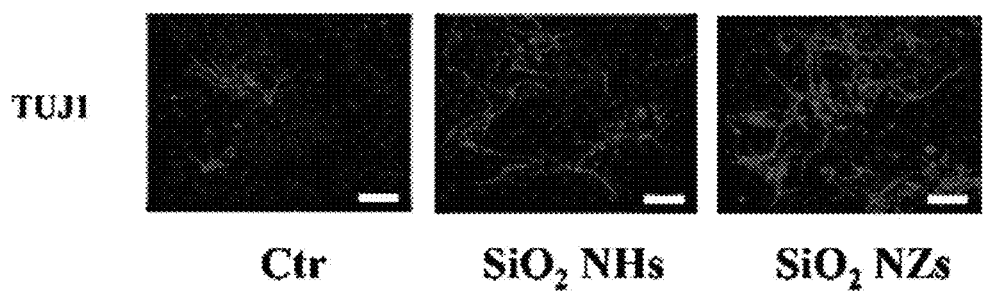
FIG. 9a shows fluorescence images of TUJ1 in NSC cultured on the $SiO_2$ ECnMs in a shape of the helix (NHs) or zigzag (NZs). Scale bar: 50 μm.
Figure 10A:
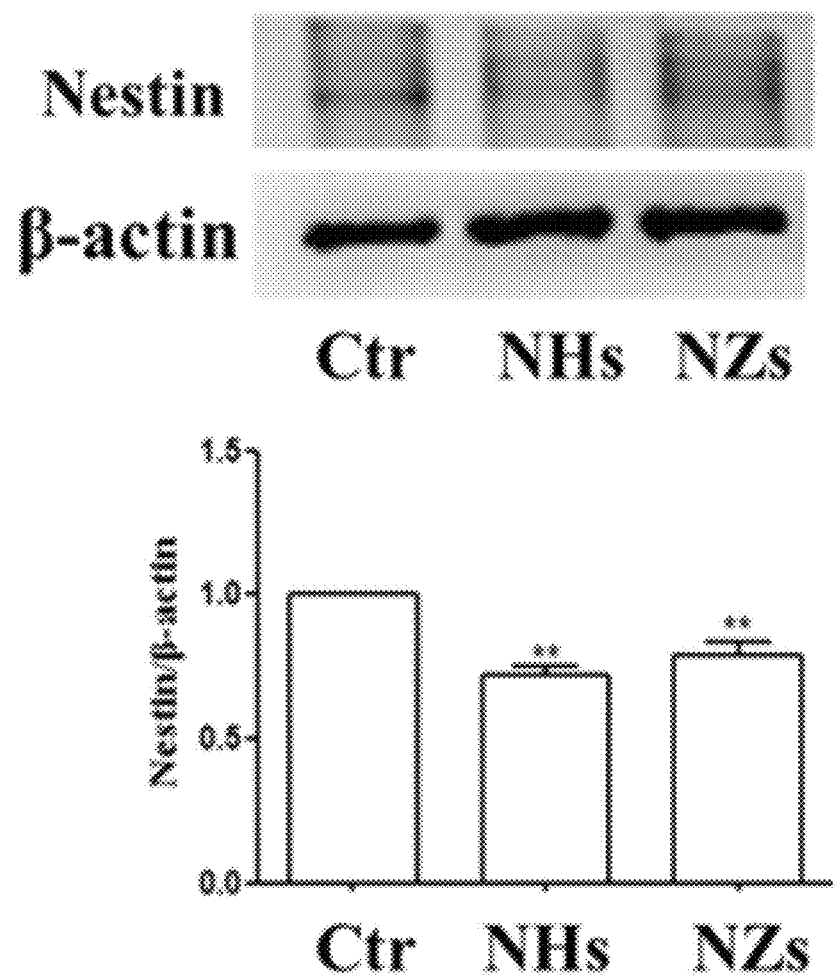
FIG. 10a shows western blot analysis of Nestin protein expression in NSC cultured on $SiO_2$ ECnMs in a shape of the helix (NHs) or zigzag (NZs) on day 4. **$p<0.01$ compared with the control group; #$p<0.05$, ##$p<0.01$ compared with the NHs group.
Figure 10B:
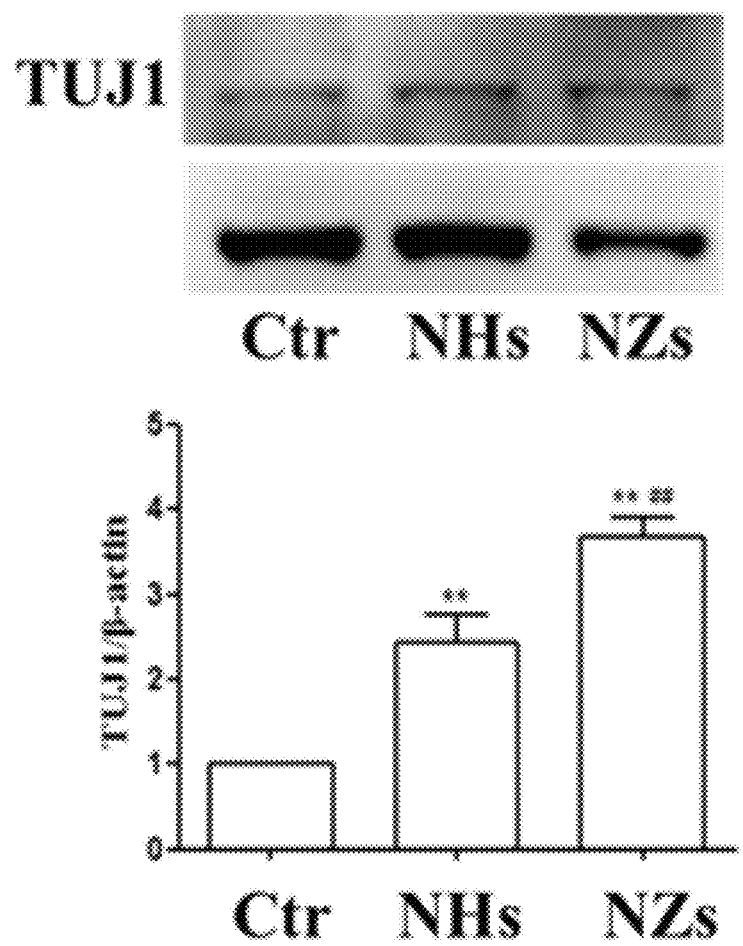
FIG. 10b shows western blot analysis of TUJ1 protein expression in NSC cultured on $SiO_2$ ECnMs in a shape of the helix (NHs) or zigzag (NZs) on day 7. **$p<0.01$ compared with the control group; #$p<0.05$, ##$p<0.01$ compared with the NHs group.
Figure 10C:
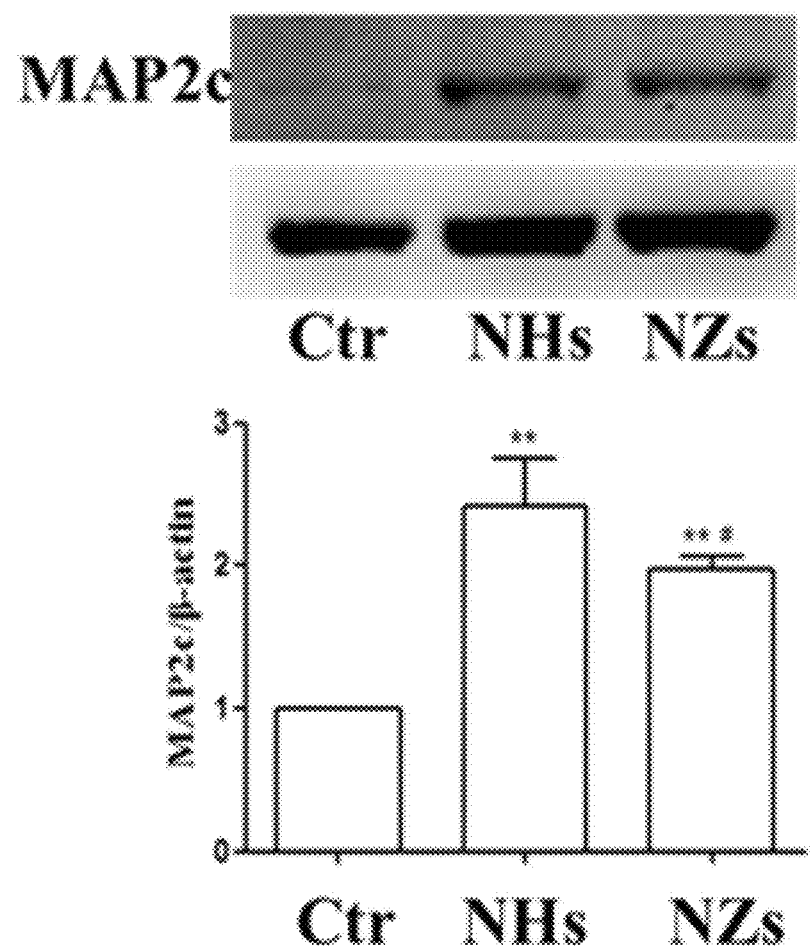
FIG. 10c shows western blot analysis of MAP2c protein expression in NSC cultured on $SiO_2$ ECnMs in a shape of the helix (NHs) or zigzag (NZs) on day 7. **$p<0.01$ compared with the control group; #$p<0.05$, ##$p<0.01$ compared with the NHs group.
Figure 10D:
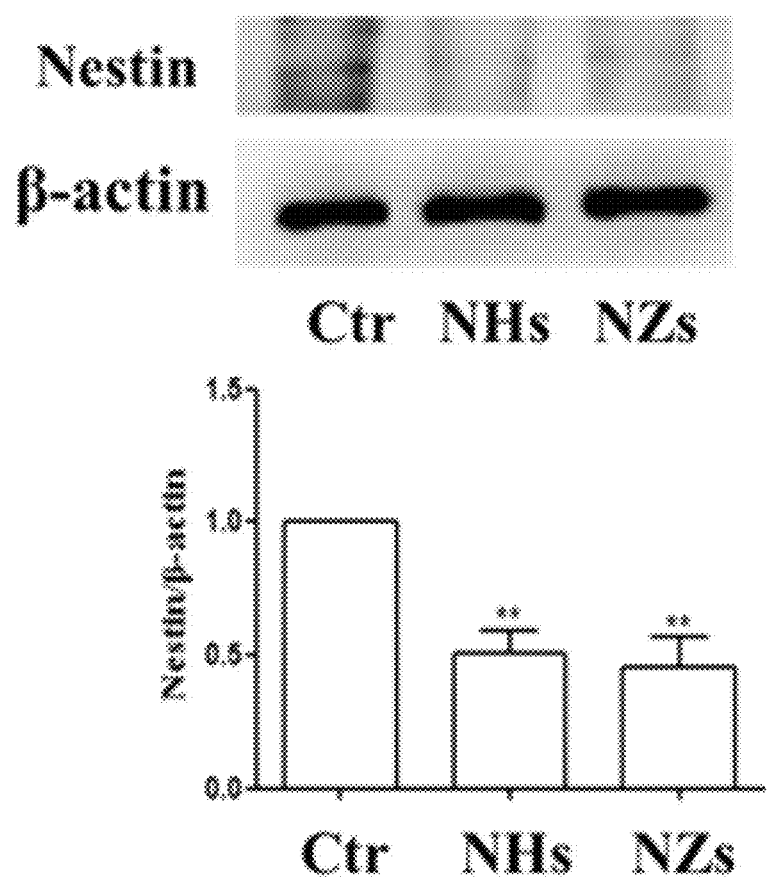
FIG. 10d shows western blot analysis of Nestin protein expression of NSC cultured on $TiO_x$ ECnMs in a shape of the helix (NHs) or zigzag (NZs) on day 4. *$p<0.05$, **$p<0.01$ compared with the control group.
Figure 10E:
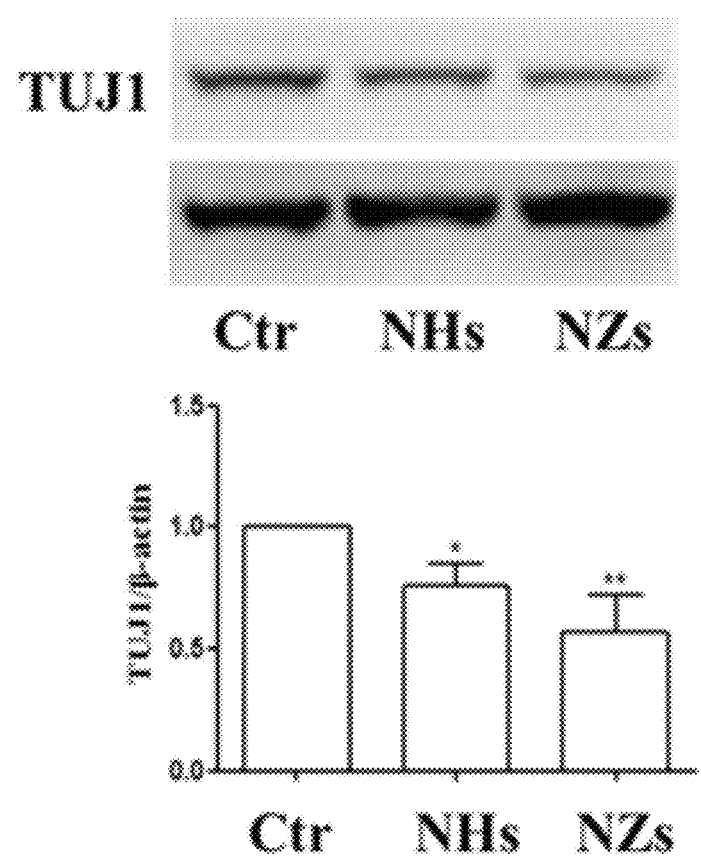
FIG. 10e shows western blot analysis of TUJ1 protein expression in NSC cultured on $TiO_x$ ECnMs in a shape of the helix (NHs) or zigzag (NZs) on day 7. *$p<0.05$, **$p<0.01$ compared with the control group.
Figure 10F:
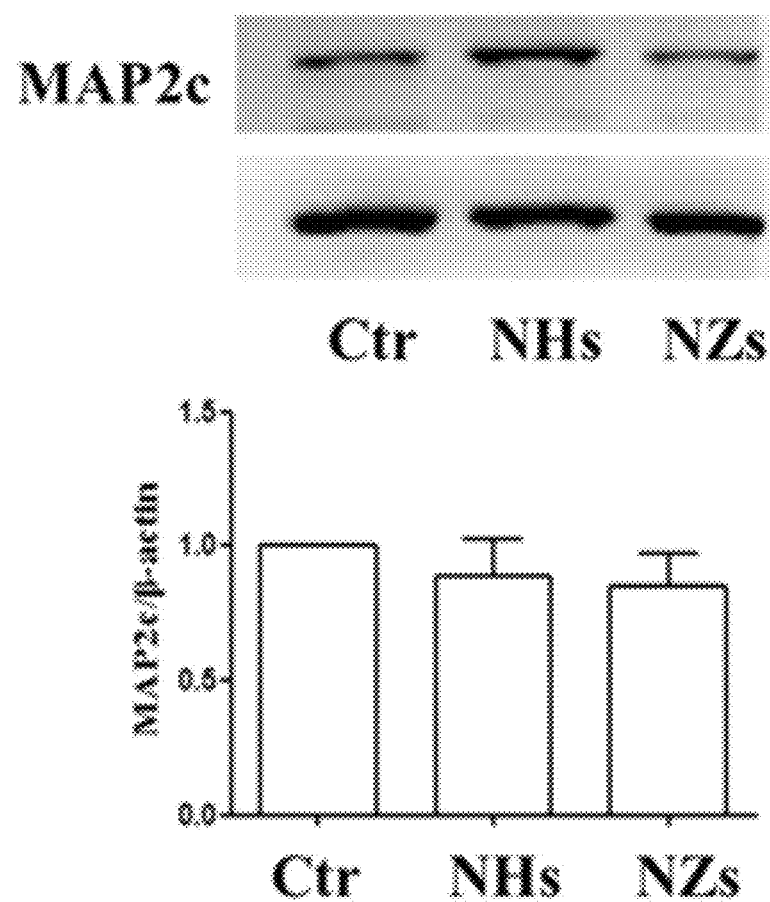
FIG. 10f shows western blot analysis of MAP2c protein expression in NSC cultured on $TiO_x$ ECnMs in a shape of the helix (NHs) or zigzag (NZs) on day 7. *$p<0.05$, **$p<0.01$ compared with the control group.

Formation of neurospheres is the first step to induce cell differentiation and neuronal cell maturation, which are crucial for neuro-repair and cell replacement therapy to treat diseases in the brain. Quick cell maturation is favored for transplantation, because it can shorten the time window to put NSCs in culture, a procedure with high medical and contamination risk. To demonstrate the NSC differentiation on the sculptured ECnMs, western blot and immunocytochemistry are performed (FIGS. 10a-10c, 7a, 8a and 9a). Western blot analysis shows that compared to the control group, on SiO$_2$ ECnMs, the expression of Nestin protein, a marker of NSCs, decreases on day 4 (FIG. 10a), and the expression of TUJ1 and MAP2c proteins markedly increase on day 7 (FIGS. 10b, 10c). TUJ1 is an important protein marker of maturing neurons, and the TUJ1 immunostaing reveals clearly the maturation of neuronal cell morphology with clear perikaryon and neurite outgrowths. MAP2 is an exclusive dendritic protein in neurons. The smallest isoform of MAP2, MAP2c, is known to be involved in synaptogenesis, which is down regulated in the later stages of neuronal development. A higher level of TUJ1 proteins is found on the SiO$_2$ NZs than SiO$_2$ NHs, while more MAP2c expression is observed on the SiO$_2$ NHs than SiO$_2$ NZs. As MAP2c is an early neuronal marker and its expression decreases in mature neurons, it is shown that NSC differentiation occurs earlier on SiO$_2$ NZs than on SiO$_2$ NHs. The immunocytochemistry results are in a well agreement with the western blot results (FIGS. 7a, 8a and 9a). It is illustrated that, without any chemical GF, the SiO$_2$ ECnMs effectively induces the growth of neurospheres and stimulate the differentiation of NSC to neurons. The SiO$_2$ NZs exhibits neuronal cell maturation faster than the SiO$_2$ NHs.

Figure 12A:
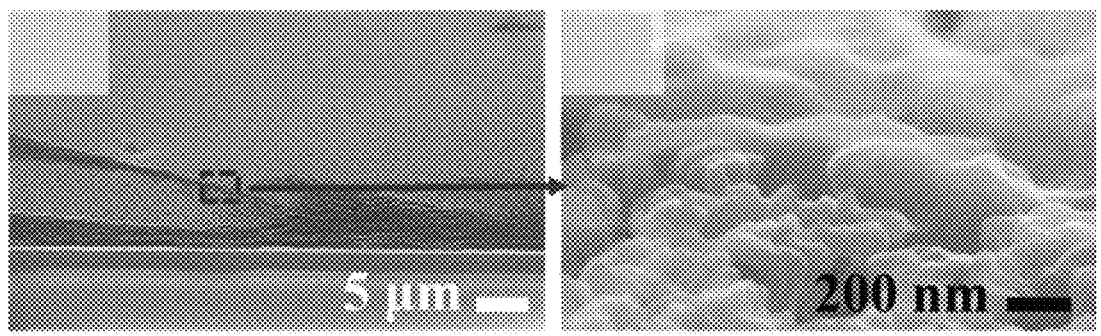
FIG. 12a shows cross-sectional SEM images of NSC differentiation on the $SiO_2$ NHs ECnMs, on day 7.
Figure 12B:
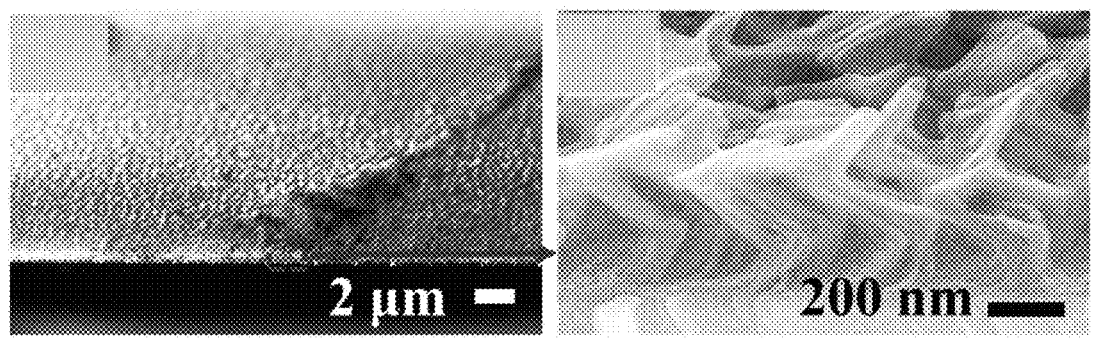
FIG. 12b shows cross-sectional SEM images of NSC differentiation on the $SiO_2$ NZs ECnMs, on day 7.

No chemical GF is used, so that only the effects of the physiological cues, topography and stiffness of different structure of SiO$_2$ ECnMs on NSC differentiation are considered. The interaction of the spreading neurons and the lower portion of the ECnM proximal to the substrate on which the ECnM is deposited was studied by SEM. The differentiated neuron cells strongly adhere to the SiO$_2$ NHs and NZs (FIGS. 12a-12b), consistent with the previous report that the cellular interaction with the two-dimensional ECMs happens on the base of the cells. The fibrillar focal contacts are formed to an extent that the spreading neuronal cells strongly wrap the upper portion of the SiO$_2$ ECnMs, indicating that the differentiated neuron cells can perceive different topographies of the NHs and NZs. The topography cues, including contact depth, geometrical profile of contacts, and cell adhesion area, will play an essential role in the NSC differentiation. The comparison of the SiO$_2$ NHs and NZs is made, with respect to the three topography cues. The contact depth, which is the distance NSCs make contact with the ECnMs, is roughly the half pitch of the NHs (i.e., ~120 nm, FIG. 12a) and the pitch of the NZs (i.e., ~160 nm, FIG. 12b) proximal to NSCs. It was reported that human mesenchymal stem cells on the 100-nm-depth patterns develop a higher level of cellular organization than on the 10-nm-depth patterns, eventually resulting in a differentiation into the osteoblast lineage. It is indicated that large contact depth, which the SiO$_2$ NZs have, facilitate the NSC differentiation. For the geometrical profile, the NHs have a helical profile and the NZs have a profile of tilted rod with a surface smoother than the NHs (FIG. 1b versus 1a). Furthermore, the NZ arrays appear to have disorder grooves at the neuron/ECnM contacts (inset of FIG. 2b), which is not observed on the helical ECnMs (inset of FIG. 2a). It is reported that the NSC differentiation is favored on nanopatterned substrates with grooves, consistent with the present invention. It may be ascribed to that more surface grooves can enhance focal adhesion and allow more physical contacts between the growing cell bodies and the ECnMs, especially when the neuritis expands to be embedded into the spaces in-between the zigzag nanostructures. To calculate the cell adhesion area, it is necessary to measure the surface density of the nanostructures in the ECnMs, which is prohibited by the blurry top-down view SEM images of the $SiO_2$ ECnMs owing to their low electric conductivity. Furthermore, stiffness of the ECnMs controls the eventual fate of the cell type, which are discussed below.

Figure 1F:
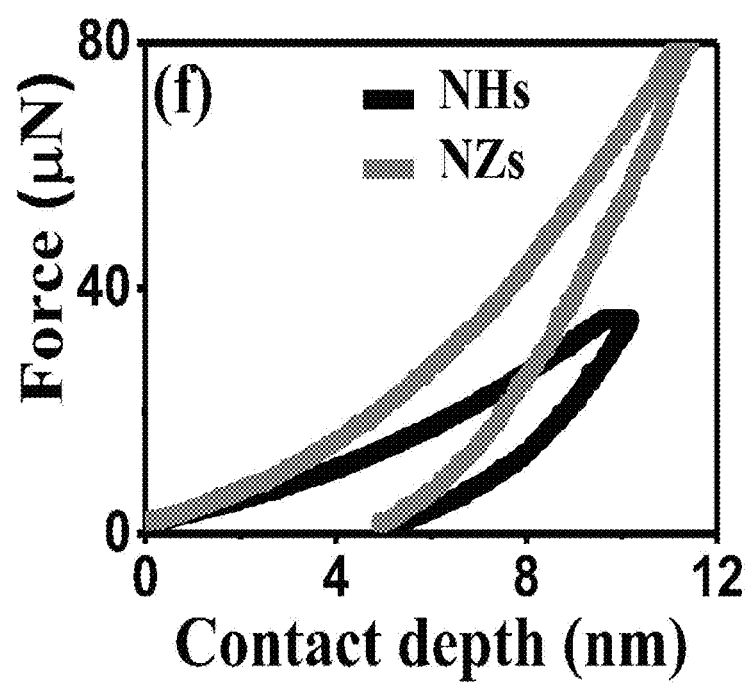
FIG. 1f shows nanoindentation plots of NHs and NZs of $SiO_2$ ECnM by GLAD.
Figure 13A:
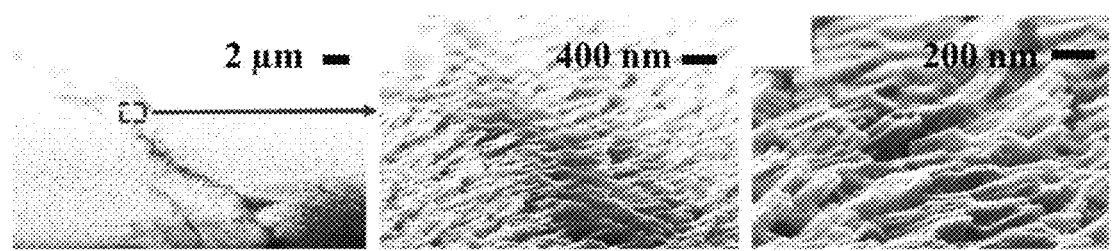
FIG. 13a shows cross-sectional SEM images of NSC differentiation on the $TiO_x$ NZs ECnMs, on day 7.
Figure 13B:
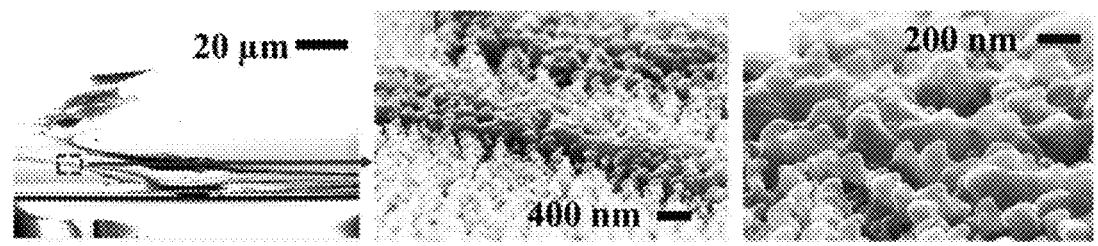
FIG. 13b shows cross-sectional SEM images of NSC differentiation on the $TiO_x$ NHs ECnMs, on day 7.
Figure 14:
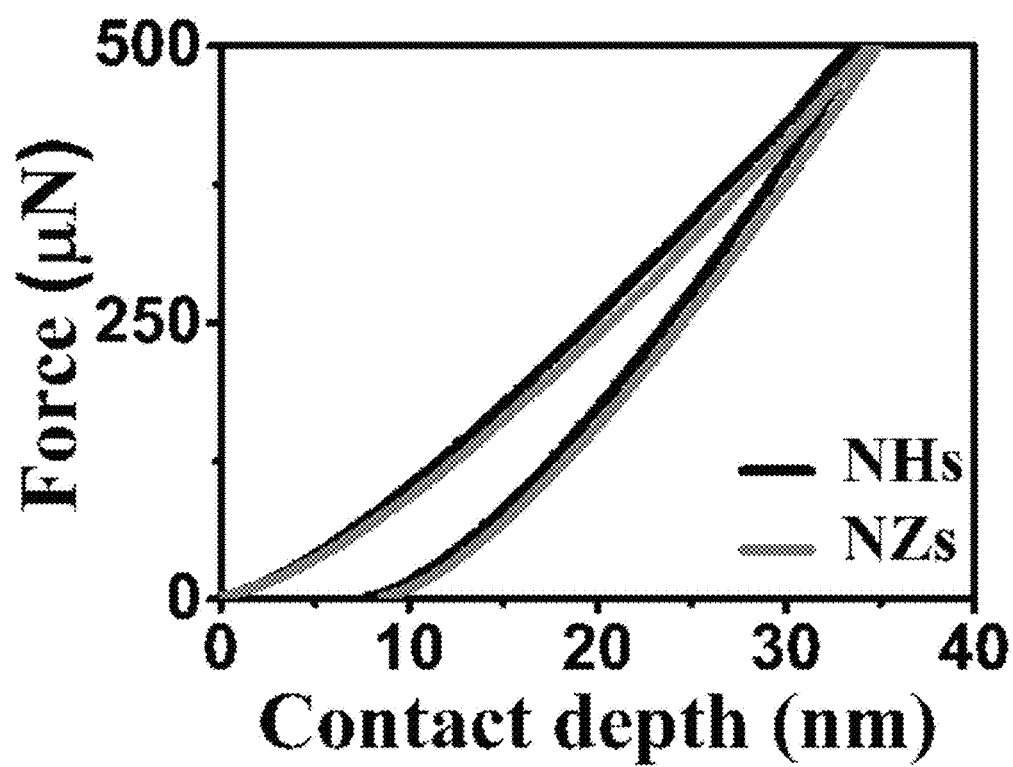
FIG. 14 shows nanoindentation plots of the $TiO_x$ ECnMs, in a shape of the helix or zigzag.

Although the $TiO_x$ ECnMs can induce the NSC proliferation and neurosphere growth (FIGS. 3b and 6), they tend not to promote the differentiation into neuron commitment, compared to the control group (FIGS. 7b, 10d-10f). The differentiated neuron cells adhere to the $TiO_x$ ECnMs in a way analogous to those on the $SiO_2$ ECnMs (FIG. 13a-13b). Given a shape of the helix or zigzag, the TiOx ECnMs have a nanostructure similar to that of the $SiO_2$ ECnMs (Table 1). It is indicated that the morphology cues could hardly account for a material-caused difference in the NSC differentiation on the inorganic ECnMs. The difference in degree of NSC differentiation attributes to the stiffness of the ECnMs, which is evaluated by nanoindentation. The $SiO_2$ NHs have a stiffness of 12.6±1.8 μN/nm, lower than 19.7±2.3 μN/nm for the $SiO_2$ NZs (FIG. 1f). The $TiO_x$ ECnMs have a shape-independent stiffness of ~26 μN/nm (FIG. 14), higher than the $SiO_2$ ECnMs. As discovered by the inventors, the stiffness of ECMs have a complex effect on cell commitment. For example, soft ECMs (below 10 μN/nm) favor the differentiation to pluripotent stem cells, and intermediate stiffness gels greatly favor the neuron commitment. A biphasic response for mesenchymal stem cell differentiation is observed to have the maximum level of osteogenesis at intermediate stiffness, which could account for the phenomena observed in this work. In a intermediate stiffness between 10-30 μN/nm, the neuron commitment is the most favored, corresponding to intermediate stiffness of ~20 μN/nm for $SiO_2$ NZs. The $SiO_2$NHs are too soft to strongly induce the neuron commitment. The TiOx ECnMs have such a high stiffness to prohibit the NSC differentiation; hence, $TiO_2$ isn't recommended for the GF-free NSC differentiation.

Without use of chemical GF, the $SiO_2$ ECnMs sculptured in the helix and zigzag by GLAD are employed to proliferate NSCs to form neurospheres and differentiate to neuron commitment in vitro. To the inventors' best knowledge, this is the first report on the realization of proliferation and differentiation of NSCs induced by ECnMs without chemical GF. The GF-free proliferation of NSCs tends to be faster than the GF-induced NSC growth. The sculptured shape has little effect on the NSC proliferation, but the zigzag structure is favored for the differentiation to neurons. Compared to the helix, the zigzag topography provides a larger contact depth and a large amount of grooves that lack in the helical to strongly enhance cell adhesion, and has an intermediate stiffness suitable for the neuron commitment. Although the sculptured ECnMs made of $TiO_x$ (0.33≤x≤2) can proliferate the growth of NSCs, they are too stiff to differentiate NSCs to neurons.

An embodiment of the present invention provides some profound impacts on the NSC proliferation and differentiation. First, the GF-free growth and differentiation of NSCs of the present invention significantly minimizes the risk of generating cancer cells in stem cell therapies. Second, the GLAD technique enables one to flexibly engineer material and structure of the sculptured ECnMs, opening a door to tailor cell fate by controlling the physiological cues of topography and stiffness of the ECnMs. Third, the GLAD technique offers a one-step-process production of the sculptured ECnMs in a large area (e.g., on a 4-inch wafer) with uniform structures. It paves the way to differentiate NSCs to the designable cell commitment with sufficient amount of differentiated cells, which is of urgent clinical demand for stem cell therapies.

Materials and Methodology

Nano-Matrixes

Inorganic nano-matrixes are deposited on surfaces by glancing angle deposition (GLAD), a special technique of physical vapor deposition. The deposition is operated at an incident angle of over 80 degree with respect to the substrate's surface normal, to generate the nano-matrix composed of an array of nanopillars of helices or zigzags. The materials of the nanopillars are those that can be physically evaporated, including, but not only limited to, dielectric materials (such as $SiO_x$ (FIGS. 1a-1f), $TiO_x$ (FIGS. 2a-2d), $Fe_xO_y$, $Ni_xO_y$, ITO), noble metals (such as Au, Ag), transition metals (Fe, Ni, Co), as well as their alloys and composites. The shape of the nanopillars is sculptured by controlling substrate rotation, including, but not only limited to, helices (FIG. 1a; FIGS. 2a and 2c), zigzag (FIG. 1b; FIGS. 2b and 2d), vertical posts, square spirals, and the combination of these structures in three-dimensional pattern. The nano-matrixes can be deposited on a wide range of substrates, including, but not only limited to, transparent (i.e., glasses), opaque (i.e. silicon wafers), electrically conductive (i.e., metals, ITO, ITO-coated glasses), and flexible (i.e., polymers) substrates.

GLAD of NHs and NZs:

In a custom-built physical vapor deposition system (Jun-Sun Tech Co. Ltd., Taiwan) with a high vacuum of $10^{-7}$-$10^{-6}$ Torr, $SiO_2$ (99.99%, Kurt J. Lesker company) and $TiO_2$ (99.9%, Kurt J. Lesker company) are evaporated at a rate of ~0.3 nm/s as monitored by a quartz crystal microbalance (QCM) located in the vicinity of a sample, using an electron-beam accelerating voltage of 8.0 kV and emission current of 83-87 mA. $SiO_2$ and $TiO_2$ are deposited at a deposition angle (α) of 87° and 86° with respect to the substrate's surface normal, respectively. The samples are deposited on ITO glasses (Xin Yan Technology Ltd.) and Si wafers (Semiconductor Wafer, Inc.), and the substrate temperature is controlled at room temperature using an ethanol/water cooling system. To produce left/right-handed NHs, the substrate is rotated counterclockwise/clockwise at a rate $R_r$ (in units of degree per second, or °/s) given by $$R_r = 360 R_d / P \quad (S1)$$

where $R_d$ is the deposition rate on the substrate surface calibrated as 0.28 nm/s for $SiO_2$ at α of 87° and 0.12 nm/s for $TiO_2$ at α of 86°. P is the helical pitch, as-designed to be ~200 nm. To produce the NZs, the substrate is stepped back and forth in 180° intervals, during which tilted nanorods are deposited with a given length (i.e., zigzag pitch). The structures of the ECnMs are summarized in Table 1.

Material Characterization:

The as-deposited samples are mechanically split, leaving the freshly exposed surfaces for the characterization of scanning electron microscopy (SEM, Oxford, LEO 1530). The NHs and NZs are scratched off the substrates and well dispersed in ethanol via ultra-sonication for 5 minutes. Several drops of the mixture are applied to a lacey carbon film on a grid structure (Electron Microscopy Sciences). The grid is dried in ambient and inspected by transmission electron microscopy (TEM, Tecnai G2 20 STWIN). Without post-deposition treatment, the samples are characterized by X-ray diffraction (XRD, Bruker, nonmonochromated Cu Kα x-ray with wavelength of 0.15418 nm, Advance D8 multipurpose x-ray diffractometer), X-ray photoelectron spectroscopy (XPS, Sengyang SKL-12, non-monochromatic Mg Kα radiation of 1253.6 eV, at a current of 15 mA, voltage of 10 kV and takeoff angle (between the sample and detector) of 90°, and in a vacuum of ~$2\times10^{-9}$ mbar), and nanoindentation (Nano Indenter XP, with a spherical tip having a 100 μm of radius of curvature).

Neural Stem Cell Isolation and Cell Culture

Rats (Springe Dawley) are purchased from the Chinese University of Hong Kong. NSCs are dissected from SVZ of P1 to P2 rats, and cultured at a cell density of $2\times10^5$ cells per well in 24-well plate and $1.0\times10^6$ cells per well in 6-well plate in NBM (Gibco) with 10% FBS (Gibco), 1% PSN (Gibco) and 2% B27 Supplement (Gibco). After 4-day and 7-day incubation at 37° C. in 5% $CO_2$ on the inorganic ECnMs, the localization, proliferation, levels of specific proteins and neurospheres are analyzed.

Cytotoxicity Assay:

NSCs are cultured on glass plates as the control group, and on the ECnMs in 4-well plates in 1 ml complete medium per well, followed by the incubation for 4 and 7 days. The MTT assay is performed at day 4 and 7. MTT solution is added and placed into an incubator at 37° C. for 4 hours in dark. Then DMSO is added in the MTT solution to dissolve the dark purple crystals. The optical density of the solution is measured by a spectrophotometer at a wavelength of 570 nm.

Immunocytochemistry Assay:

NSCs in cultures are first stained with nuclear stain, DAPI (1 μg/ml) in 100% methanol for 15 minutes in dark in the incubator at 37° C., without irradiation. Then the cells are then rinsed (1×60% methanol) and are then fixed with 4% paraformaldehyde (PFA) for 30 minutes at room temperature in dark. The cells are then further incubated with specific primary antibody solutions in PBS with Triton and normal goat serum overnight, at 4° C. in dark. The cells are rinsed with PBS and then incubated with specific secondary antibody solutions in PBS for 3 hours at room temperature. After rinsed with PBS, the cells are mounted with fluorescence mounting medium (Dako). Immunoreactivity for the cells is imaged by confocal microscope (FluoView FV1000, Olympus).

Western Blotting Analysis:

Western blotting is employed to compare the levels of Nestin, TUJ1 and MAP2c proteins in NSCs growing on the ECnMs. Proteins are extracted in protein extraction reagent (Novagen) supplemented with Protease Inhibitor Cocktail (Calbiochem). Protein concentration is measured using the Bio-Rad protein assay kit (Bio-Rad). Total proteins (30 μg) per sample are separated on 10% SDS-polyacrylamide gels and transferred to a polyvinylidene difluoride (PVDF) membrane. The Membrane is probed with anti-Nestin antibodies (Millipore, 1:1000), anti-TUJ1 antibodies (Millipore, 1:1000), or anti-MAP2c antibodies (Millipore, 1:1000), followed by an incubation with secondary antibody conjugated with HR. β-actin antibodies (Sigma, 1:5000) is used as a reference to assess the relative amounts of proteins loaded per lane. Images of bands are captured using gel documentation system (Bio-Rad).

Statistical Analysis:

Quantitative results are expressed as mean±Data of NSC proliferation and differentiation are analyzed by one-way analysis of variance in SPSS, and multiple measurements are operated to evaluate algebraic average value and standard deviation. All analyses are made using GraphPad Prism 5.0. Statistical significance was defined as $p<0.05$.

Lysis of Cells in Culture

In cell cultures, all medium from the culture is removed and the cells are rinsed with ice-cold phosphate-buffered saline (3× PBS). Lysis buffer is added to each well and cells are scrapped by rubber scrappers on ice. The cell lysates are then collected and centrifuged at 11,000g for 30 min at 4° C. The supernatants are collected in an Eppendorf tube for subsequence experiments.

Determination of Protein Concentrations

Prior to gel electrophoresis, protein concentrations are measured (Bio-Rad protein assay kit). The samples are diluted 10 folds with MiliQ water and 5 ul of samples are loaded to 96-well plate with adding of 25 ul of Reagent A and 200 ul Reagent B. The plate is then incubated in dark for 30 min at room temperature. Total protein concentration was measured as the optical density at 750 nm by a spectrophotometer.

Gel Electrophoresis (SDS-PAGE)

Equal concentrations of protein from each experimental group are employed. The protein samples are first denatured at 100° C. for 5 min with SDS before gel electrophoresis. Samples are mixed with electrophoresis buffer and then are loaded in gel. Electrophoresis is started using 30V for about 30 minutes and then with 70V for about 3 hours at room temperature.

Protein Blotting

After the completion of separation of proteins using gel electrophoresis, the proteins on the gel are transferred to polyvinylidene difluoride membranes overnight at 15V in transfer buffer.

Western Blotting

After incubation with specific antibodies, the membranes are washed with tris-buffered saline with tween 20 (TBST; 2×10 min), then with TBS (1×10 min). Protein bands are visualized with chemiluminescence detection reagent WESTSAVE Up. Images of bands are captured using gel documentation system (Bio-Rad).

There are four main features in this invention:

I. Nano-Matrixes are Non-Toxic to Cells in Culture

Figure 4:
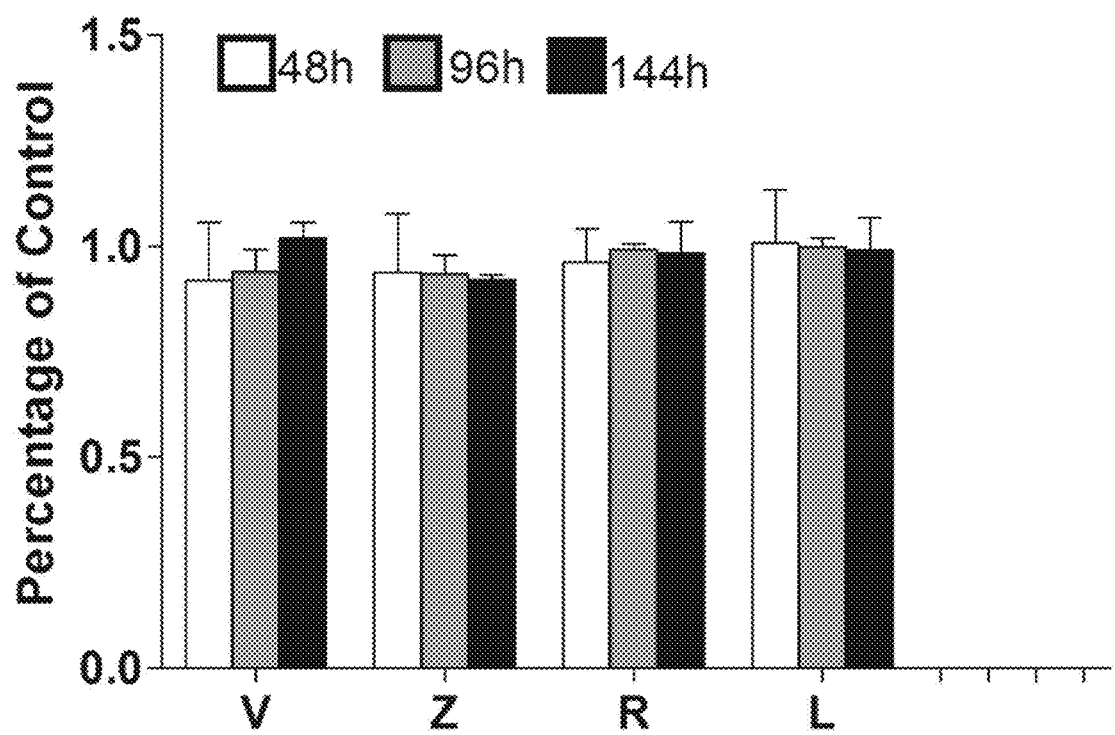
FIG. 4 shows the cell viability of neuronal cell SH-SY5Y on different nano-matrix.

Results of the MTT assays have shown that nano-matrixes of TiOx and $SiO_2$ do not affect the cell viability of both NSC (FIGS. 3a and 3b) and SY-SH5Y cells (FIG. 4). The nano-matrixes are therefore non-toxic.

II. Physical Substrates of the Nano-Matrixes can Promote Cell Proliferation of Neural Stem Cells into Neurospheres The presented data indicate that no additional growth factors (GF) or other chemical factor is required in inducing the growth of neurospheres from NSCs (FIG. 5 and FIG. 6). In conventional NSCs culture method, "neurosphere assay", differentiated cells die within a few days and therefore a small group of undifferentiated cells can proliferate actively in respond to epidermal growth factors (EGF) and basic fibroblastic growth factor (bFGF) to form into neurosphere. In conventional NSCs culturing, the growth of cells is highly dependent on the use of growth factors. If no growth factors are added, the cells will die. However, growth factors are very potent in regulating cell-signaling pathways. If high amount of growth factors is used to induce the differentiation of stem cells in vitro, it poses a risk of developing cancer cells in vitro or tumors in vivo after transplantation. For example, fibroblast growth factor (FGF) signaling, that is crucial for proliferation, survival and migration, has been shown to play an oncogenic role in many cancers. Moreover, vascular epidermal growth factors (VEGF), an inducer of angiogenesis, and that deregulated insulin growth factor (IGF) are related to the initiation and progression of cancer.

The inventors show for the first time achieving cell proliferation and differentiation on nano-matrixes without the addition of chemical growth factors (FIG. 5 and FIG. 6). As early as at day 4, clear neurospheres with diameters around 50 μm are achieved. The proliferation of NSCs that grow on nano-matrixes is found to be much enhanced than those found in the controls (FIG. 5 and FIG. 6).

The present nano-matrix comprises material selected from $SiO_2$ or TiOx. The present nano-matrix can initiate cell proliferation for the formation of the neurospheres. $SiO_2$ has much stronger effect in promoting the cell proliferation in formation of neurospheres (FIG. 5). From those different $SiO_2$ structures studies, $SiO_2$ Zigzag structures are found to be the best structure in generation of neurospheres (FIG. 5). TiOx Zigzag structures are in general found to be comparable to the SiOx structures, whereas TiOx Spiral structures are less effective in causing cell proliferation (FIG. 6). These differences in cell proliferation attributes at least partly to the differences in stiffness of the materials.

III. Maturation of Neurons from Neural Stem Cells can be Accelerated by the Nano-Matrixes Formation of neurospheres is the first step for cell differentiation and neuronal cell maturation. These are crucial steps for neuro-repair and cell replacement therapy for diseases in the brain. Quicker cell maturation can result in quicker transplantation and can shorten the time window for putting NSCs in culture, a procedure with high medical and contamination risks for patients. The results shows that a swift neuronal cell maturation can be achieved by using the present nano-matrixes without using chemical growth factors (FIGS. 7a-7b, 8a-8b, 9a-9b).

Figure 7B:
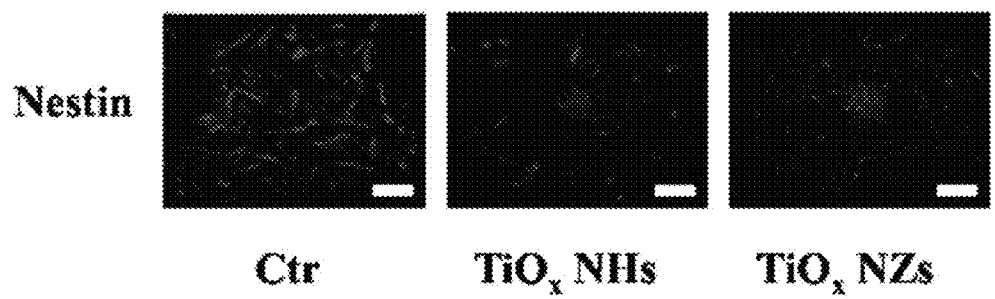
FIG. 7b shows fluorescence images of Nestin in NSC cultured on $TiO_x$ ECnMs in a shape of the helix (NHs) or zigzag (NZs). Scale bar: 50 μm.

Both $SiO_2$ and TiOx nano-matrixes of the present invention promote the expression of nestin, a fibrillary protein that is related to stemness of NSCs and is a marker for NSCs. These results at day 4, NSCs are activated by the nano-matrixes to promote growth and to start the cell maturation processes (FIGS. 7a-7b).

Figure 8B:
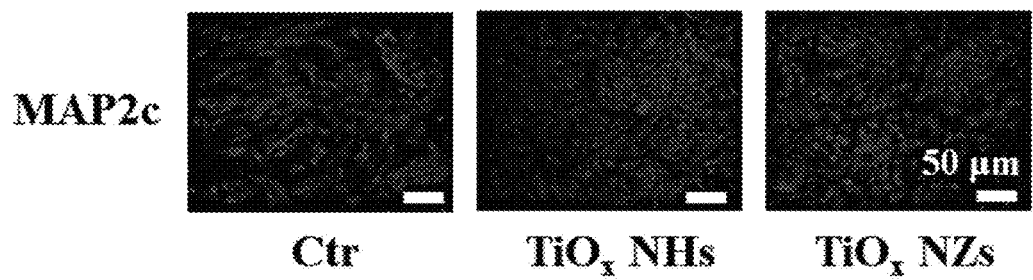
FIG. 8b shows fluorescence images of MAP2c in NSC cultured on the $TiO_x$ ECnMs in a shape of the helix (NHs) or zigzag (NZs). Scale bar: 50 μm.

There are also continuous rise of MAP-2 protein levels in NSCs growing on the nano-matrixes (FIGS. 8a-8b and FIG. 10c). MAP-2 is an exclusive dendritic protein in neurons. These indicate there are increases in synthesis of dendritic proteins with the contacts on the nano-matrixes. $SiO_2$ structures are found to perform better in promoting the growth of dendrites.

Figure 9B:
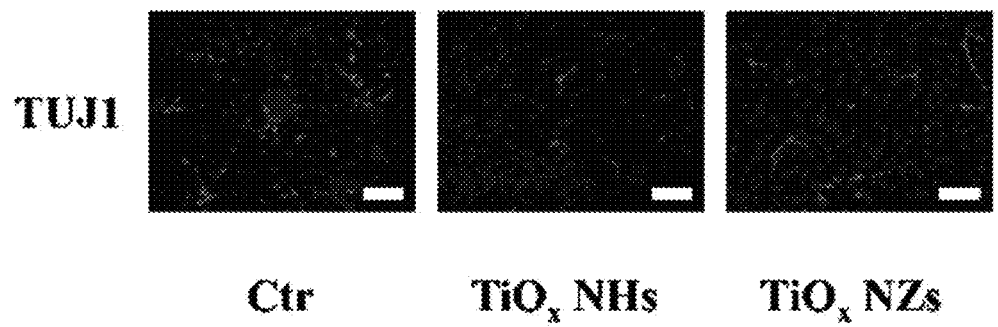
FIG. 9b shows fluorescence images of TUJ1 in NSC cultured on the $TiO_x$ ECnMs in a shape of the helix (NHs) or zigzag (NZs). Scale bar: 50 μm.

Similar to MAP-2 proteins, TUJ-1 is also an important protein marker for maturing neurons. TUJ-1 immunostaing can reveal clearly the maturation of neuronal cell morphology with clear perikaryon and neurite outgrowths. In terms of cell maturation towards neurons, among the two materials tested, $SiO_2$ is a better material for achieving this purpose (FIG. 9a). A much higher number of TUJ-1-immunopositive maturing neurons are found after incubating on $SiO_2$ ZigZag nano-matrixes (FIG. 9b). These results are also strongly supported by Western blotting analysis (FIG. 10b). Similar to the cell proliferation effects, the differences in effectiveness causing neuronal cell maturation may also be at least partly due to the stiffness of the materials.

IV. Nanotopography is Crucial for Cell Differentiation

Nanostructure, the shapes, of the material on the matrixes is a key factor that affects the proliferation and differentiation of NSCs. More and more evidences have shown that the cells can "fell" the topographies of matrixes from nanometer to micrometer scale, as the topography can induce pronounced changes in the pattern of focal adhesion structure, influencing the cytoskeleton and consequently gene expression. As a result, the topographical information could mediate stem cell differentiation and proliferation. The cells preferentially differentiate into neurons on top of one of the matrixes. In general, zigzag structures are found to be more effective than the other structures in promotion of cell proliferation and cell differentiation of NSCs (FIGS. 5 to 9b). These observations maybe due to the fact that there are more "grooves" and nanospaces in the zigzag structures that can allow more physical contacts between the growing cell bodies and neurites of the NSCs especially when the neurites are extending then embedded into the space in between the zigzag structures.

Pure mechanical support is provided to cells and material itself shows no effects on cells viability. In natural environment, cells respond to its surroundings by interacting with extracellular matrix (ECM) in a nanometer scale. Topography of extracellular can influence cell attachment, migration, proliferation as well as differentiation. As a result, an increasing attention has been focused on the nanotopography for its resemblance to the in vitro environment.

Conclusion

The present invention provides a "growth factor free" physical nanostructure that promotes cell proliferation, cell differentiation and maturation of NSCs in culture. The invention will form an important step in achieving safe and cost-effective mean of cell maturation process in future possible clinical applications of cell processing technology for cell therapies of diseases in the brain.

Further Development of the Present Invention

There is a demand in proliferating and differentiating neural stem cells (NSCs) to functional neurons with no risk of carcinogenicity for use in stem cell therapies in treating neurodegenerative diseases—a main threat and burden to global aging healthcare. Herein, the inventors demonstrate, for the first time, that such urgent clinical demand can be fulfilled by employing biocompatible silica extracellular nanomatrices, sculptured in zigzag by glancing angle deposition. The present invention provides nanostructure comprises nanozigzags of silica ($SiO_2$). The nanozigzags form a nanomatrix that promotes the differentiation of neural stem cells to functional neurons. The present invention also provides nanostructure embedded with differentiated neurons. The present nanostructure embedded with differentiated neurons are capable for transplantation for treatment of neurodegenerative disease (e.g. Parkinson's disease). In one embodiment, the present invention provides a substantia nigra organoid on a nanostructure. An organoid referred herein is a miniaturize version of an organ produced in vitro. The substantia nigra organoid on the nanostructure is used to treat neurodegenerative disease, such as Parkinson's disease. The zigzag silica extracellular nanomatrices (iSECnMs) of the present invention mediate NSC specific differentiation and forms an organoid of Substantia nigra (mini-SN) in the absence of neurogenic chemical growth factors. The present invention provides elongation of the zigzag pitch in a range of 100-250 nm which favors NSC proliferation, and swift differentiation to functional neurons through the Wnt/β-catenin signaling pathway, and prohibits the unwanted differentiation into non-neuronal cells (such as astrocytes and oligodendrocytes). In one embodiment, the pitch of the nanozigzag is 80 nm-250 nm. In one embodiment, the pitch of the nanozizag is 80 nm, 170 nm or 225 nm. In another embodiment, the contact depth of the zigzag is 90 nm to 260 nm. In another embodiment, the contact depth is 100 nm to 255 nm. The mediation of NSC specific differentiation of the present nanomatrix is ascribed to physiological cues of the silica nanozigzags, including contact depth, groove-like topography and stiffness. The differentiated neurons on the nanostructure of the present invention are shown to survive after transplantation, retain neuronal characteristics, migrate to the cortexes in vivo, and then form functional connections in the brain. The present extracellular nanomatrices are highly flexible for nanostructural engineering. The present extracellular nanomatrices facilitate the differentiation of stem cells to designable cell commitment with sufficient cell amount-highly desired by clinical stem cell therapies. The present invention provides method of forming substantia nigra organoids with silica iSECnMs. The iSECnMs have a zig-zag conformation. The present invention also provides use of the substantia nigra oragnoids on silica iSECnMs for cell therapies.

Brain organoids are functional aggregations of neurons in vitro. Brain organoid technology has been achieved by various labs but yet there is no regional specific brain organoids produced so far. In addition, chemical and genetic manipulations are essential for formation of these organoids and the existing in vitro produced brain organoids have minimal resemblances to in vivo conditions. Substantia nigra (SN) is a region of interests as it is the center of degeneration of dopaminergic (DA) neurons in Parkinson's disease (PD). Cell therapies such as reparative regeneration and cell replacement of DA neurons in the SN can be used to treat PD. Therefore, organoid of SN (mini-SN) on nano-structure of the present invention is useful in cell therapies.

The neurons of SN are mostly dopaminergic and GABAergic cells with a small portion of glutamatergic. The inventors develop an approach to create miniature organoid of SN (mini-SN) with silica iSECnMs, especially the zig-zag conformations of the nanomatrix (NZs), which can induce NSCs to differentiate into dopaminergic and GABAergic but suppress glutamatergic neurons without the need of specific growth factors (GFs). This mini-organoids can be used for neural differentiation in vitro to simulate neurons in SN, drug screening or ultimately designed as a replacement or temporary organ of SN for PD treatment. In addition, the present SN organoid in zigzag silica nanoma-trix can be used in cell replacement therapy for PD is substantially limited by the lack of self-renewal and specific differentiation of NSCs to DA neurons without the presence of growth factors. Growth factors (GFs) lead to a high risk of carcinogenesis in vivo after transplantation. For example, it was reported that sonic Hedgehog (SHH), a GF for the NSC differentiation to DA neurons, is closely related to tumorigenesis. US Food and Drug Administration (FDA) regulates that biomedical materials used in clinical cell processing must be xeno-free, while GFs are regarded as a xeno-origin. There is an urgent clinical demand on developing a novel mini-organoid of SN for specific differentiation of NSCs in vitro without the use of GFs or additives. The present application provides mini-organoid of SN formed from specific differentiation of NSCs in vitro without the use of growth factors and method of making the mini-organoid of SN.

Currently, NSC in vitro induction is done by extracellular matrices (ECMs) made of organic scaffolds, such as poly-L-ornithine (PLO) and poly-L-Lysine (PLL), which might enhance the likelihood of host inflammatory responses. There exists a wide range of biocompatible/biodecomposable extracellular nanomatrices (ECnMs) for instructing in vitro fate of stem cells in the presence of biochemical and physiological cues. The biochemical cues are mainly GFs. Stem cell culture microenvironment of ECMs/ECnMs is susceptible to multiple physiological cues, such as nature of materials, stiffness, and topography. An increasing attention has been focused on the nano-topography due to its resemblance to in vivo bio environment. However, most studies were unavoidably carried out in the presence of GFs for specific differentiated induction. The present application provides biomaterials for NSCs culturing and specific differentiation without addition of GFs. The rigidity and topography of ECnMs enables one to encode instructions in ECnMs to develop specialized cellular commitment and functions.

Herein, the present biocompatible inorganic sculptured ECnMs (iSECnMs) of silica nanozigzags are deposited by glancing angle deposition (GLAD), to achieve induction of specific differentiation without growth factors. The iSECnMs are made from silica due to its biocompatible nature, natural abundance, and low cost; and they are sculptured to have engineerable topographies and stiffness, which are the two significant physiological cues. To separately study these two physiological cues, at a given height (H) of silica iSECnMs that substantially determines its stiffness, the iSECnMs were sculptured in helical and zigzag conformations to investigate the topography cue. In culture having no neurogenic chemical growth factors, the silica iSECnMs function as a biomedical device to proliferate the growth of NSCs, and NSCs can be differentiated to neuronal commitment through the Wnt/β-catenin signaling pathway, it is shown that the zigzag conformation mediates a better NSC differentiation than the helical ones. Then to study the physiological contribution from the iSECnM stiffness, the NSC proliferation and differentiation were mediated on the zigzag as a function of height (H) of iSECnM. Transplant of the differentiated neurons into the cortex of rats were performed to study the neuron survivability. Transplant of the differentiated neurons from the iSECnM of the present invention is demonstrated to provide an in vitro culture in the absence of neurogenic chemical growth factors for NSC therapies. The transplant of the present invention is shown to have minimal carcinogenicity, a controllable differentiated cell lineage-aligning well with the clinic regulatory guidelines.

Figure 15A:
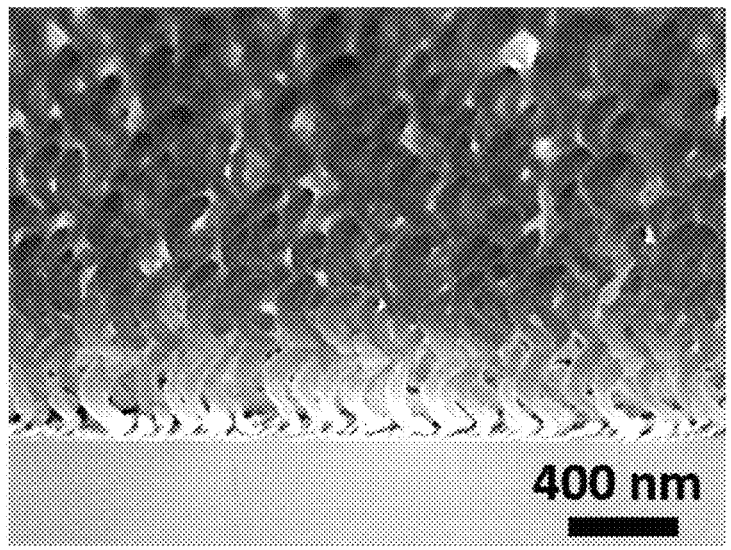
FIG. 15a shows GLAD of the silica iSECnMs sculptured in a helical shape. Cross-sectional SEM images of NHs with a helical pitch (P) of ~245 nm. (scale bar: 400 nm)
Figure 15B:
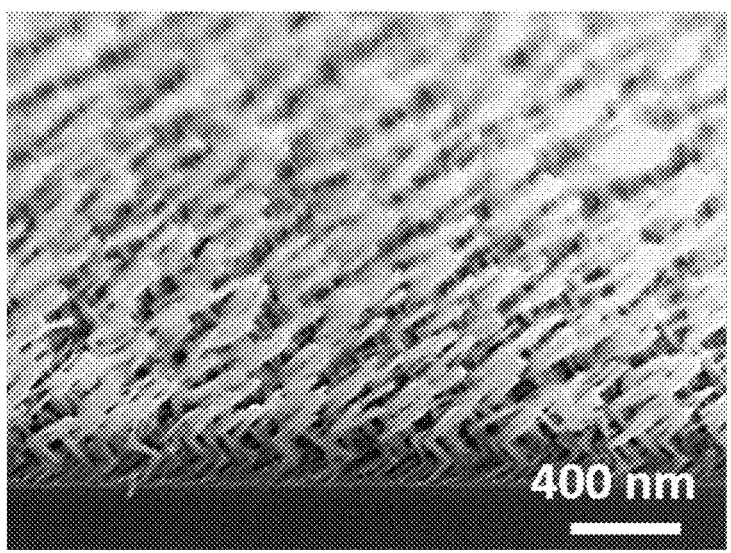
FIG. 15b shows GLAD of the silica iSECnMs sculptured in zigzag. Cross-sectional SEM images of NZs with the P of ~80 nm. (scale bar: 400 nm)
Figure 15C:
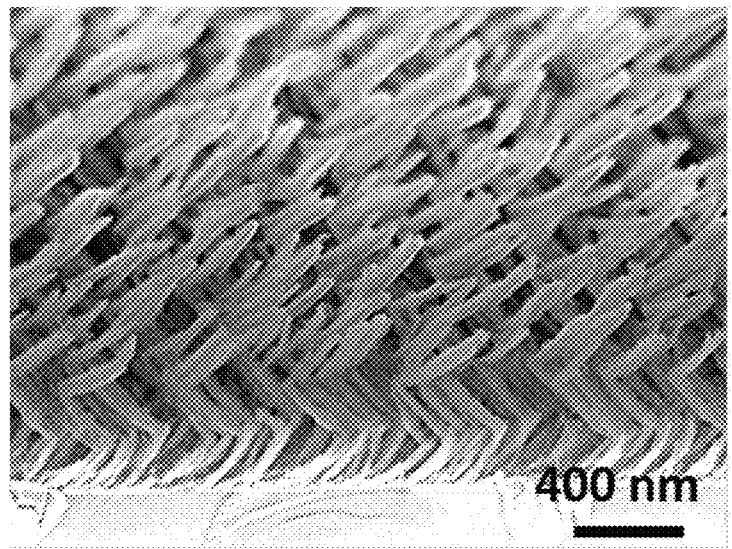
FIG. 15c shows GLAD of the silica iSECnMs sculptured in zigzag. Cross-sectional SEM images of NZs with the P of ~170 nm. (scale bar: 400 nm)
Figure 15D:
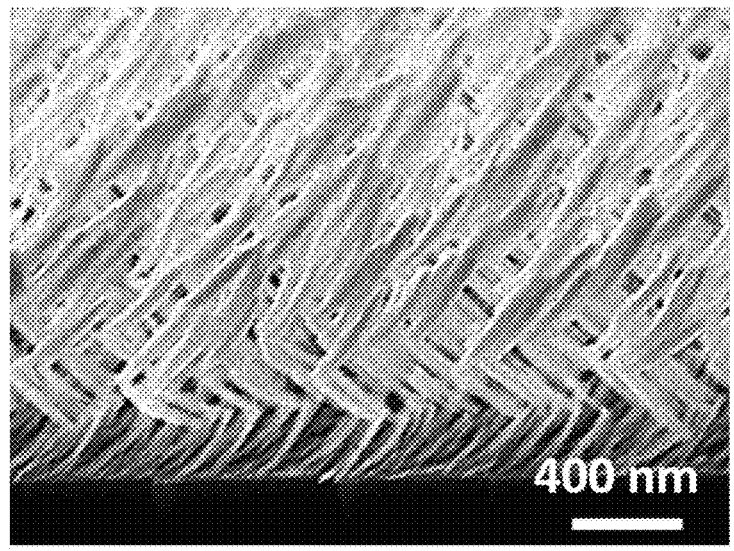
FIG. 15d shows GLAD of the silica iSECnMs sculptured in zigzag. Cross-sectional SEM images of NZs with the P of ~225 nm. (scale bar: 400 nm)
Figure 15E:
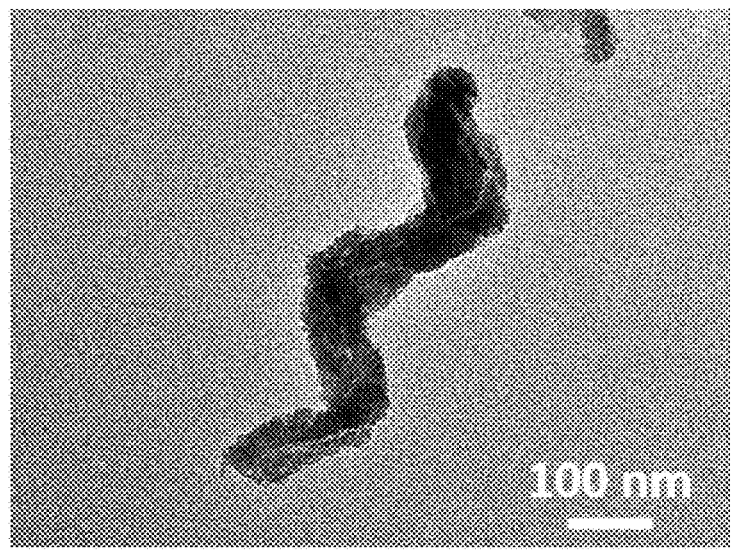
FIG. 15e shows TEM images of individual nanostructures of NHs.
Figure 15F:
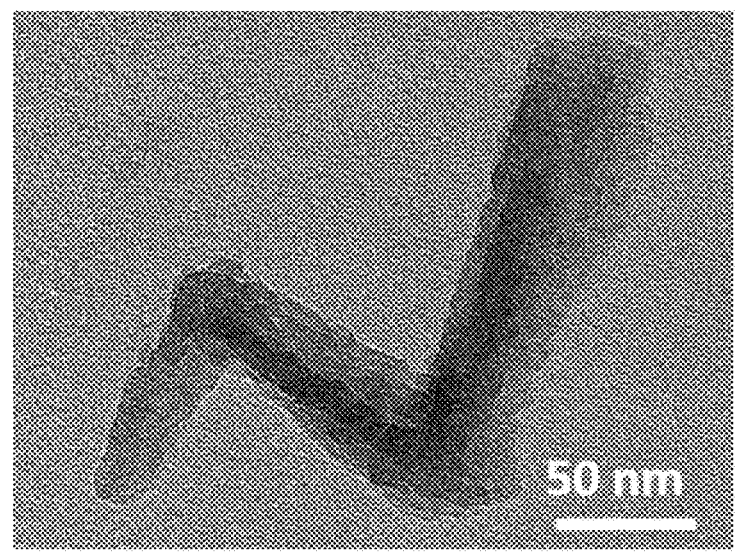
FIG. 15f shows TEM images of individual nanostructures of NZs with the P of ~80 nm.
Figure 15G:
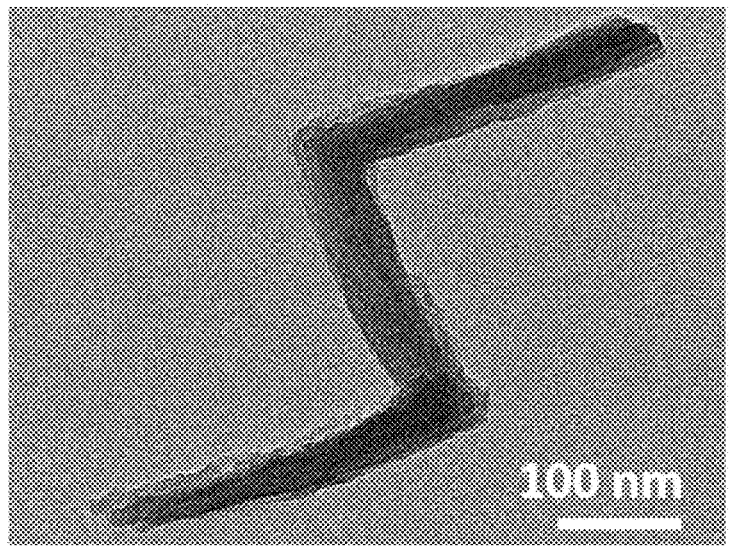
FIG. 15g shows TEM images of individual nanostructures of NZs with the P of ~170 nm.
Figure 15H:
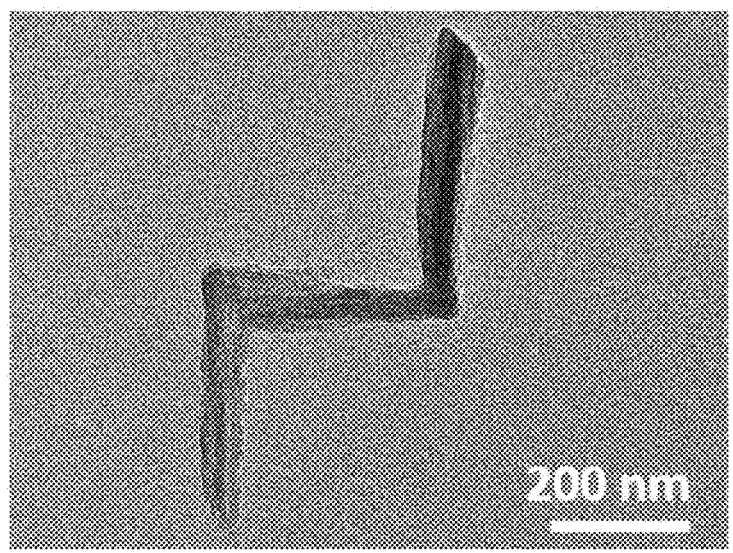
FIG. 15h shows TEM images of individual nanostructures of NZs with the P of ~225 nm.
Figure 15I:
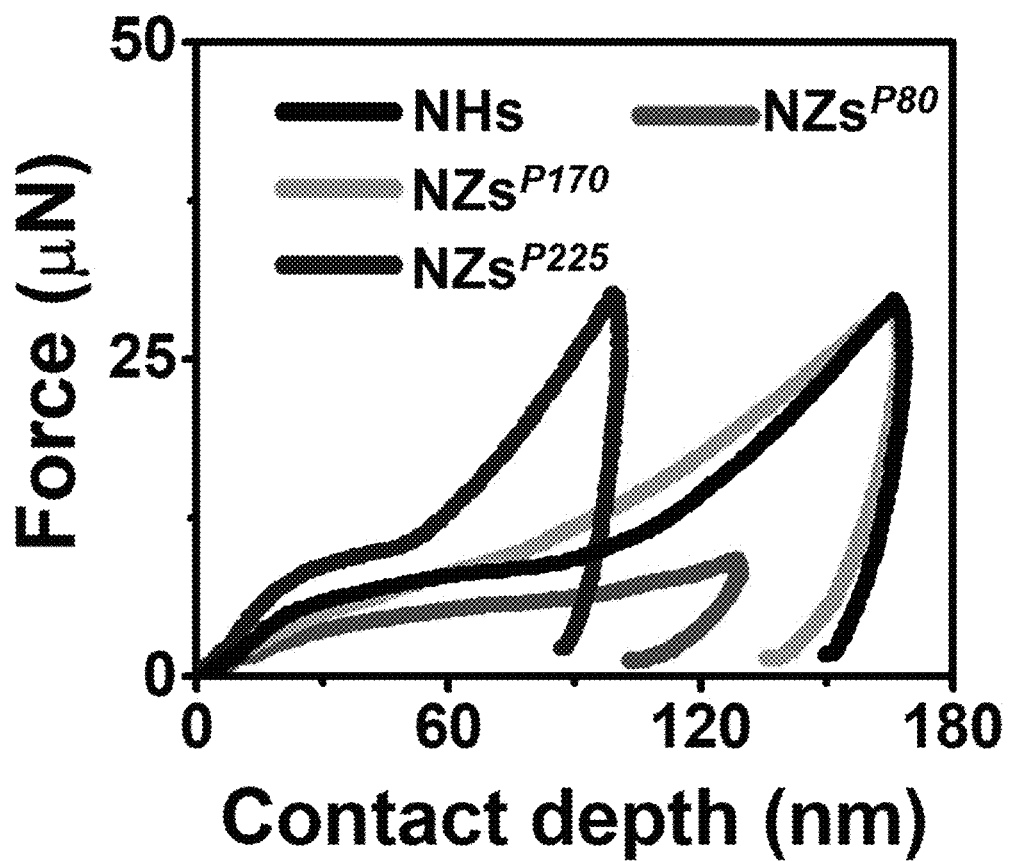
FIG. 15i shows Nanoindentation plots of the L-NHs (black line), and the NZs with a PZ of ~80 nm (red line), ~170 nm (green line) and ~225 nm (blue line).

Given no neurogenic chemical growth factors is used, it is evident that the physiological cues, including topography and stiffness of silica iSECnMs, play an essential role in the iSECnM mediation. The topography and stiffness primarily depend on the structure of the iSECnMs, which can be flexibly engineered by GLAD. Therefore, silica iSECnMs are sculptured in, e.g., helical (i.e., nanohelices or NHs, FIG. 15a) and zigzag (i.e., nanozigzags or NZs, FIGS. 15b-15d) conformations. The structural parameters of the silica iSECnMs, including height (H), wire diameter (d), helical pitch (PH), zigzag pitch (PZ), number of pitch (n) in FIGS. 15a (a-II) to 15d (c-II), are summarized in Table 2. The surface of the NHs appears to be rougher than that of the NZs (FIG. 15a (a-II) versus FIGS. 15b (b-II), 15c (c-II) and 15d (d-II). Typically, the NZs have a groove-like topography due to the GLAD-induced anisotropic growth of the NZs, markedly different from the NHs that exhibit a helical topography. The stiffness of the silica iSECnMs was measured by atomic force microscopy (FIG. 15e), revealing that the NHs with a H of ~540 nm and n of 2 have a Young's modulus is comparable to that of the NZs having a H of ~550 nm and n of 3, and the stiffness of the three-pitch NZs tends to increase with an increase of PZ. Given the similar stiffness and distinct topography, the silica NHs (having a H of ~540 nm and n of 2) and the NZs (with a H of ~550 nm and n of 3) were selected to mediate the NSC proliferation and differentiation.

TABLE 2

Summary of the sculptured structures (in terms of height (H), helical/zigzag pitch (P), number of pitch (n), and wire diameter (d) in the top portions of the iSECnMs) and mechanical properties (in terms of Young's modulus) of the iSECnMs made of silica and $TiO_x$. For the structural evaluation, multiple (not less than 10) measurements for each sample were operated to evaluate algebraic average value and standard deviation. Contact depth ($d_c$) of the cells is evaluated by $d_c = (P + d)/2$ for the NHs, and $d_c = P + d/2$ for the NZs. For the evaluation of Young's modulus by nanoindentation, the iSECnMs were deposited on a silicon wafer and six points over the surface of each sample were measured for statistical evaluation.

| iSECnMs | | FIG | H (nm) | n | d (nm) | P = (H − d)/n (nm) | Contact depth $d_c$ (nm) | Young's modulus (Gpa) |
|---|---|---|---|---|---|---|---|---|
| Silica | NHs | 15a | 538 ± 4 | 2 | 48 ± 2 | 245 ± 4 | 146 ± 4 | 3.20 ± 0.24 |
| | $NZs^{P80}$ | 15b | 279 ± 7 | 3 | 38 ± 2 | 80 ± 7 | 99 ± 7 | 0.62 ± 0.08 |
| | $NZs^{P170}$ | 15c | 553 ± 3 | 3 | 46 ± 3 | 169 ± 4 | 192 ± 4 | 2.04 ± 0.22 |
| | $NZs^{P225}$ | 15d | 733 ± 7 | 3 | 64 ± 4 | 223 ± 8 | 255 ± 8 | 7.85 ± 1.39 |

Figure 16A:
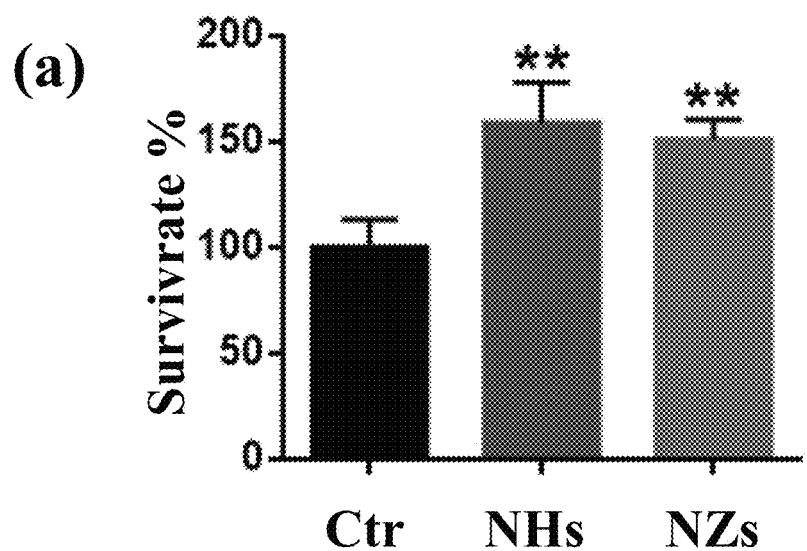
FIG. 16a shows proliferation and neural differentiation of NSCs mediated by the silica iSECnMs. The survival rate of NSCs mediated by iSECnMs is monitored in culture on day 7. **$p<0.01$, compared with the control group (i.e., Ctr).
Figure 16B:
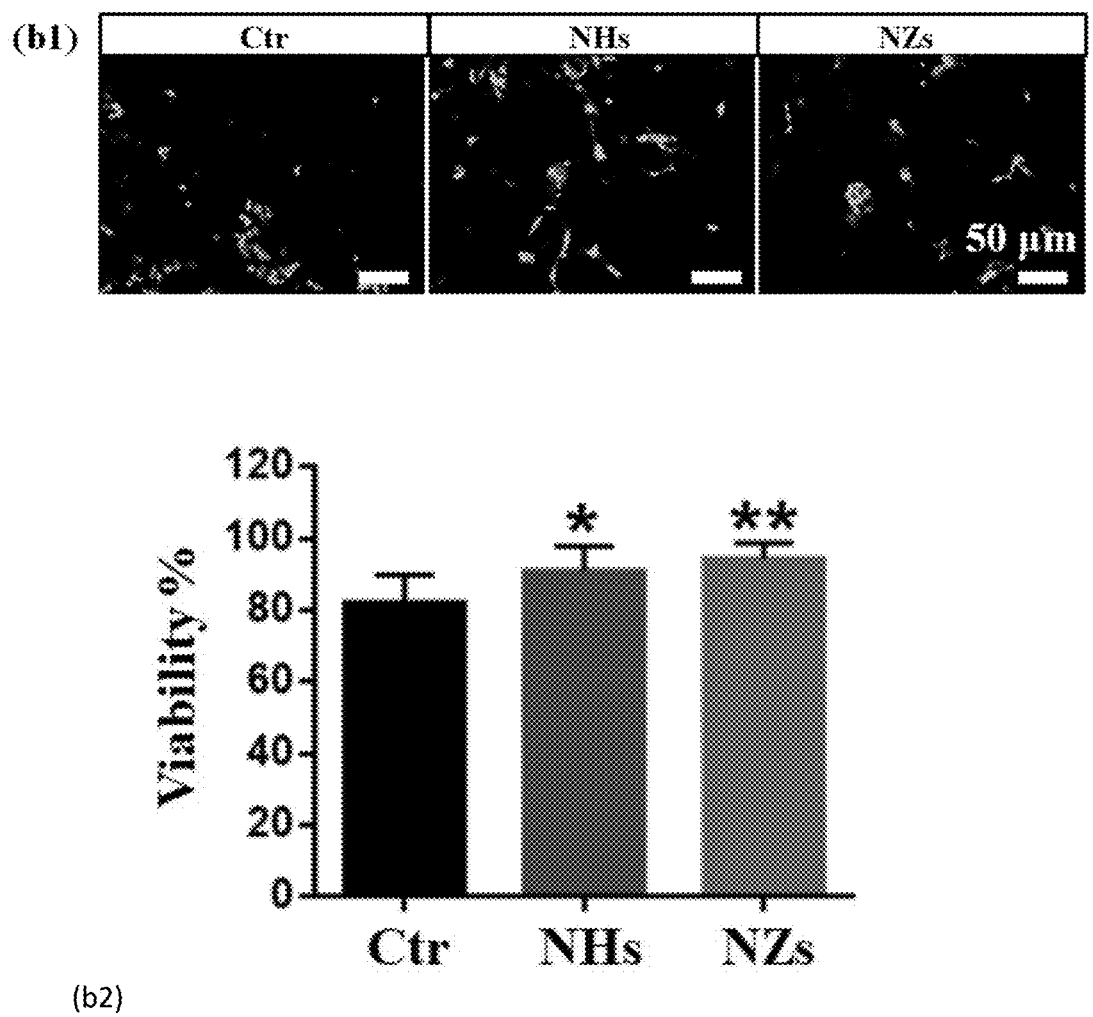
FIG. 16b shows proliferation and neural differentiation of NSCs mediated by the silica iSECnMs. Fluorescent staining (b1) to characterize the cell viability of the NSCs grown on the iSECnMs (scale bar: 50 μm). Living and dead cells are stained in green and red, respectively. The bar charts (b2) represent the cell viability. *$p<0.05$, **$p<0.01$ compared with the control group.

In vitro proliferation and differentiation of NSCs mediated by the silica iSECnMs were operated in the neurobasal medium containing fetal bovin serum (FBS) to retain the health states of the isolated NSCs in culture. The NSC proliferation was characterized by MTT and live/dead assay on the $7^{th}$ day in culture (i.e., day 7). The survival rate of NSCs on the NHs and NZs are similar and are both evidently superior to the control group, determined by MTT assay (FIG. 16a). The mediation of the iSECnMs leads to the cell vitality, monitored by live/dead assay, more than that on the control group; the cell viability on the NZs is larger than that on the NHs (FIG. 16b). It is shown that the iSECnMs can promote the proliferation and viability of NSCs.

Figure 16C:
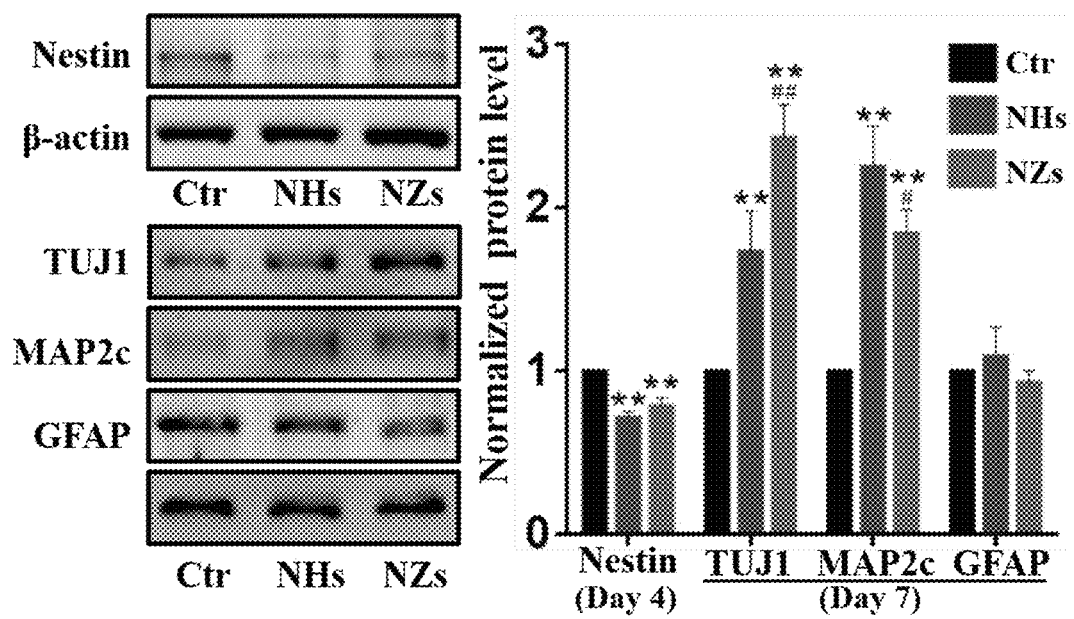
FIG. 16c shows proliferation and neural differentiation of NSCs mediated by the silica iSECnMs. Differentiation of NSCs on the silica iSECnMs of L-NHs and NZs for day 4 and day 7 was monitored by western blot analysis. Western blot analysis and statistical evaluation of the expression of diverse marker proteins: Nestin (day 4), TUJ1 (day 7), MAP2c (day 7), GFAP (day 7). **$p<0.01$ compared with the control group; #$p<0.05$, and ##$p<0.01$ compared with the L-NHs.
Figure 16D:
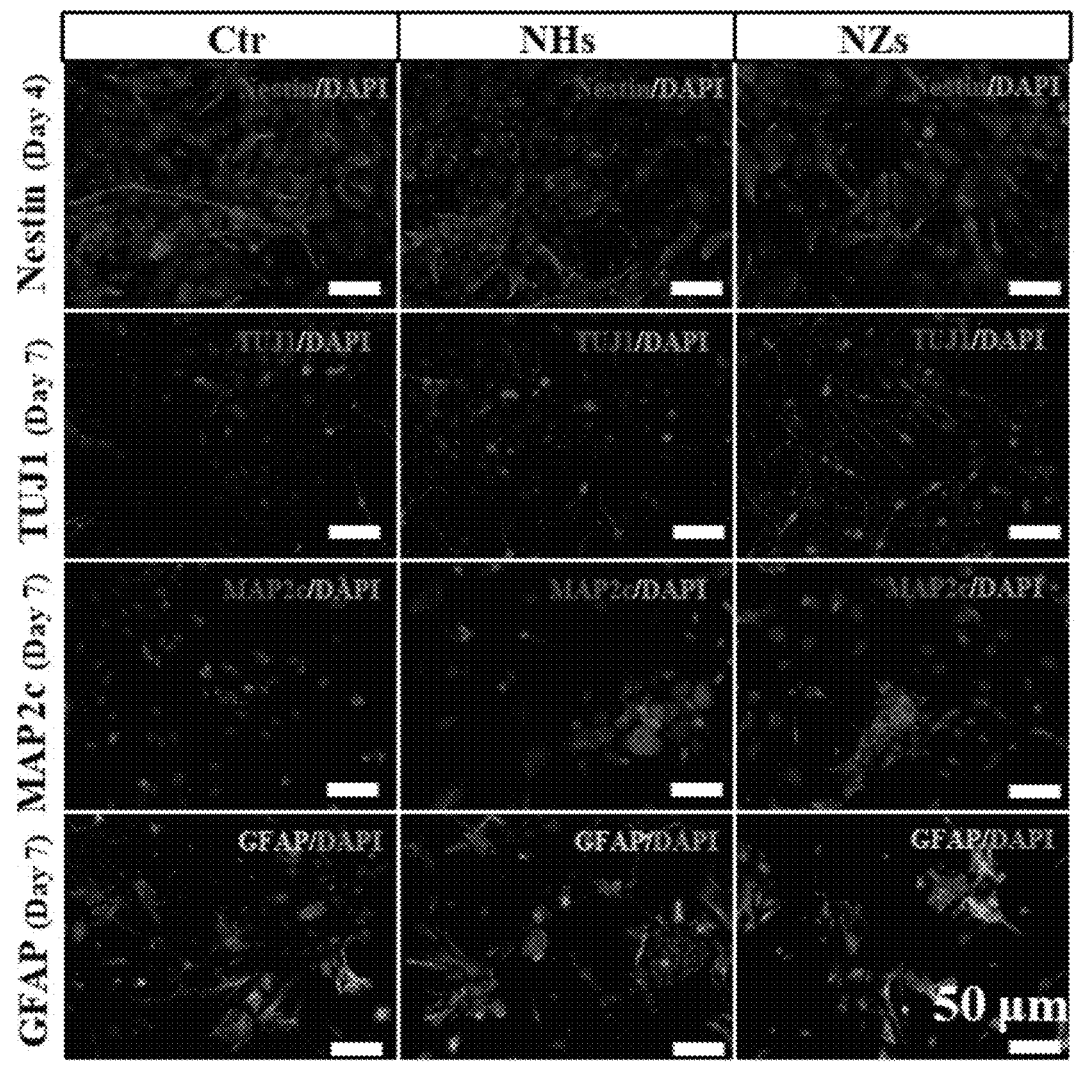
FIG. 16d shows proliferation and neural differentiation of NSCs mediated by the silica iSECnMs. Differentiation of NSCs on the silica iSECnMs of L-NHs and NZs for day 4 and day 7 was monitored by immunofluorescence staining. Immunofluorescence staining of the differentiated markers: Nestin (day 4, stained in red), TUJ1 (day 7, stained in red), MAP2c (day 7, stained in red) and GFAP (day 7, stained in green). Scale bar: 50 μm.

For in vitro differentiation of NSCs, compared with the control group the iSECnMs cause the expression of Nestin protein (NSC marker) to significantly decrease on day 4 (nearly independent on the sculptured shape), and lead to those of TUJ1 (a marker of maturing neurons) and MAP2c (involved in synaptogenesis, which is down regulated in the later stages of neuronal development) proteins significantly increases on day 7 (FIG. 16c). The expression of TUJ1 proteins on the NZs is evidently higher than that on the NHs. On the other hand, the expression of MAP2c on NHS is higher than NZs. This shows that the NSC differentiation on the NZs is swifter than that on the NHs. Meanwhile, the NZs show a tendency to reduce the expression of GFAP (a marker of astrocytes) than the control and NHs groups (FIG. 16c). It is illustrated that the NZs markedly promote the NSC differentiation into neurons and suppress the differentiation into astrocytes. The immunofluorescence staining results (FIG. 16d) are in well agreement with the western blot results in FIG. 16c. The mediation by GFs and three-dimensional nanofibrous scaffolds leads to the NSC differentiate into both neurons and astrocyte cells. As a result, the silica NZs of the present invention outweigh the existing techniques and capable to make NSCs preferentially differentiate into neurons.

Figure 16E:
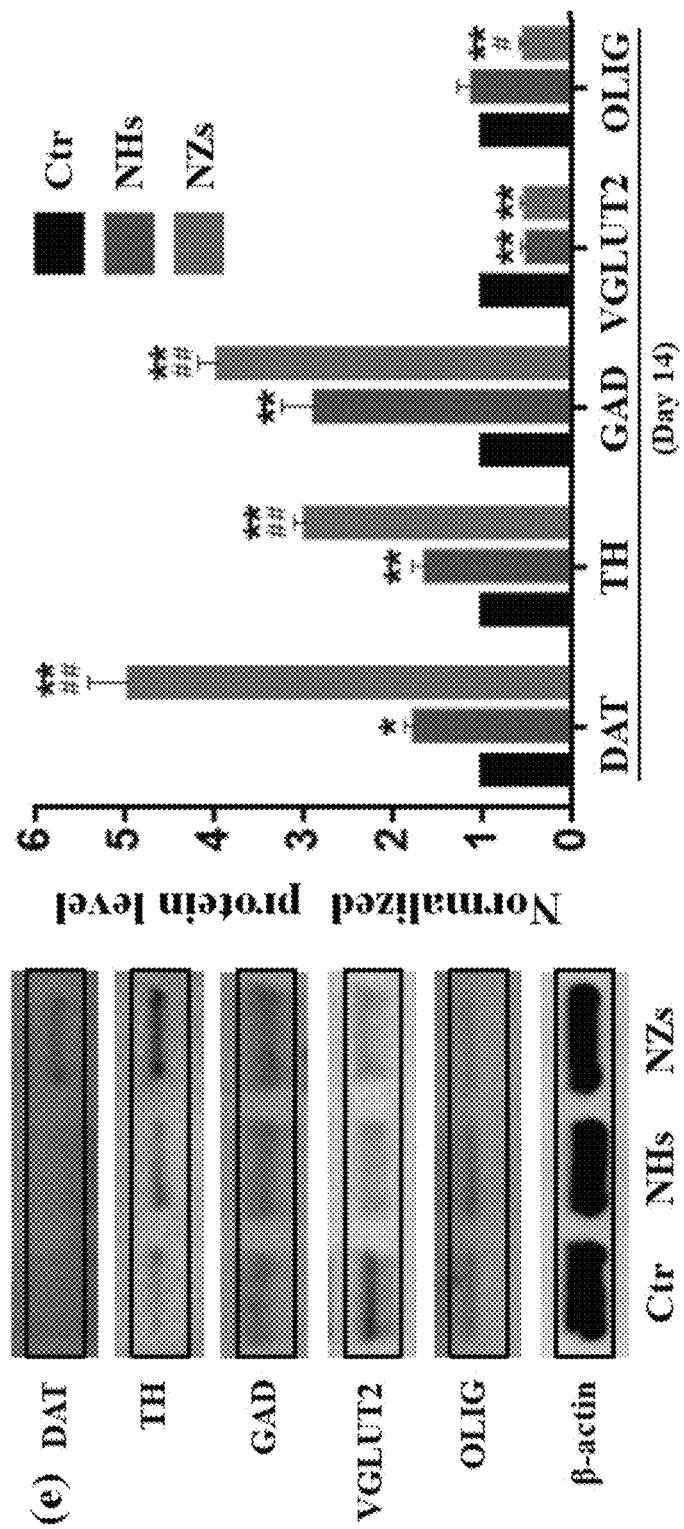
FIG. 16e shows proliferation and neural differentiation of NSCs mediated by the silica iSECnMs. The expression of specific neural markers mediated by iSECnMs for 14 days was further monitored. L-NHs and NZs iSECnMs significantly up-graduated the expression of DAT, TH and GAD, while suppressed the expression of VGLUT2 and Oligo, especially on the NZs. β-actin was used as a reference to assess the relative optical of proteins. Relative optical density was normalized by Ctr group, *$p<0.05$, and **$p<0.01$ compared with the control group; #p<0.05 and ##p<0.01 compared with the L-NHs iSECnMs.

The NSC differentiation on the silica iSECnMs for 14 days is shown in FIG. 16e. As seen in FIG. 16e, the NZs significantly amplify the expression of DAT (marker of Dopaminergic (DA) neurons), TH (marker of DA neurons), and GAD (marker of GABAergic neurons that are able to strengthen the function of DA neurons. However, the expression of VGLUT2 (glutamatergic neurons) and oligodendrocytes were suppressed remarkably. These results indicate that NZs iSECnMs significantly promote NSCs neural differentiation, specifically differentiation to dopamine neurons.

It is comprehensively illustrated that with the absence of neurogenic chemical growth factors, the silica iSECnMs can effectively promote the NSC proliferation and stimulate the differentiation of NSCs to neuronal cells. The NZs of the present invention are favored for the swift NSC differentiation into functional neuronal cells, and for the prohibition of the NSC differentiation into glia cells (such as astrocytes and oligodendrocytes). This quick cell maturation achieved by the present invention is highly desired for transplantation as it shortens the culture time and minimize the medical and contamination risk.

Figure 17A:
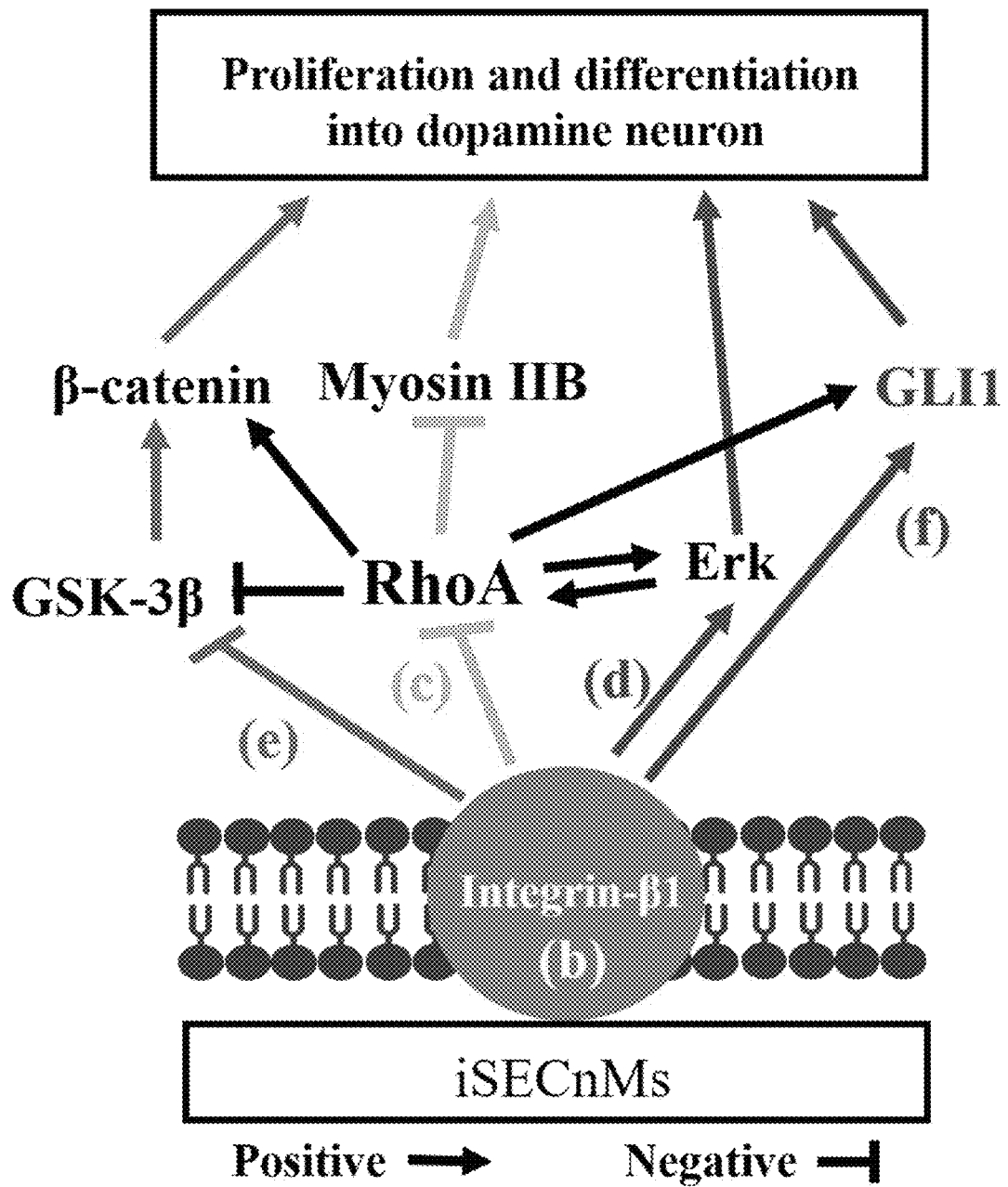
FIG. 17a shows multiple-mechanism driven by physiological cues was involved in the iSECnM-mediated NSCs induction. A roadmap of multiple-mechanism involved in the iSECnM-mediated NSCs proliferation and specific neural differentiation.
Figure 17B:
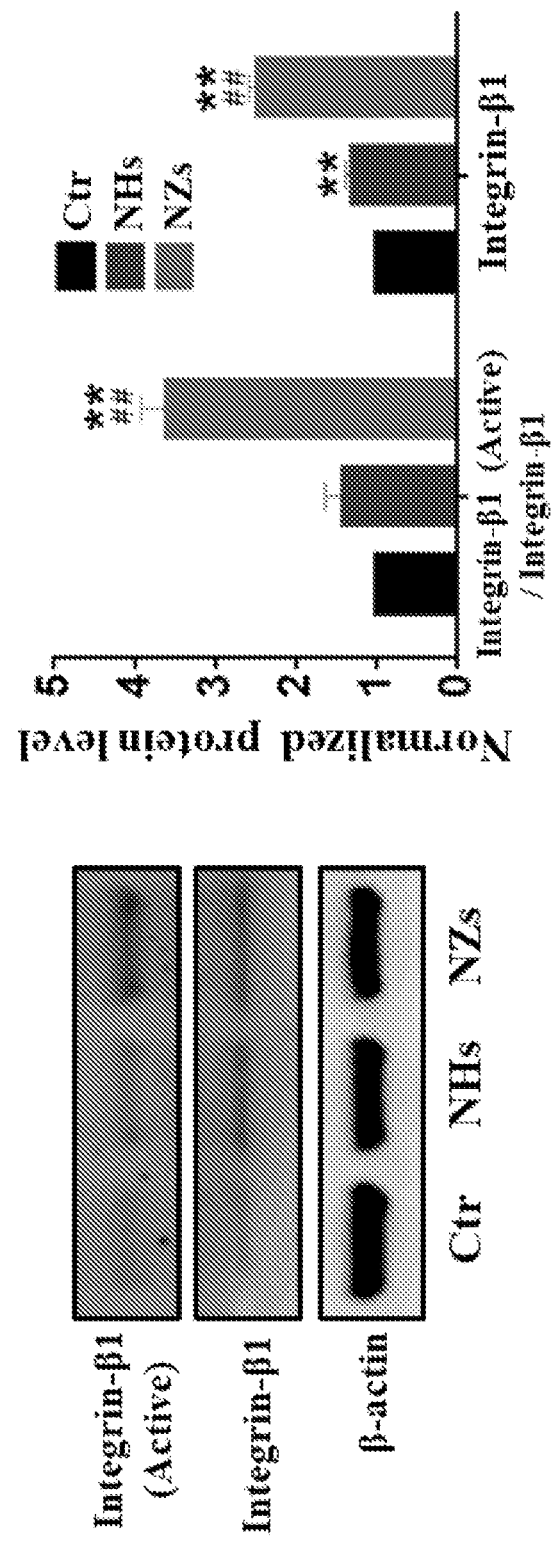
FIG. 17b shows multiple-mechanism driven by physiological cues was involved in the iSECnM-mediated NSCs induction. The expression and activation of integrin-β 1 was up-regulated on iSECnMs, in which NZs was more obvious than NHs.
Figure 17C:
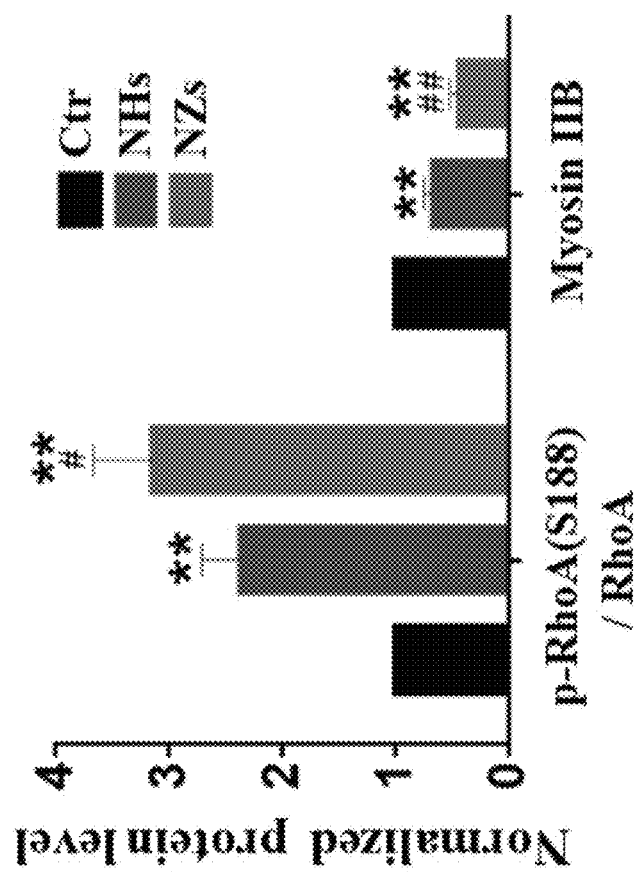
FIG. 17c shows multiple-mechanism driven by physiological cues was involved in the iSECnM-mediated NSCs induction. The activation of RhoA and expression of Myosin II B was significantly suppressed on iSECnMs, more distinct on NZs than NHs.
Figure 17C:
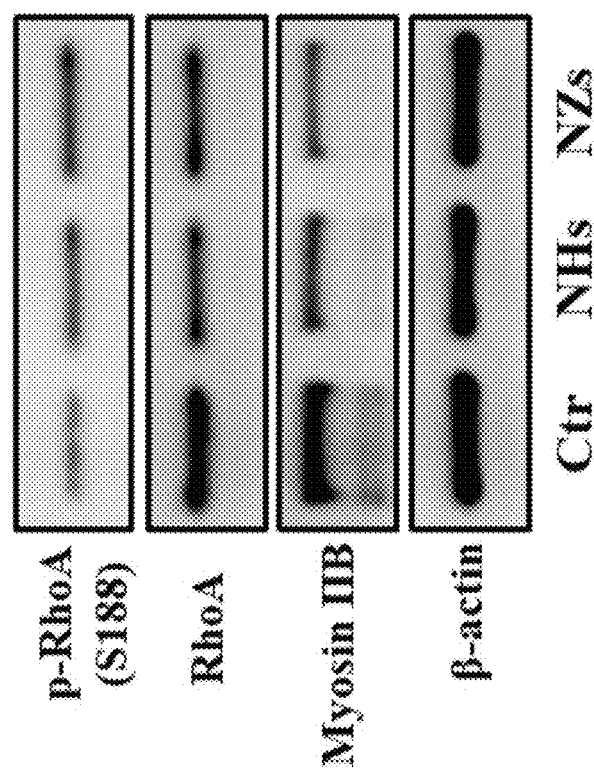
Figure 17D:
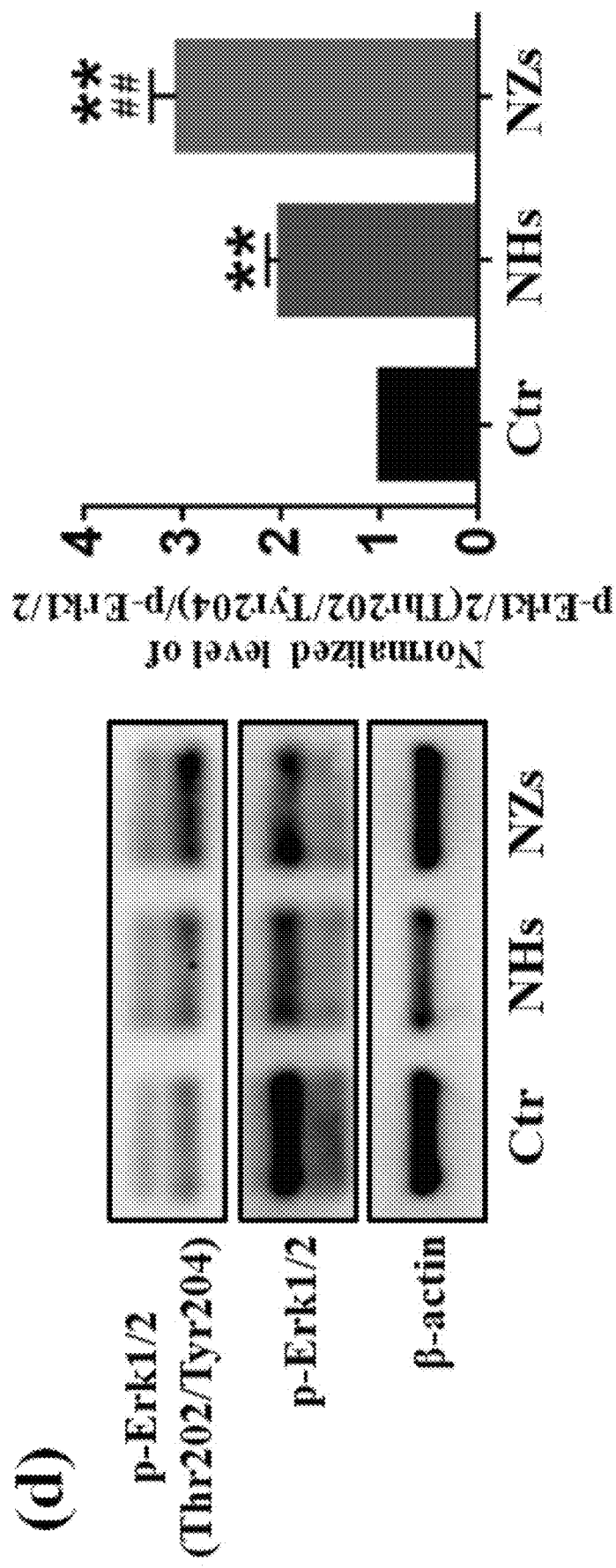
FIG. 17d shows multiple-mechanism driven by physiological cues was involved in the iSECnM-mediated NSCs induction. The proportion of p-GSK-3β (Ser9)/GSK-3β and (β-catenin (Active)/β-catenin was significantly increased on iSECnMs, indicating the Wnt/β-catenin pathway was activated on NZs iSECnMs and then NHs.
Figure 17E:
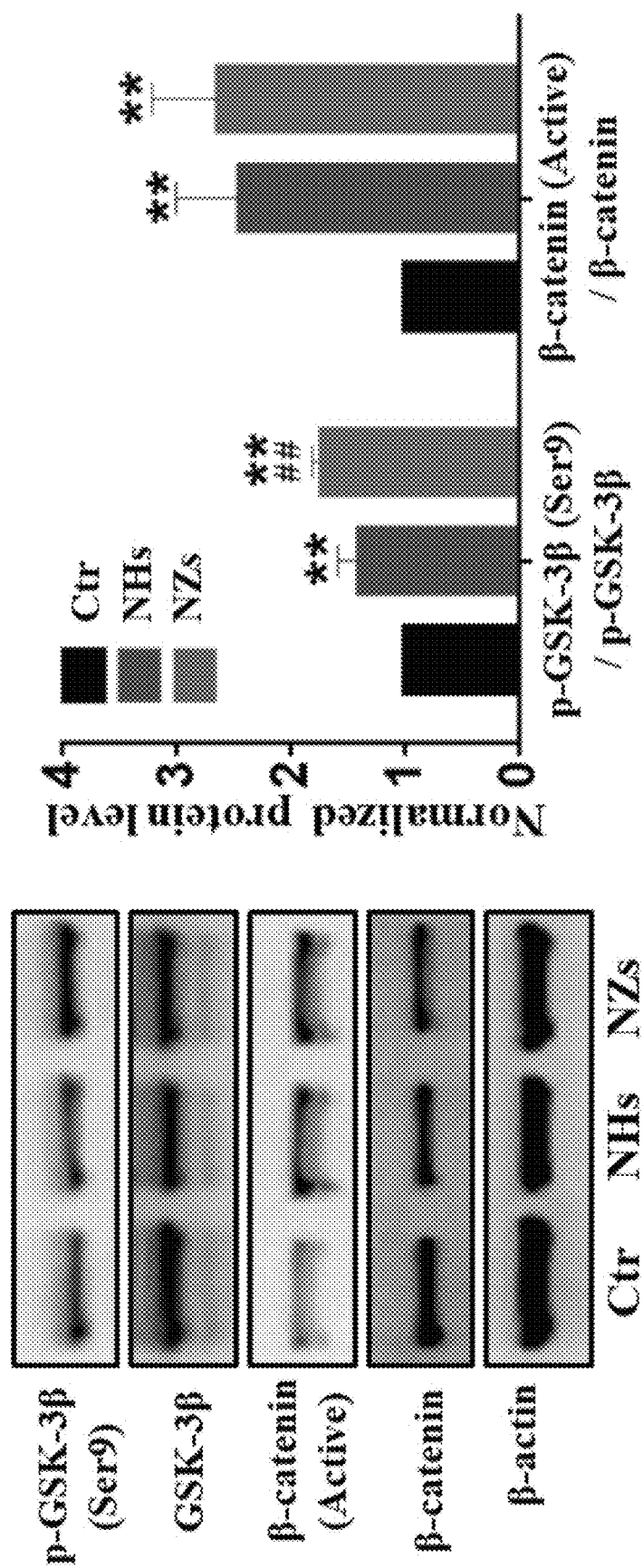
FIG. 17e shows multiple-mechanism driven by physiological cues was involved in the iSECnM-mediated NSCs induction. The Erk1/2 was activated on iSECnMs.
Figure 17F:
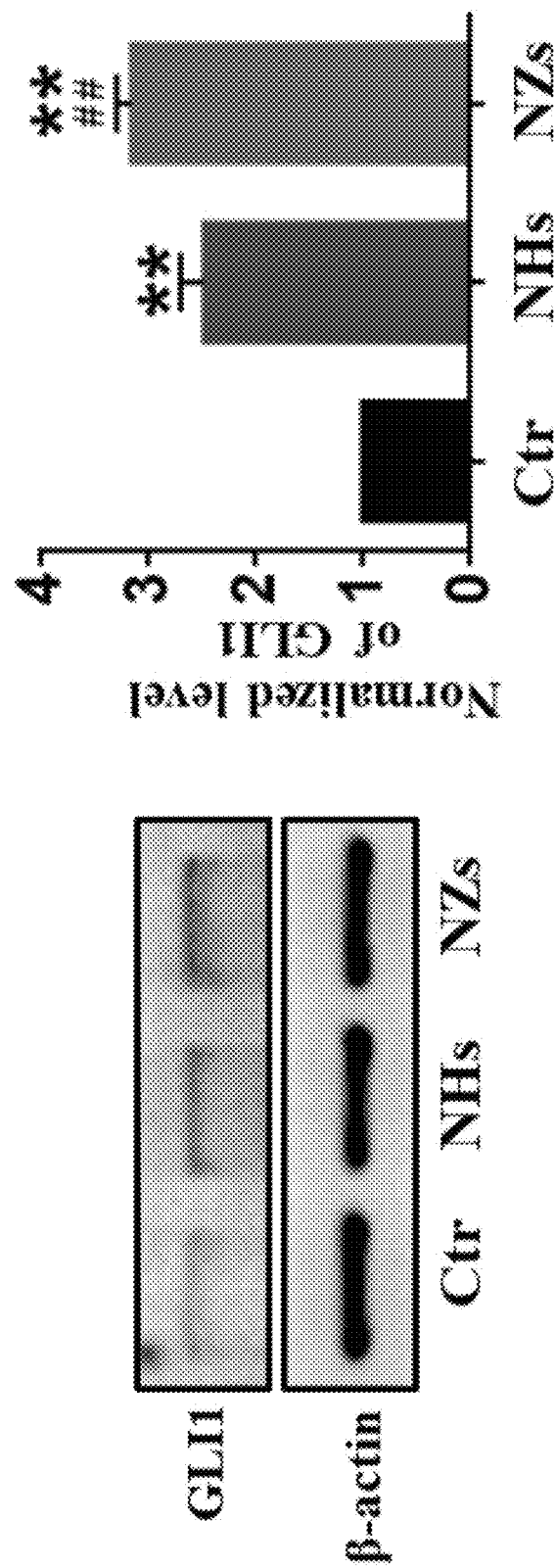
FIG. 17f shows multiple-mechanism driven by physiological cues was involved in the iSECnM-mediated NSCs induction. The expression of GLI1 was remarkably increased on NZs iSECnMs, followed by NHs, then Ctr group. β-actin was used as a reference to assess the relative optical of proteins. Relative optical density was normalized by Ctr group, *p<0.05, and **p<0.01 compared with the control group; #p<0.05 and ##p<0.01 compared with the NHs iSECnMs.

The NSC differentiation can be induced through multiple bio-signaling pathways, as shown in FIG. 17a: Integrin-β1 is a heterodimeric surface molecule that regulates intracellular and extracellular signaling pathways to effectively affect stem cell survival, migration and differentiation; ras homolog gene family member A (RhoA), which can be regulated by intergrin-β1, plays a crucial role in regulating cellular response to mechanical cues, and the inhibition of RhoA activity through the phosphorylation at Ser188 (p-RhoA (S188)) and that of the downstream factor Myosin IIB can promote the NSC differentiation into DA neurons; the Wnt/β-catenin signaling, which also can be enhanced by the RhoA inactivation, is believed to be a critical regulator for neural differentiation of NSCs; inhibition of the GSK-3β activity by the Ser9-phosphorylated GSK-3β (i.e., p-GSK-3β (Ser9)) can cause the activated β-catenin to accumulate in the cytoplasm and activate the Wnt/β-catenin signaling pathway; the Erk1/2 pathway, which is activated through the phosphorylation at Thr202/Tyr204 (p-Erk1/2), can contribute to the proliferation and differentiation of NSCs; the RhoA inhibition leads to the Erk activation, and vice versa; GLI1 is a crucial transcription factor and activation marker in the SHH pathway, which is found to overexpress in RhoA-deficient midbrain. In the order of the control (glass), the NHs and the NZs, there is an increase in the expression and activation of integrin-β1 (FIG. 17b), the ratio of p-RhoA (S188) to total RhoA (FIG. 17c), the activation of Erk1/2 (FIG. 17d), the expression ratio of p-GSK-3β (Ser9) to total GSK-3β (FIG. 17e), the expression ratio of active β-catenin to total β-catenin (FIG. 17e), and the expression of GLI1 (FIG. 17f); and there is a suppression of the expression of Myosin IIB (FIG. 17c). It is demonstrated that these multiple bio-signaling pathways are effectively activated by the silica iSECnMs, especially sculptured in the NZs. It was reported that the Wnt/β-catenin pathway is elevated in the NSC differentiation on a chitosan scaffold, in a good agreement with the inventors' result. Furthermore, it was reported that nerve growth factor (NGF) can initiate neural differentiation of NSCs through RhoA inactivation or Erk activation, which also can be achieved through iSECnMs induction, might be partly account for the minimal usage of GFs on iSECnM.

Figure 17G:
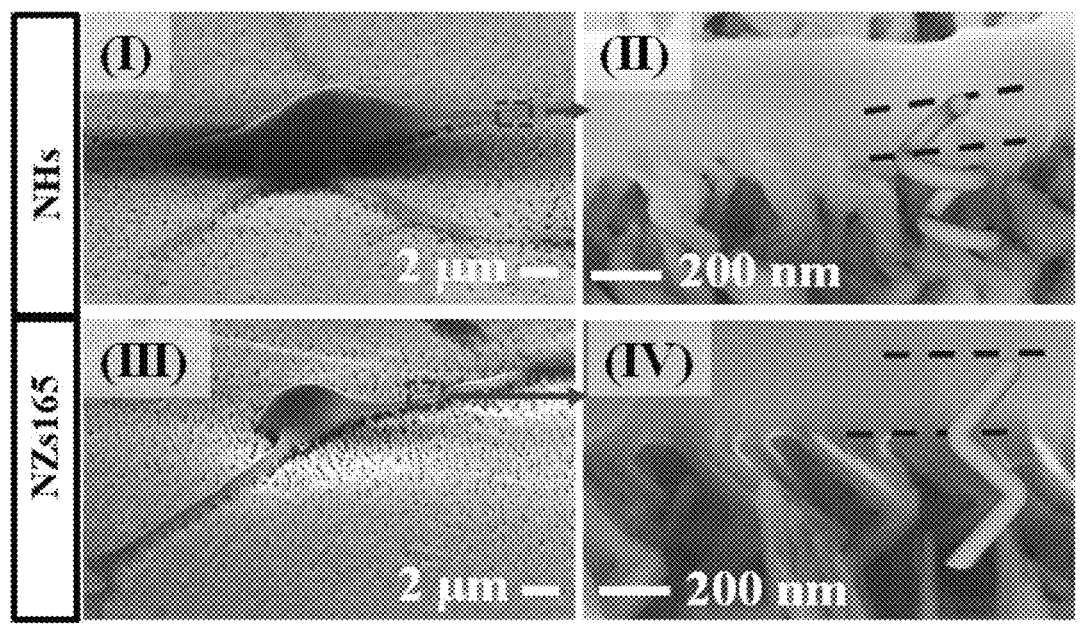
FIG. 17g shows multiple-mechanism driven by physiological cues was involved in the iSECnM-mediated NSCs induction. SEM cross-sectional images for investigation in the physiological cues of the iSECnM-mediated NSC proliferation and differentiation, in terms topography of the (I, II) NHs and (III, IV) NZs iSECnMs.
Figure 19A:
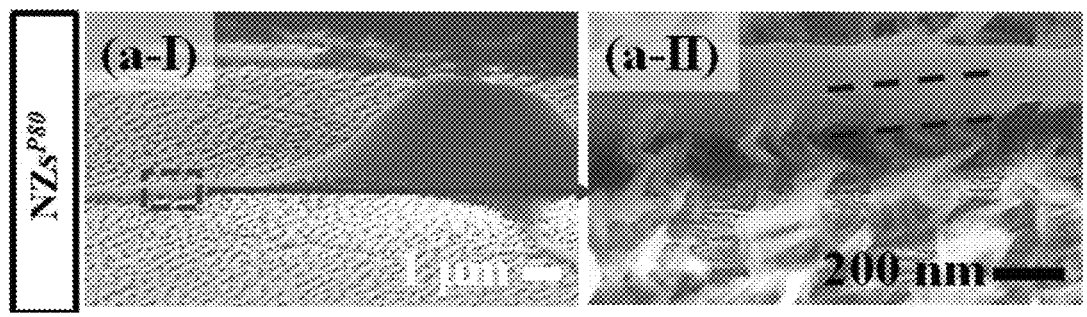
FIG. 19a shows the cell-matrix contact depth, investigated the physiological cues of the iSECnM-mediated NSC proliferation and differentiation. Cross-sectional SEM images of Neurons differentiated on the silica NZs with a P$_Z$ of ~80 nm (i.e., the NZs$^{P170}$) for 7 days.
Figure 19B:
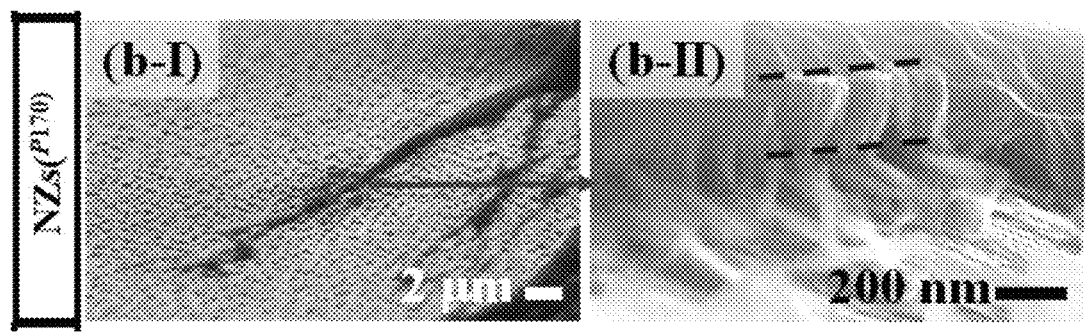
FIG. 19b shows the cell-matrix contact depth, investigated the physiological cues of the iSECnM-mediated NSC proliferation and differentiation. Cross-sectional SEM images of Neurons differentiated on the silica NZs with a Pz of ~170 nm (i.e., the NZs$^{P170}$) for 7 days.
Figure 19C:
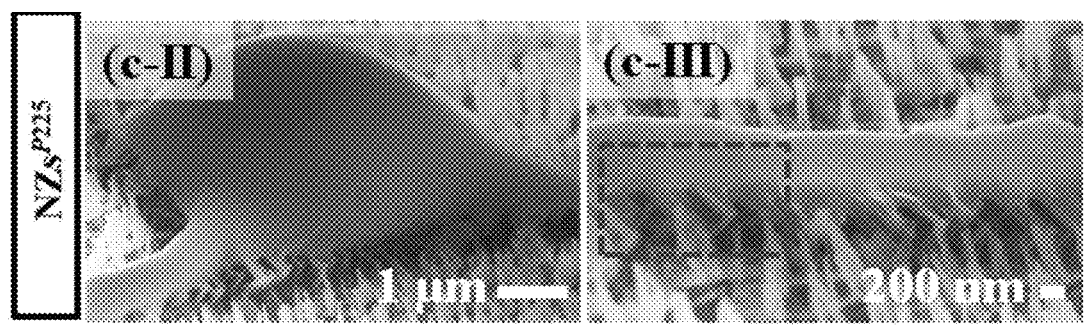
FIG. 19c shows the cell-matrix contact depth, investigated the physiological cues of the iSECnM-mediated NSC proliferation and differentiation. Cross-sectional SEM images of Neurons differentiated on the silica NZs with a Pz of ~225 nm (i.e., the NZs$^{P225}$) for 7 days.
Figure 20A:
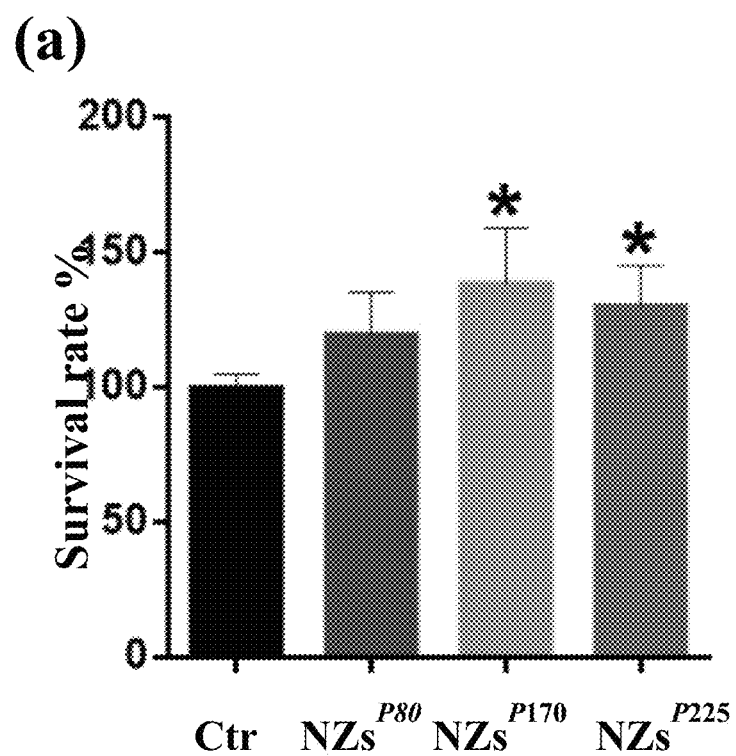
FIG. 20a shows proliferation and differentiation of NSCs cultured on the silica NZs having a zigzag pitch of ~80 nm (i.e., NZs$^{P80}$), ~170 nm (i.e., NZs$^{P170}$) and ~225 nm (i.e., NZs$^{P225}$). Survival rate of NSCs in culture on day 4 and 7. *p<0.05, compared with the control group.
Figure 20B:
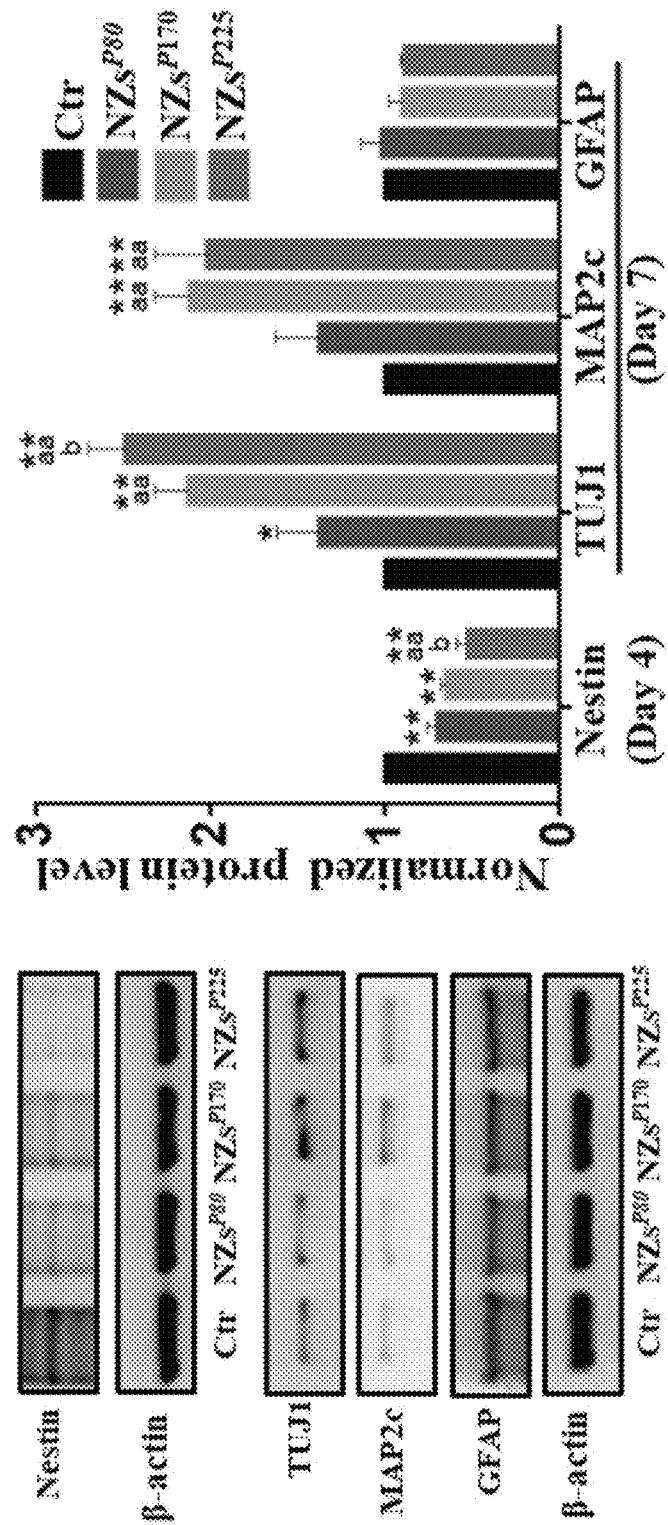
FIG. 20b shows proliferation and differentiation of NSCs cultured on the silica NZs having a zigzag pitch of ~80 nm (i.e., NZs$^{P80}$), ~170 nm (i.e., NZs$^{P170}$), and ~225 nm (i.e., NZs$^{P225}$). Western blot analysis of diverse protein markers on day 4 (Nestin) and day 7 (TUJ1, GFAP and MAP2c). β-actin was used as a reference to assess the relative optical of proteins. *p<0.05, **p<0.01 compared with the control group (i.e., Ctr); aap<0.01 compared with the NZs$^{P80}$; bp<0.05 compared with the NZs$^{P170}$.

As characterized by SEM, the differentiated neuron cells appear to spread on the iSECnMs and strongly adhere to the sculptured nanostructures (FIG. 17g, and FIG. 19a-c), consistent with the previous report that the cellular interaction with the 2D ECMs happens at the cell bases. The fibrillar focal contacts are formed to an extent that the spreading neuronal cells strongly wrap the top portions of the iSECnMs. Given the similar stiffness of the silica NHs and NZs, it is shown that the NSCs can physically perceive the topographies of the iSECnMs, and the topographic cues account for the NZ-promoted proliferation and differentiation of NSCs. The topographic cues, including geometrical profile of the cell-matrix contacts and contact depth (dc) of the cells, have been reported to play an essential role in the NSC differentiation. For the geometrical profile of the cell-matrix contacts, the NHs exhibit a helical profile while the NZ arrays uniquely have disorder grooves. It was reported that the NSC differentiation is favored on the nano-patterned substrates with grooves, consistent with the NZ-mediated results. It may be ascribed to that the topographic grooves can enhance focal adhesion and allow more physical contacts between the growing cells and the sculptured nanostructures, especially when the neuritis expands to the spaces in the grooves. It was reported that large dc is favored for the differentiation of human mesenchymal stem cells to the osteoblast lineage, through developing a high level of cellular organization. In this present invention, it was characterized by SEM that dc is roughly equal to a half pitch of the NHs (FIG. 17g (I-II)) and one pitch of the NZs (FIG. 17g(III-IV), and FIGS. 19a-19c), and the evaluation of dc for the diverse iSECnMs are summarized in Table 2. The differentiating NSCs perceive a dc on the NZs with the PZ of ~170 nm larger than that on the NHs (192±4 nm for the NZs versus 146±4 nm for the NHs), resulting in the NZ-mediated facilitation of the NSC differentiation. Furthermore, elongating zigzag pitch from 80 to 225 nm leads to the elongation of dc from 90 to 260 nm and an increase of the iSECnM stiffness from 0.62 to 7.85 GPa (Table 2), which is favored for the NSC differentiation to neurons (FIG. 20b). It should be noted that bad pre-melting of silica targets, an unavoidable phenomenon occurring in the electron-beam evaporation of silica, slows down deposition rate during GLAD and deposition duration is severely prolonged. As a result, further elongation of Pz above 225 nm seriously causes an unrepeatable deposition of the silica NZs over the macro-scale area, prohibiting one from fully studying the $P_Z$-elongation effect on the mediation of the NSC proliferation and differentiation at the current stage. However, the inventors clearly demonstrate that the NSC proliferation and differentiation can be effectively engineered through tailoring the sculptured nanostructures.

Figure 18A:
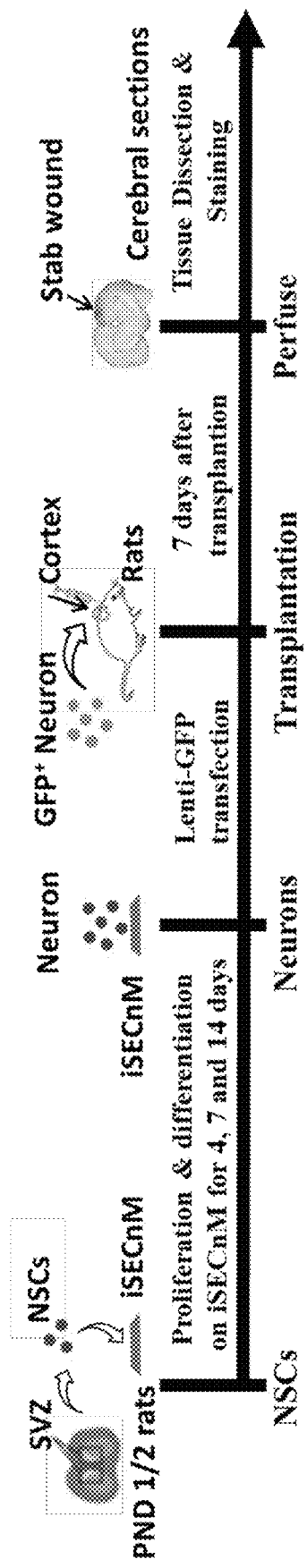
FIG. 18a shows transfection and transplantation of the differentiated neurons into adult parietal cortex. An overview protocol of neuron transfection and transplantation.
Figure 18B:
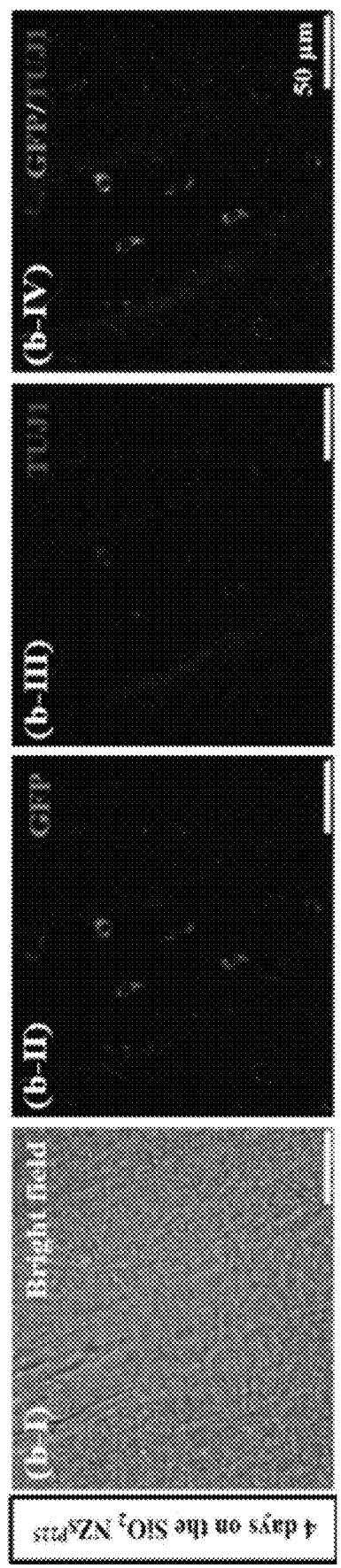
FIG. 18b shows transfection and transplantation of the differentiated neurons into adult parietal cortex. Neural cells, induced on the silica NZs with a Pz of ~225 nm (i.e., the NZs$^{P225}$) for 4 days are transplanted into adult cortex. Immunofluorescent images in a vicinity of the primary transplantation on day 7 after the transplantation: (b-I) bright field images, (b-II) immunolabeled GFP$^+$ transplanted cells (in green), (b-III) TUJ1$^+$ cells (in red), and (b-IV) merged image of (b-II) and (b-III). Scale bars: 50 μm.
Figure 18C:
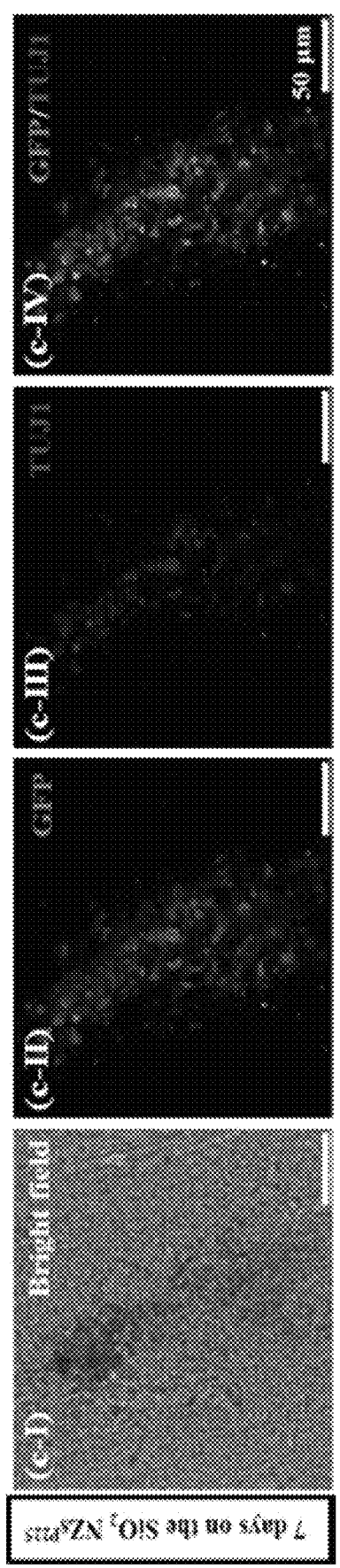
FIG. 18c shows transfection and transplantation of the differentiated neurons into adult parietal cortex. Neural cells, induced on the silica NZs with a Pz of ~225 nm (i.e., the NZs$^{P225}$) for 7 days are transplanted into adult cortex. Immunofluorescent images in a vicinity of the primary transplantation on day 7 after the transplantation: (c-I) bright field images, (c-II) immunolabeled GFP$^+$ transplanted cells (in green), (c-III) TUJ1$^+$ cells (in red), and (c-IV) merged image of (c-II) and (c-III). Scale bars: 50 μm.
Figure 18D:
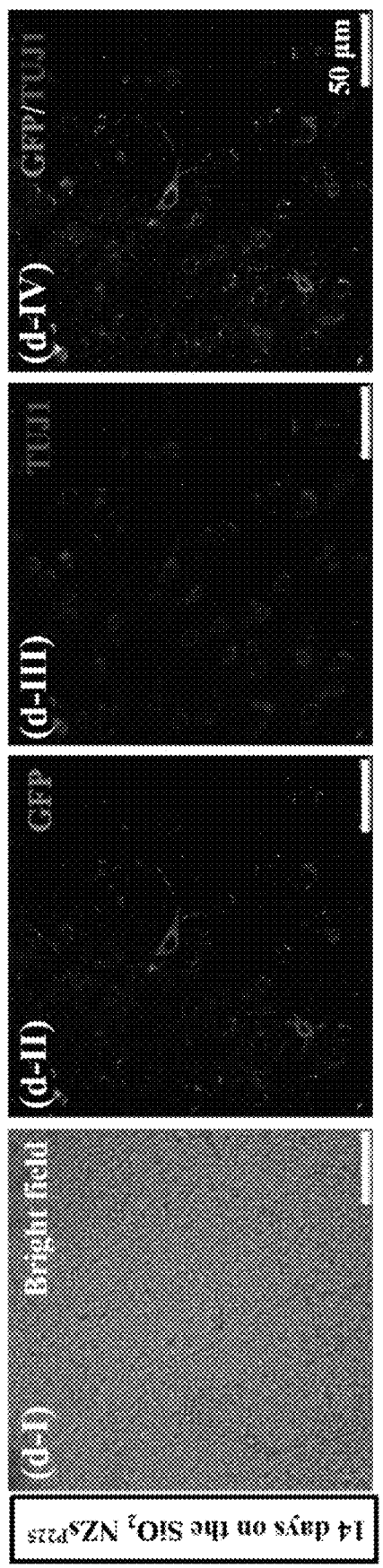
FIG. 18d shows transfection and transplantation of the differentiated neurons into adult parietal cortex. Neural cells, induced on the silica NZs with a Pz of ~225 nm (i.e., the NZs$^{P225}$) for 14 days, are transplanted into adult cortex. Immunofluorescent images in a vicinity of the primary transplantation on day 7 after the transplantation: (d-I) bright field images, (d-II) immunolabeled GFP$^+$ transplanted cells (in green), (d-III) TUJ1$^+$ cells (in red), and (d-IV) merged image of (d-II) and (d-III). Scale bars: 50 μm.
Figure 18E:
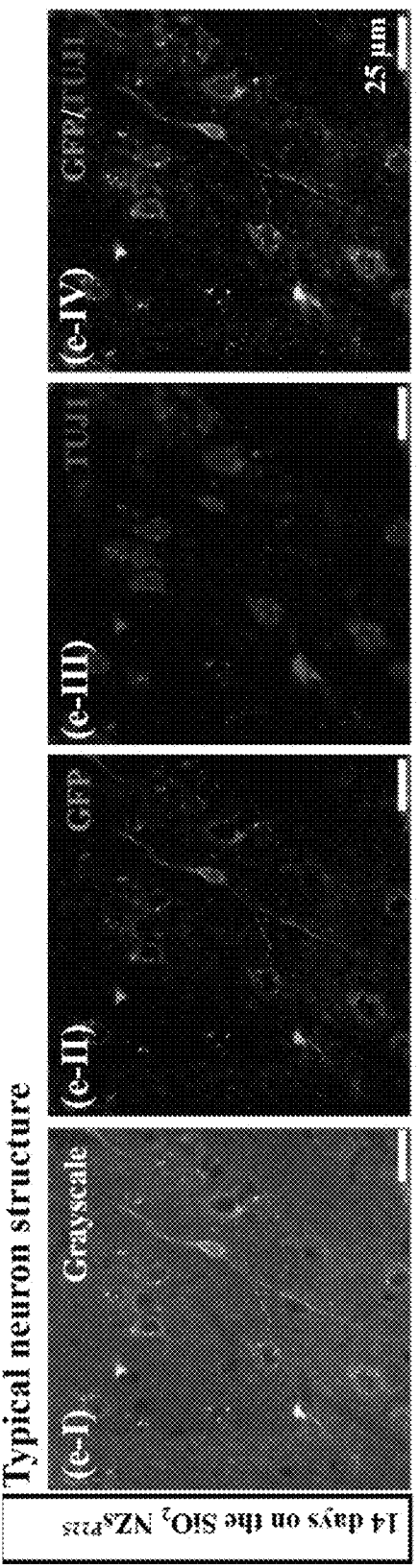
FIG. 18e shows a typical neuron structure of neurons after transfection and transplantation of the differentiated neurons into adult parietal cortex. Neural cells, induced on the silica NZs with a Pz of ~225 nm (i.e., the NZs$^{P225}$) for 14 days are transplanted into adult cortex. Immunofluorescent images of transplanted neurons in the adult cortex: (e-I) grayscale image, (e-II) GFP staining (in green), (e-III) TUJ1 staining (in red), and (e-IV) merged image of (e-II) and (e-III). Scale bars: 25 μm.
Figure 21A:
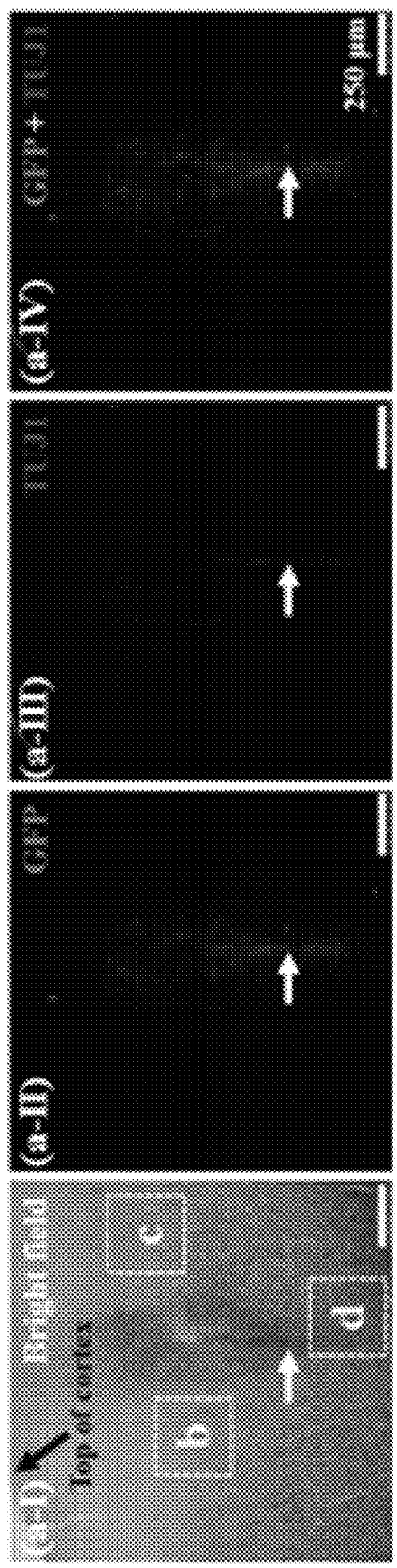
FIG. 21a (Low-magnification) shows neuron transplantation into adult parietal cortex. Neural cells, induced on the silica NZs with the PZ of ~225 nm for 14 days, were transplanted into adult cortex. Low-magnification images in a vicinity of the primary transplantation (marked by white arrows) on day 7 after the transplantation. White square for high-magnification observation (shown in FIGS. 21b, 21c and 21d). Scale bars: 250 μm. (a-I) bright field images, (a-II) immunolabeled GFP staining (in green), (a-III) TUJ1 staining (in red), and (a-IV) merged images of (a-II) and (a-III).
Figure 21B:
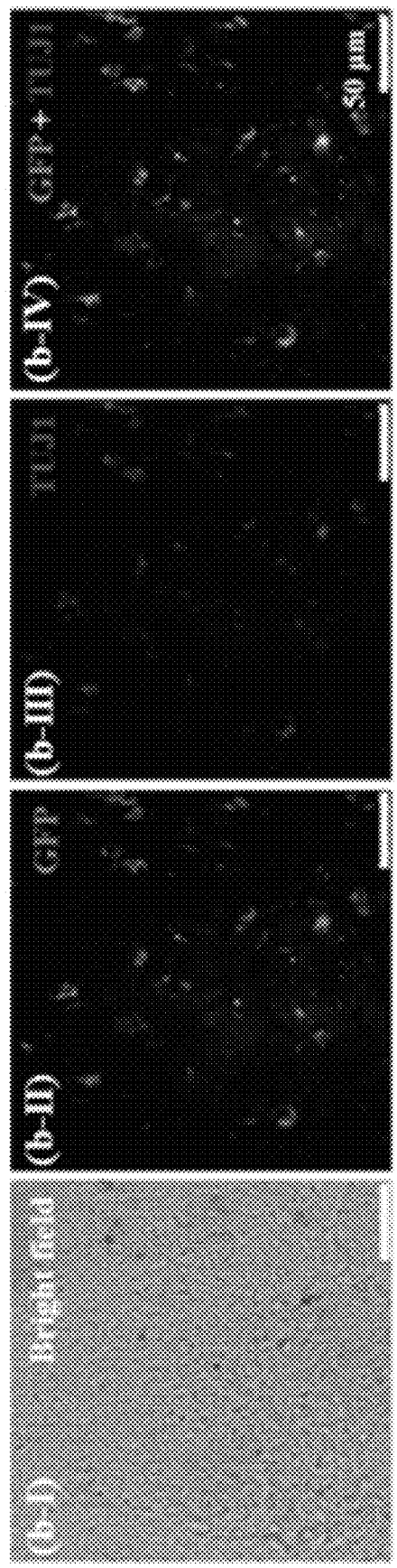
FIG. 21b (High-magnification) shows neuron transplantation into adult parietal cortex around the site of the primary transplantation. Neural cells, induced on the silica NZs with the PZ of ~225 nm for 14 days, were transplanted into adult cortex. Scale bars: 50 μm. (b-I) bright field images, (b-II) immunolabeled GFP staining (in green), (b-III) TUJ1 staining (in red), and (b-IV) merged images of (II) and (III).
Figure 21C:
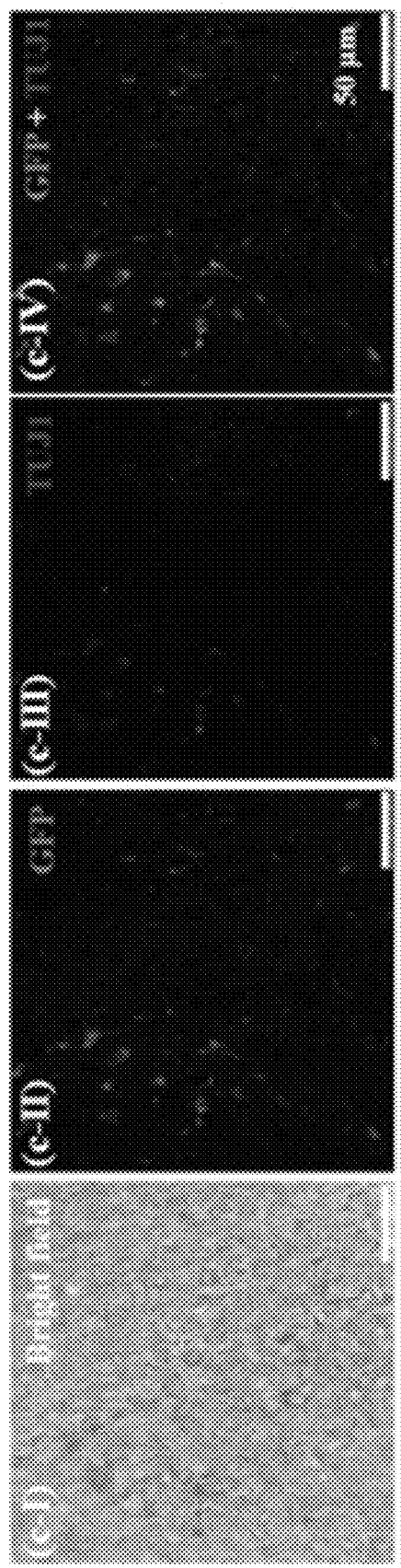
FIG. 21c (High-magnification) shows neuron transplantation into adult parietal cortex around the site of the primary transplantation. Neural cells, induced on the silica NZs with the PZ of ~225 nm for 14 days, were transplanted into adult cortex. Scale bars: 50 μm. (c-I) bright field images, (c-II) immunolabeled GFP staining (in green), (c-III) TUJ1 staining (in red), and (c-IV) merged images of (II) and (III).
Figure 21D:
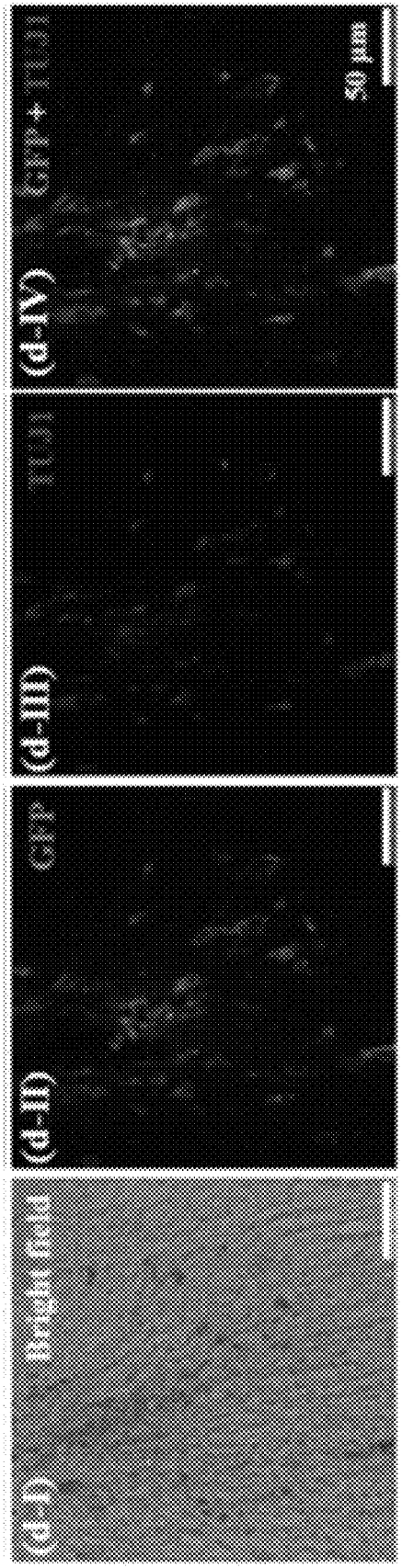
FIG. 21d (High-magnification) shows neuron transplantation into adult parietal cortex around the site of the primary transplantation. Neural cells, induced on the silica NZs with the PZ of ~225 nm for 14 days, were transplanted into adult cortex. Scale bars: 50 (d-I) bright field images, (d-II) immunolabeled GFP staining (in green), (d-III) TUJ1 staining (in red), and (d-IV) merged images of (II) and (III).

To investigate the survivability of the differentiated NSCs on silica NZs of the present invention, NSCs were differentiated on the silica NZs with the Pz of ~225 nm for 4, 7 and 14 days, labeled with GFP, and then transplanted into parietal cortexes of an adult rat. On day 7 after transplantation, immunofluorescence of the cerebral sections was analyzed to monitor the expression of GFP and TUJ1 (FIG. 18a). During a 14-day differentiation period on the NZs, GFP$^+$ and TUJ1$^-$ cells tend to widely spread in the vicinity of the primary transduction (FIGS. 18b-18d). On 14$^{th}$ day of differentiation, the neuronal cells exhibit the neurite-like and neuronal perikaryal structures (FIG. 18e). Additionally, TUJ1$^+$ and GFP$^-$ cells with bouton-like structures can be found in a close proximity of neuronal perikarya. When observation was made around the site of the primary transplantation, some GFP$^-$ cells migrate towards the top of the cortex (FIG. 21a) and many GFP$^+$ and TUJ1$^+$ cells appear to widely spread with the neurite-like structures (FIGS. 21b-21d). It is indicated that there are valid migration of the differentiated neuronal cells and neurite extension into the transplanted cortex. In the state of art, it was reported that NSCs could hardly survive after direct transplant to the cerebral cortex. On the contrary, the silica iSECnMs of the present invention has demonstrated NSC differentiation and aftermath survival of the transplanted cells using minimal GFs: one-week culturing of NSCs on the silica NZs, most of the GFP$^+$ cells have not been maturely differentiated, while in the two-week differentiation, many transplanted cells evidently exhibit a mature pattern of neuronal differentiation and GFP$^+$ bouton-like structures that are likely to be neuronal synapses. It is shown the two-week NZ-mediated culturing results in NSCs to be maturely differentiated and capable of forming functional synaptic connections with the neurons in the brain in situ. Therefore, the present invention provides a silica iSECnM-based procedure for NSC differentiation and neuronal cell therapies.

To the best of the inventors' knowledge, this is the first report on the GLAD sculptured ECM-mediated in vitro NSCs proliferation and specific neural differentiation in the absence of neurogenic chemical growth factors through multiple-mechanism to create a mini-SN organ. The zigzag topography exhibits a large number of grooves that are lack in the helical iSECnMs to strongly enhance cell adhesion and induction. Elongation of the zigzag pitch in the range of 80-250 nm makes the silica NZs become stiff and provide long contact depth, to effectively facilitate the neuronal differentiation. The differentiated neurons can survive, retain neuronal characteristics, migrate to the cortexes and then form functional connections in vivo after transplantation. The present silica iSECnM can be clinically utilized for stem cell therapies. Given the Pz elongation-induced facilitation of the NSC differentiation, in one embodiment, the silica iSECnM has an elongated Pz of above 250 nm for faster NSC differentiation.

The present invention has profound impacts on NSC therapies for neurodegenerative diseases, especially in PD. First of all, the minimal usage of GFs will significantly minimize the carcinogenic risk. Secondly, the silica iSECnMs can effectively promote the NSC differentiation preferentially into dopamine neurons. Thirdly, the GLAD technique enables one to flexibly engineer materials and structures of the iSECnMs, opening a door to tailor cell fate of diverse stem cells by engineering the matrix structures. Fourthly, GLAD technique offers a one-step-process production of the iSECnMs over a large area (e.g., on a 4-inch wafer) with uniform structures. Accordingly, the present invention provides means to differentiating NSCs to designable cell commitment with sufficient number of differentiated cells. The mini-SN of the present invention can be used to screen neurological drugs, specifically PD.

Experimental Section

GLAD of silica iSECnMs: In a custom-built physical vapor deposition system (JunSun Tech Co. Ltd., Taiwan) with a high vacuum of $10^{-7}$-$10^{-6}$ Torr, SiO$_2$ (99.99%, Kurt J. Lesker company) was evaporated at a rate of ~0.4 nm/s as monitored by a quartz crystal microbalance that was located in the vicinity of a sample, using an electron-beam accelerating voltage of 8.0 kV and emission current of 83-87 mA. $SiO_2$ was deposited at a deposition angle (α) of 87° with respect to the substrate normal. The samples were deposited on ITO-coated glasses (Xin Yan Technology Ltd.) and Si wafers (Semiconductor Wafer, Inc.), and the substrate temperature was retained at room temperature during GLAD using an ethanol/water cooling system. To produce left/right-handed NHs, the substrate was rotated counterclockwise/clockwise at a rate $R_r$ (in units of degree per second, or °/s) given by $$R_r = 360 \, R_d / P \qquad (1)$$

where $R_d$ is the deposition rate on the substrate surface calibrated as 0.28 nm/s for $SiO_2$ at a of 87°. $P_H$ is the helical pitch, as-designed to be ~200 nm. To produce the NZs, the substrate was stepped back and forth in 180° intervals, during which tilted nanorods were deposited with a given length (i.e., zigzag pitch or $P_Z$) as a function of deposition duration. The iSECnM structures are summarized in Table 2. Proliferation and differentiation of NSCs were mediated on the silica iSECnMs deposited on the ITO-coated glasses.

Material characterization: The deposited samples were mechanically split, leaving the freshly exposed surfaces for the structural characterization using scanning electron microscopy (SEM, Oxford, LEO 1530). The silica NHs and NZs were scratched off the substrates and well dispersed in ethanol via ultra-sonication for 5 min. Several drops of the mixture were applied to a lacey carbon film on a grid structure (Electron Microscopy Sciences). The grid was dried in ambient and inspected by transmission electron microscopy (TEM, Tecnai G2 20 STWIN). Without post-deposition treatment, the samples were characterized by X-ray diffraction (XRD, Bruker, nonmonochromated Cu Kα x-ray with wavelength of 0.15418 nm, Advance D8 multipurpose x-ray diffractometer), X-ray photoelectron spectroscopy (XPS, Sengyang SKL-12, non-monochromatic Mg Kα radiation of 1253.6 eV, at a current of 15 mA, voltage of 10 kV and takeoff angle (between the sample and detector) of 90°, and in a vacuum of $\sim 2 \times 10^{-9}$ mbar), and nanoindentation (Ubi 1 Nanomechanical Test Instrument, using a 3-sided pyramidal tips with a radius of 100-200 nm).

NSC isolation and cell culture: The experimental protocol was approved by Department of Health, the Government of the Hong Kong SAR and performed in accordance with relevant guidelines and regulations of the Animal Ethics Committee at Hong Kong Baptist University. Rats (Springe Dawley, postnatal day 1 to 2) were purchased from the Chinese University of Hong Kong (CUHK). NSCs were dissected from the subventricular zone (SVZ) and cultured at an appropriate density in 4-well or 6-well plates, in a complete medium composed of neurobasal medium (Theme scientific) dissolved with 10% fetal bovine serum (FBS, Theme scientific), 1% penicillin/streptomycin/neomycin (PSN, Theme scientific) and 2% B27 supplement (Theme scientific). Silica iSECnMs were sterilized in a steam autoclave at 121° C. for 20 min, and the NSC incubation was operated on the sterilized samples (without any chemical modification) for 4 and 7 days at 37° C., in an environment filled with 5% $CO_2$.

MTT assay: Survival rate of NSCs was evaluated by MTT assay to assess the cytotoxicity of the silica iSECnMs. NSCs were cultured on glass plates as a control group, and on the silica iSECnMs in 4-well plates filled with 1 ml complete medium per well. The incubation was operated for 7 days to characterize the MTT assay. MTT solution (Sigma-Aldrich) was applied to 4-hour incubation in dark, and then removed from the incubator. Dimethylsulfoxide (DMSO) was applied to dissolve the formazan crystals, the amount of which was proportional to the number of live cells. Optical density of the DMSO solution was measured by an automatic microplate reader (BioTek) at dual-wavelength of 540 nm and 690 nm.

Live/dead assay: Viability of the cells cultured on the iSECnMs, denoted a ratio of the number of living cells to that of total cells, was measured by live/dead viability/cytotoxicity kit (Invitrogen), according to the manufacturer's protocol. Fluorescence imaging and differential interference contrast were operated by confocal microscope (FluoView FV1000, Olympus). Quantitative analyses were made by manually counting at least 6 non-overlapping areas per sample.

Immunofluorescent staining: NSCs in culture were stained with nuclear stain, DAPI (1 μg/ml, Roche) in methanol, for 15 min in the incubator at 37° C. Then the cells were rinsed with 60% methanol, and fixed with 4% paraformaldehyde (PFA, Sigma) for 30 min at room temperature. The cells were further incubated with specific primary antibodies (Nestin, TUJ1, MAP2c and GFAP) solutions in PBS with 0.1% Triton X-100 (Sigma-Aldrich) and 2% normal goat serum (Vector Laboratories) overnight at 4° C. Then the cells were rinsed with PBS and then incubated with specific secondary antibody solutions in PBS for 3 hours at room temperature. The incubation was operated in dark. The cells were mounted with fluorescence mounting medium (Dako), and immunoreactivity of the cells was imaged by confocal microscope (FluoView FV1000, Olympus).

Western blotting assay: Western blotting assay was employed to compare the levels of cellular proteins. On day 4 and 7 in culture, proteins were extracted using protein extraction reagent (Novagen) supplemented with protease inhibitor cocktail (Calbiochem). Protein concentration was measured using the Bio-Rad protein assay kit (Bio-Rad). Total proteins (30 μg) per sample were separated on 10% SDS-polyacrylamide gels and transferred to a polyvinylidene difluoride (PVDF, Bio-Rad) membrane. The membrane was probed with diverse antibodies, including primary anti-Nestin antibody (Millipore, 1:1000), anti-TUJ1 antibody (Millipore, 1:1000), anti-MAP2c antibody (Millipore, 1:1000), anti-GFAP antibody (Millipore, 1:1000), anti-p-GSK-3β (Ser9) antibody (Cell Signaling, 1:1000), anti-GSK-3β antibody (Cell Signaling, 1:1000), anti-Non-p (Active) β-catenin antibody (Cell Signaling, 1:1000), anti-β-catenin antibody (Cell Signaling, 1:1000), anti-Integrin β1 (Millipore, 1:1000), anti-Integrin β1 activated (Millipore, 1:1000), anti-p-RhoA (S188) (Abcam, 1:1000), anti-RhoA (Cell Signaling, 1:1000), anti-Myosin IIB (Abcam, 1:1000), anti-p-Erk1/2(Thr202/Tyr204) (Cell Signaling, 1:1000), anti-Erk1/2 (Cell Signaling, 1:1000), anti-GLI1 (Cell Signaling, 1:1000), anti-Tyrosine Hydroxylase (TH; Millipore, 1:1000), anti-DAT (Millipore, 1:1000), anti-GAD (Chemicon, 1:1000), anti-VGLUT2(Millipore, 1:1000) and anti-Oligodendrocytes (Oligo; Millipore, 1:1000), followed by an incubation with a secondary antibody complementary to the primary antibody. (β-actin antibodies (Sigma, 1:5000) were used as a reference to assess the relative amounts of proteins loaded per lane. Images of bands were captured using ChemiDoc Touch imaging system (Bio-Rad).

Lenti-GFP transfection, neuron transplantation and tissue dissection: NSCs were differentiated on the $SiO_2$ NZs with a PZ of ~245 nm for 4, 7 and 14 days, and then were transfected with Lenti-GFP (GeneCopoeia) at a multiplicity of infection (MOI) of 5, monitored by fluorescence microscopy.

Adult rats were purchase from CUHK and anaesthetized by pentobarbital before the experiments. All procedures of animal experiments were approved by Department of Health, HKSAR Government and Committee on the Use of Human & Animal Subjects in Teaching and Research at HKBU. Single GFP$^+$ cell solutions were prepared and stored in ice before transplantation. 200,000 cells suspended in PBS (40,000 cell/μl PBS) were unilaterally injected into the right parietal cortex at a rate of ~1 μl/min, using Hamilton microsyringe (Hamilton Company). After 7 days of the injection, the transplanted rats were anesthetized again and perfused with 0.9% normal saline and 4% PFA through the left ventricle. Brain tissues were directly harvested and fixed in 4% PFA overnight at room temperature, and then in 0.9% normal saline for 2 days. Post-fixed brains were sliced at 50 μm/coronal section on a freezing-stage sledge microtome. Tissue sections were stored at 4° C. before immunohistochemistry visualization. To determine the viability of the differentiated neurons in vivo, anti-GFP (Abcam, 1:1000) and anti-TUJ1 antibody were used for the routine fluorescent staining.

Statistical analysis: The data were evaluated from three individual experiments to statistically obtain a mean±standard deviation. The statistical significance was determined by one-way analysis of variance (ANOVA) and defined as $p<0.05$. Image analysis and cell counting were operated using ImageJ. All graphs were produced using GraphPad Prism 5.0.

The invention claimed is:

1. A nanostructure comprising a plurality of nanozigzags, wherein the nanozigzags comprise $SiO_2$ having a stiffness of 19.7±2.3 μN/nm and the nanozigzags have a pitch of 80 nm to 250 nm, and a contact depth of 90 nm to 260 nm.

2. The nanostructure according to claim 1, wherein the nanozigzags comprise at least three pitches.

3. The nanostructure according to claim 1, wherein the nanozigzags having a pitch of 80 nm to 225 nm.

4. The nanostructure according to claim 3, wherein the nanozigzags having a pitch of 80 nm, 170 nm or 225 nm.

* * * * *